US008148164B2

(12) United States Patent
Diebold et al.

(10) Patent No.: US 8,148,164 B2
(45) Date of Patent: Apr. 3, 2012

(54) SYSTEM AND METHOD FOR DETERMINING THE CONCENTRATION OF AN ANALYTE IN A SAMPLE FLUID

(75) Inventors: Eric R. Diebold, Fishers, IN (US); Terry A. Beaty, Indianapolis, IN (US); Harvey B. Buck, Jr., Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/650,065

(22) Filed: Dec. 30, 2009

(65) Prior Publication Data

US 2010/0170807 A1 Jul. 8, 2010

Related U.S. Application Data

(60) Continuation-in-part of application No. 10/871,966, filed on Jun. 18, 2004, now Pat. No. 7,749,437, and a continuation-in-part of application No. 10/871,673, filed on Jun. 18, 2004, now Pat. No. 7,727,467, and a continuation-in-part of application No. 12/505,124, filed on Jul. 17, 2009, which is a division of application No. 12/330,757, filed on Dec. 9, 2008, now Pat. No. 7,977,112, which is a continuation of application No. 10/688,561, filed on Oct. 17, 2003, now Pat. No. 7,488,601, application No. 12/650,065, which is a continuation-in-part of application No. 11/746,465, filed on May 9, 2007, which is a continuation-in-part of application No. 10/688,312, filed on Oct. 17, 2003, now Pat. No. 7,390,667.

(60) Provisional application No. 60/480,298, filed on Jun. 20, 2003, provisional application No. 60/480,397, filed on Jun. 20, 2003.

(51) Int. Cl.
*G01N 27/00* (2006.01)
*G01N 27/06* (2006.01)

(52) U.S. Cl. .......... 436/150; 436/68; 436/149; 436/151; 422/82.01; 422/82.02

(58) Field of Classification Search .......... 436/149–151; 422/82.01–82.04
See application file for complete search history.

(56) References Cited

U.S. PATENT DOCUMENTS

| | | | |
|---|---|---|---|
| 286,735 A | 10/1883 | Rossler | |
| 672,094 A | 4/1901 | Cliffton | |
| 2,526,651 A | 8/1945 | Garbo | |
| 2,883,169 A | 4/1959 | Daman | |
| 3,526,480 A | 9/1970 | Findl et al. | |
| 3,551,295 A | 12/1970 | Dyer | |
| 3,621,381 A | 11/1971 | Eckfeldt | |
| 3,656,543 A | 4/1972 | Wolowodiuk et al. | |
| 3,661,748 A | 5/1972 | Blackmer | |
| 3,715,192 A | 2/1973 | Wenz et al. | |
| 3,720,093 A | 3/1973 | Gill | |
| 3,763,422 A | 10/1973 | MacPhee et al. | |
| 3,770,607 A | 11/1973 | Williams | |
| 3,776,832 A | 12/1973 | Oswin et al. | |
| 3,838,033 A | 9/1974 | Mindt et al. | |
| 3,870,099 A | 3/1975 | Wolowodiuk | |
| 3,902,970 A | 9/1975 | Levin | |
| 3,919,627 A | 11/1975 | Allen | |
| 3,922,598 A | 11/1975 | Steuer et al. | |
| 3,925,183 A | 12/1975 | Oswin et al. | |
| 3,937,615 A | 2/1976 | Clack et al. | |
| 3,980,437 A | 9/1976 | Kishimoto et al. | |
| 4,005,002 A | 1/1977 | Racine et al. | |
| 4,008,448 A | 2/1977 | Muggli | |
| 4,040,908 A | 8/1977 | Clark, Jr. | |
| 4,053,381 A | 10/1977 | Hamblen et al. | |
| 4,060,127 A | 11/1977 | Savin et al. | |
| 4,065,263 A | 12/1977 | Woodbridge, III | |
| 4,086,631 A | 4/1978 | Vick | |
| 4,123,701 A | 10/1978 | Josefsen et al. | |
| 4,127,448 A | 11/1978 | Schick et al. | |
| 4,184,936 A | 1/1980 | Paul et al. | |
| 4,214,968 A | 7/1980 | Battaglia et al. | |
| 4,217,196 A | 8/1980 | Huch | |
| 4,224,125 A | 9/1980 | Nakamura et al. | |
| 4,225,410 A | 9/1980 | Pace | |
| 4,230,537 A | 10/1980 | Delente et al. | |
| 4,233,029 A | 11/1980 | Columbus | |
| 4,260,680 A | 4/1981 | Muramatsu et al. | |
| 4,263,343 A | 4/1981 | Kim | |
| 4,265,250 A | 5/1981 | Parker | |
| 4,273,134 A | 6/1981 | Ricciardelli | |
| 4,273,639 A | 6/1981 | Gottermeier | |
| 4,297,569 A | 10/1981 | Flies | |
| 4,301,412 A | 11/1981 | Hill et al. | |
| 4,303,887 A | 12/1981 | Hill et al. | |
| 4,323,536 A | 4/1982 | Columbus | |
| 4,329,642 A | 5/1982 | Luthi et al. | |

(Continued)

OTHER PUBLICATIONS

US 6,517,703, 02/2003, Beaty et al. (withdrawn)

*Primary Examiner* — Lyle Alexander
(74) *Attorney, Agent, or Firm* — Woodard, Emhardt, Moriarty, McNett & Henry LLP

(57) ABSTRACT

The present disclosure relates to various methods for measuring the amount of an analyte present in a biological fluid using an electrochemical testing process. Various embodiments are disclosed, including the use of AC test signals and the performance of tests having a Total Test Time within about 2.0 seconds or less, and/or having a clinically low Total System Error.

11 Claims, 41 Drawing Sheets

U.S. PATENT DOCUMENTS

| | | |
|---|---|---|
| 4,366,033 A | 12/1982 | Richter et al. |
| 4,407,290 A | 10/1983 | Wilber |
| 4,407,959 A | 10/1983 | Tsuji et al. |
| 4,413,407 A | 11/1983 | Columbus |
| 4,413,628 A | 11/1983 | Tamulis |
| 4,420,564 A | 12/1983 | Tsuji et al. |
| 4,431,004 A | 2/1984 | Bessman et al. |
| 4,436,094 A | 3/1984 | Cerami |
| 4,440,175 A | 4/1984 | Wilkins |
| 4,476,149 A | 10/1984 | Poppe et al. |
| 4,477,314 A | 10/1984 | Richter et al. |
| 4,477,575 A | 10/1984 | Vogel et al. |
| 4,499,423 A | 2/1985 | Matthiessen |
| 4,510,383 A | 4/1985 | Ruppender |
| 4,517,291 A | 5/1985 | Seago |
| 4,545,382 A | 10/1985 | Higgins et al. |
| 4,547,735 A | 10/1985 | Kiesewetter et al. |
| 4,552,458 A | 11/1985 | Lowne |
| 4,571,292 A | 2/1986 | Liu et al. |
| 4,578,716 A | 3/1986 | Van Rijckevorsel et al. |
| 4,592,893 A | 6/1986 | Poppe et al. |
| 4,628,193 A | 12/1986 | Blum |
| 4,642,295 A | 2/1987 | Baker |
| 4,648,665 A | 3/1987 | Davis et al. |
| 4,652,830 A | 3/1987 | Brown |
| 4,654,197 A | 3/1987 | Lilja et al. |
| 4,671,288 A | 6/1987 | Gough |
| 4,676,653 A | 6/1987 | Strohmeier et al. |
| 4,679,562 A | 7/1987 | Luksha |
| 4,682,602 A | 7/1987 | Prohaska |
| 4,686,479 A | 8/1987 | Young et al. |
| 4,703,017 A | 10/1987 | Campbell et al. |
| 4,703,756 A | 11/1987 | Gough et al. |
| 4,711,245 A | 12/1987 | Higgins et al. |
| 4,713,165 A | 12/1987 | Conover et al. |
| 4,713,347 A | 12/1987 | Mitchell et al. |
| 4,714,874 A | 12/1987 | Morris et al. |
| 4,731,726 A | 3/1988 | Allen, III |
| 4,734,184 A | 3/1988 | Burleigh et al. |
| 4,750,496 A | 6/1988 | Reinhart et al. |
| 4,759,828 A | 7/1988 | Young et al. |
| 4,789,804 A | 12/1988 | Karube et al. |
| 4,795,542 A | 1/1989 | Ross et al. |
| 4,797,256 A | 1/1989 | Watlington, IV |
| 4,801,424 A | 1/1989 | Schweiger |
| 4,805,624 A | 2/1989 | Yao et al. |
| 4,806,311 A | 2/1989 | Greenquist |
| 4,806,312 A | 2/1989 | Greenquist |
| 4,810,203 A | 3/1989 | Komatsu |
| 4,812,210 A | 3/1989 | Bonivert et al. |
| 4,816,224 A | 3/1989 | Vogel et al. |
| 4,820,399 A | 4/1989 | Senda et al. |
| 4,820,636 A | 4/1989 | Hill et al. |
| 4,832,814 A | 5/1989 | Root |
| 4,834,234 A | 5/1989 | Sacherer et al. |
| 4,849,330 A | 7/1989 | Humphries et al. |
| 4,865,873 A | 9/1989 | Cole, Jr. et al. |
| 4,877,580 A | 10/1989 | Aronowitz et al. |
| 4,897,162 A | 1/1990 | Lewandowski et al. |
| 4,897,173 A | 1/1990 | Nankai et al. |
| 4,919,770 A | 4/1990 | Preidel et al. |
| 4,927,516 A | 5/1990 | Yamaguchi et al. |
| 4,929,426 A | 5/1990 | Bodai et al. |
| 4,935,105 A | 6/1990 | Churchouse |
| 4,935,106 A | 6/1990 | Liston et al. |
| 4,935,346 A | 6/1990 | Phillips et al. |
| 4,938,860 A | 7/1990 | Wogoman |
| 4,940,945 A | 7/1990 | Littlejohn et al. |
| 4,954,087 A | 9/1990 | Lauks et al. |
| 4,956,275 A | 9/1990 | Zuk et al. |
| 4,960,546 A | 10/1990 | Tharp |
| 4,963,814 A | 10/1990 | Parks |
| 4,965,051 A | 10/1990 | Shukunobe et al. |
| 4,970,145 A | 11/1990 | Bennetto et al. |
| 4,975,647 A | 12/1990 | Downer et al. |
| 4,976,724 A | 12/1990 | Nieto et al. |
| 4,999,582 A | 3/1991 | Parks et al. |
| 4,999,632 A | 3/1991 | Parks |
| 5,018,164 A | 5/1991 | Brewer et al. |
| 5,019,974 A | 5/1991 | Beckers |
| 5,035,862 A | 7/1991 | Dietze et al. |
| 5,039,618 A | 8/1991 | Stone |
| 5,049,487 A | 9/1991 | Phillips et al. |
| 5,053,199 A | 10/1991 | Keiser et al. |
| 5,059,394 A | 10/1991 | Phillips et al. |
| 5,062,458 A | 11/1991 | Rohleder et al. |
| 5,066,372 A | 11/1991 | Wetall |
| 5,075,077 A | 12/1991 | Durley, III et al. |
| 5,096,669 A | 3/1992 | Lauks et al. |
| 5,108,564 A | 4/1992 | Szuminsky et al. |
| 5,112,455 A | 5/1992 | Cozzette et al. |
| 5,112,758 A | 5/1992 | Fellman et al. |
| 5,118,183 A | 6/1992 | Cargill et al. |
| 5,120,420 A | 6/1992 | Nankai et al. |
| 5,122,244 A | 6/1992 | Hoenes et al. |
| 5,126,952 A | 6/1992 | Kildal-Brandt et al. |
| 5,128,015 A | 7/1992 | Szuminsky et al. |
| 5,141,850 A | 8/1992 | Cole et al. |
| 5,141,868 A | 8/1992 | Shanks et al. |
| 5,143,694 A | 9/1992 | Schafer et al. |
| 5,179,005 A | 1/1993 | Phillips et al. |
| 5,179,288 A | 1/1993 | Miffitt et al. |
| 5,182,707 A | 1/1993 | Cooper et al. |
| 5,185,256 A | 2/1993 | Nankai et al. |
| 5,187,100 A | 2/1993 | Matzinger et al. |
| 5,192,415 A | 3/1993 | Yoshioka et al. |
| 5,220,920 A | 6/1993 | Gharib |
| 5,232,516 A | 8/1993 | Hed |
| 5,232,667 A | 8/1993 | Hieb et al. |
| 5,232,668 A | 8/1993 | Grant et al. |
| 5,234,813 A | 8/1993 | McGeehan et al. |
| 5,243,516 A | 9/1993 | White |
| 5,246,858 A | 9/1993 | Arbuckle et al. |
| 5,250,439 A | 10/1993 | Musho et al. |
| 5,261,411 A | 11/1993 | Hughes |
| 5,264,103 A | 11/1993 | Yoshioka et al. |
| 5,266,179 A | 11/1993 | Nankai et al. |
| 5,269,891 A | 12/1993 | Colin |
| 5,272,060 A | 12/1993 | Hamamoto et al. |
| 5,279,294 A | 1/1994 | Anderson et al. |
| 5,281,395 A | 1/1994 | Markart et al. |
| 5,284,770 A | 2/1994 | Adrian et al. |
| 5,286,362 A | 2/1994 | Hoenes et al. |
| 5,288,636 A | 2/1994 | Pollmann et al. |
| 5,296,192 A | 3/1994 | Carroll et al. |
| 5,304,468 A | 4/1994 | Phillips et al. |
| 5,306,623 A | 4/1994 | Kiser et al. |
| 5,311,426 A | 5/1994 | Donohue et al. |
| 5,312,762 A | 5/1994 | Guiseppi-Elie |
| 5,324,335 A | 6/1994 | Benham et al. |
| 5,332,479 A | 7/1994 | Uenoyama et al. |
| 5,344,754 A | 9/1994 | Zweig |
| 5,352,351 A | 10/1994 | White et al. |
| 5,353,351 A | 10/1994 | Bartoli et al. |
| 5,366,609 A | 11/1994 | White et al. |
| 5,371,687 A | 12/1994 | Holmes, II et al. |
| 5,376,254 A | 12/1994 | Fisher |
| 5,379,214 A | 1/1995 | Arbuckle et al. |
| 5,384,028 A | 1/1995 | Ito |
| 5,385,846 A | 1/1995 | Kuhn et al. |
| 5,389,215 A | 2/1995 | Horiuchi et al. |
| 5,395,504 A | 3/1995 | Saurer et al. |
| 5,405,511 A | 4/1995 | White et al. |
| 5,411,647 A | 5/1995 | Johnson et al. |
| 5,413,690 A | 5/1995 | Kost et al. |
| 5,413,764 A | 5/1995 | Haar |
| 5,418,142 A | 5/1995 | Kiser et al. |
| 5,421,189 A | 6/1995 | Dussault |
| 5,424,035 A | 6/1995 | Hones et al. |
| 5,426,032 A | 6/1995 | Phillips et al. |
| 5,437,772 A | 8/1995 | De Castro et al. |
| 5,437,999 A | 8/1995 | Diebold et al. |
| 5,438,271 A | 8/1995 | White et al. |
| 5,439,826 A | 8/1995 | Kontorovich |
| 5,445,967 A | 8/1995 | Deuter |
| 5,447,837 A | 9/1995 | Urnovitz |
| 5,453,360 A | 9/1995 | Yu |

| Patent No. | Date | Inventor |
|---|---|---|
| 5,469,846 A | 11/1995 | Khan |
| 5,470,533 A | 11/1995 | Shindo et al. |
| 5,477,326 A | 12/1995 | Dosmann |
| 5,489,414 A | 2/1996 | Schreiber et al. |
| 5,494,638 A | 2/1996 | Gullick |
| 5,500,350 A | 3/1996 | Baker et al. |
| 5,504,011 A | 4/1996 | Gavin et al. |
| 5,508,171 A | 4/1996 | Walling et al. |
| 5,508,200 A | 4/1996 | Tiffany et al. |
| 5,508,203 A | 4/1996 | Fuller et al. |
| 5,509,410 A | 4/1996 | Hill et al. |
| 5,515,170 A | 5/1996 | Matzinger et al. |
| 5,515,847 A | 5/1996 | Braig et al. |
| 5,526,111 A | 6/1996 | Collins et al. |
| 5,526,120 A | 6/1996 | Jina et al. |
| 5,526,808 A | 6/1996 | Kaminsky |
| 5,527,473 A | 6/1996 | Ackerman |
| 5,532,128 A | 7/1996 | Eggers et al. |
| 5,547,702 A | 8/1996 | Gleisner |
| 5,552,116 A | 9/1996 | Yokota et al. |
| 5,554,531 A | 9/1996 | Zweig |
| 5,556,789 A | 9/1996 | Goerlach-Graw et al. |
| 5,563,031 A | 10/1996 | Yu |
| 5,563,042 A | 10/1996 | Phillips et al. |
| 5,563,863 A | 10/1996 | Hiramatsu |
| 5,569,591 A | 10/1996 | Kell et al. |
| 5,569,608 A | 10/1996 | Sommer |
| 5,572,159 A | 11/1996 | McFarland |
| 5,575,895 A | 11/1996 | Ikeda et al. |
| 5,575,930 A | 11/1996 | Tietje-Girault et al. |
| 5,576,073 A | 11/1996 | Kickelhain |
| 5,580,794 A | 12/1996 | Allen |
| 5,582,697 A | 12/1996 | Ikeda et al. |
| 5,583,432 A | 12/1996 | Barnes |
| 5,593,390 A | 1/1997 | Castellano et al. |
| 5,593,739 A | 1/1997 | Kickelhain |
| 5,594,906 A | 1/1997 | Holmes, II et al. |
| 5,597,532 A | 1/1997 | Connolly |
| 5,601,694 A | 2/1997 | Maley |
| 5,604,110 A | 2/1997 | Baker et al. |
| 5,605,662 A | 2/1997 | Heller et al. |
| 5,605,837 A | 2/1997 | Karimi et al. |
| 5,611,900 A | 3/1997 | Worden et al. |
| 5,620,579 A | 4/1997 | Genshaw et al. |
| 5,620,863 A | 4/1997 | Tomasco et al. |
| 5,627,075 A | 5/1997 | Bateson |
| 5,628,890 A | 5/1997 | Carter et al. |
| 5,630,986 A | 5/1997 | Charlton et al. |
| 5,635,362 A | 6/1997 | Levine et al. |
| 5,635,364 A | 6/1997 | Clark et al. |
| 5,639,671 A | 6/1997 | Bogart et al. |
| 5,642,734 A | 7/1997 | Ruben et al. |
| 5,645,798 A | 7/1997 | Schreiber et al. |
| 5,650,061 A | 7/1997 | Kuhr et al. |
| 5,650,062 A | 7/1997 | Ikeda et al. |
| 5,653,863 A | 8/1997 | Genshaw et al. |
| 5,654,178 A | 8/1997 | Fitzpatrick et al. |
| 5,656,502 A | 8/1997 | MacKay et al. |
| 5,658,443 A | 8/1997 | Yamamoto et al. |
| 5,658,802 A | 8/1997 | Hayes et al. |
| 5,665,215 A | 9/1997 | Bussmann et al. |
| 5,670,031 A | 9/1997 | Hintsche et al. |
| 5,677,546 A | 10/1997 | Yu |
| 5,682,884 A | 11/1997 | Hill et al. |
| 5,686,659 A | 11/1997 | Neel et al. |
| 5,691,486 A | 11/1997 | Behringer et al. |
| 5,691,633 A | 11/1997 | Liu et al. |
| 5,695,623 A | 12/1997 | Michel et al. |
| 5,698,083 A | 12/1997 | Glass |
| 5,700,695 A | 12/1997 | Yassinzadeh et al. |
| 5,708,247 A | 1/1998 | McAleer et al. |
| 5,710,622 A | 1/1998 | Neel et al. |
| 5,719,667 A | 2/1998 | Miers |
| 5,720,862 A | 2/1998 | Hamamoto et al. |
| 5,723,284 A | 3/1998 | Ye |
| 5,727,548 A | 3/1998 | Hill et al. |
| 5,728,074 A | 3/1998 | Castellano et al. |
| 5,745,308 A | 4/1998 | Spangenberg |
| 5,748,002 A | 5/1998 | Scott et al. |
| 5,753,101 A | 5/1998 | Ludwig |
| 5,757,666 A | 5/1998 | Schreiber et al. |
| 5,759,794 A | 6/1998 | Levine et al. |
| 5,762,770 A | 6/1998 | Pritchard et al. |
| 5,766,789 A | 6/1998 | James et al. |
| 5,776,710 A | 7/1998 | Levine et al. |
| 5,780,304 A | 7/1998 | Matzinger et al. |
| 5,786,584 A | 7/1998 | Button et al. |
| 5,788,833 A | 8/1998 | Lewis et al. |
| 5,789,255 A | 8/1998 | Yu |
| 5,792,668 A | 8/1998 | Deamer et al. |
| 5,798,031 A | 8/1998 | Charlton et al. |
| 5,801,057 A | 9/1998 | Smart et al. |
| 5,820,551 A | 10/1998 | Hill et al. |
| 5,820,622 A | 10/1998 | Gross et al. |
| 5,832,921 A | 11/1998 | Lennert et al. |
| 5,834,217 A | 11/1998 | Levine et al. |
| 5,837,546 A | 11/1998 | Allen et al. |
| 5,843,691 A | 12/1998 | Douglas et al. |
| 5,843,692 A | 12/1998 | Phillips et al. |
| 5,846,744 A | 12/1998 | Athey et al. |
| 5,849,174 A | 12/1998 | Sanghera et al. |
| 5,856,195 A | 1/1999 | Charlton et al. |
| 5,863,400 A | 1/1999 | Drummond et al. |
| 5,869,972 A | 2/1999 | Birch et al. |
| 5,873,990 A | 2/1999 | Wojciechowski et al. |
| 5,883,378 A | 3/1999 | Irish et al. |
| 5,885,839 A | 3/1999 | Lingane et al. |
| 5,890,489 A | 4/1999 | Elden |
| 5,897,522 A | 4/1999 | Nitzan |
| 5,904,898 A | 5/1999 | Markart |
| 5,911,872 A | 6/1999 | Lewis et al. |
| 5,916,156 A | 6/1999 | Hildenbrand et al. |
| 5,921,925 A | 7/1999 | Cartmell et al. |
| 5,922,530 A | 7/1999 | Yu |
| 5,922,591 A | 7/1999 | Anderson et al. |
| 5,925,021 A | 7/1999 | Castellano et al. |
| 5,925,293 A | 7/1999 | Howk |
| 5,945,341 A | 8/1999 | Howard, III |
| 5,948,289 A | 9/1999 | Noda et al. |
| 5,951,836 A | 9/1999 | McAleer et al. |
| 5,958,215 A | 9/1999 | Kuhr et al. |
| 5,965,380 A | 10/1999 | Heller et al. |
| 5,968,760 A | 10/1999 | Phillips et al. |
| 5,971,923 A | 10/1999 | Finger |
| 5,989,917 A | 11/1999 | McAleer et al. |
| 5,997,817 A | 12/1999 | Crismore et al. |
| 6,001,239 A | 12/1999 | Douglas et al. |
| 6,004,441 A | 12/1999 | Fujiwara et al. |
| 6,004,442 A | 12/1999 | Choulga et al. |
| 6,013,170 A | 1/2000 | Meade |
| 6,036,919 A | 3/2000 | Thym et al. |
| 6,042,714 A | 3/2000 | Lin et al. |
| 6,044,285 A | 3/2000 | Chaiken et al. |
| 6,045,567 A | 4/2000 | Taylor et al. |
| 6,061,128 A | 5/2000 | Zweig et al. |
| 6,071,391 A | 6/2000 | Gotoh et al. |
| 6,087,182 A | 7/2000 | Jeng et al. |
| 6,091,975 A | 7/2000 | Daddona et al. |
| 6,096,186 A | 8/2000 | Warburton |
| 6,102,872 A | 8/2000 | Doneen et al. |
| 6,103,033 A | 8/2000 | Say et al. |
| 6,120,676 A | 9/2000 | Heller et al. |
| 6,121,009 A | 9/2000 | Heller et al. |
| 6,121,050 A | 9/2000 | Han |
| 6,126,609 A | 10/2000 | Keith et al. |
| 6,128,519 A | 10/2000 | Say |
| 6,129,823 A | 10/2000 | Hughes et al. |
| 6,134,461 A | 10/2000 | Say et al. |
| 6,136,549 A | 10/2000 | Feistel |
| 6,136,610 A | 10/2000 | Polito et al. |
| 6,143,164 A | 11/2000 | Heller et al. |
| 6,143,247 A | 11/2000 | Sheppard, Jr. et al. |
| 6,144,869 A | 11/2000 | Berner et al. |
| 6,150,124 A | 11/2000 | Riedel |
| 6,153,069 A | 11/2000 | Pottgen et al. |
| RE36,991 E | 12/2000 | Yamamoto et al. |
| 6,156,051 A | 12/2000 | Schraga |
| 6,156,173 A | 12/2000 | Gotah et al. |

| | | | | | | |
|---|---|---|---|---|---|---|
| 6,159,745 | A | 12/2000 | Roberts et al. | 6,413,410 B1 | 7/2002 | Hodges et al. |
| 6,162,611 | A | 12/2000 | Heller et al. | 6,420,128 B1 | 7/2002 | Ouyang et al. |
| 6,162,639 | A | 12/2000 | Douglas | 6,423,218 B1 | 7/2002 | Lindermeir et al. |
| 6,168,563 | B1 | 1/2001 | Brown | 6,444,115 B1 | 9/2002 | Hodges et al. |
| 6,168,957 | B1 | 1/2001 | Matzinger et al. | 6,447,657 B1 | 9/2002 | Bhullar et al. |
| 6,170,318 | B1 | 1/2001 | Lewis | 6,454,921 B1 | 9/2002 | Hodges et al. |
| 6,174,420 | B1 | 1/2001 | Hodges et al. | 6,458,258 B2 | 10/2002 | Taniike et al. |
| 6,175,752 | B1 | 1/2001 | Say et al. | 6,461,496 B1 | 10/2002 | Feldman et al. |
| 6,176,988 | B1 | 1/2001 | Kessler | 6,475,360 B1 | 11/2002 | Hodges et al. |
| 6,179,979 | B1 | 1/2001 | Hodges et al. | 6,475,372 B1 | 11/2002 | Ohara et al. |
| 6,180,062 | B1 | 1/2001 | Naka et al. | 6,484,046 B1 | 11/2002 | Say et al. |
| 6,180,416 | B1 | 1/2001 | Kurnik et al. | 6,485,923 B1 | 11/2002 | Yani et al. |
| 6,193,873 | B1 | 2/2001 | Ohara et al. | 6,488,827 B1 | 12/2002 | Shartle |
| 6,197,040 | B1 | 3/2001 | LeVaughn et al. | 6,489,133 B2 | 12/2002 | Phillips et al. |
| 6,200,773 | B1 | 3/2001 | Ouyang et al. | 6,491,803 B1 | 12/2002 | Shen et al. |
| 6,201,607 | B1 | 3/2001 | Roth et al. | 6,491,870 B2 | 12/2002 | Patel et al. |
| 6,203,952 | B1 | 3/2001 | O'Brien et al. | 6,501,976 B1 | 12/2002 | Sohrab |
| 6,206,282 | B1 | 3/2001 | Hayes, Sr. et al. | 6,503,381 B1 | 1/2003 | Gotoh et al. |
| 6,206,292 | B1 | 3/2001 | Robertz et al. | 6,512,986 B1 | 1/2003 | Harmon |
| 6,218,571 | B1 | 4/2001 | Zheng et al. | 6,514,718 B2 | 2/2003 | Heller et al. |
| 6,225,078 | B1 | 5/2001 | Ikeda et al. | 6,514,769 B2 | 2/2003 | Lee |
| 6,226,081 | B1 | 5/2001 | Fantone et al. | 6,521,110 B1 | 2/2003 | Hodges et al. |
| 6,232,062 | B1 | 5/2001 | Kayyem et al. | 6,521,182 B1 | 2/2003 | Shartle et al. |
| 6,241,862 | B1 | 6/2001 | McAleer et al. | 6,525,330 B2 | 2/2003 | Paolini et al. |
| 6,246,330 | B1 | 6/2001 | Nielsen | 6,525,549 B1 | 2/2003 | Poellmann |
| 6,246,893 | B1 * | 6/2001 | Gobeli .................. 600/318 | 6,526,298 B1 | 2/2003 | Khalil et al. |
| 6,246,966 | B1 | 6/2001 | Perry | 6,531,040 B2 | 3/2003 | Musho et al. |
| 6,251,260 | B1 | 6/2001 | Heller et al. | 6,531,239 B2 | 3/2003 | Heller |
| 6,258,229 | B1 | 7/2001 | Winarta et al. | 6,531,322 B1 | 3/2003 | Jurik et al. |
| 6,258,254 | B1 | 7/2001 | Miyamoto et al. | 6,538,735 B1 | 3/2003 | Duebendorfer et al. |
| 6,259,937 | B1 | 7/2001 | Schulman et al. | 6,540,890 B1 | 4/2003 | Bhullar et al. |
| 6,261,519 | B1 | 7/2001 | Harding et al. | 6,540,891 B1 | 4/2003 | Stewart et al. |
| 6,262,749 | B1 | 7/2001 | Finger et al. | 6,541,266 B2 | 4/2003 | Modzelewski et al. |
| 6,268,162 | B1 | 7/2001 | Phillips et al. | 6,544,474 B2 | 4/2003 | Douglas |
| 6,270,637 | B1 | 8/2001 | Crismore et al. | 6,549,796 B2 | 4/2003 | Sohrab |
| 6,271,044 | B1 | 8/2001 | Ballerstadt et al. | 6,551,494 B1 | 4/2003 | Heller et al. |
| 6,272,364 | B1 | 8/2001 | Kurnik | 6,555,061 B1 | 4/2003 | Leong et al. |
| 6,277,641 | B1 | 8/2001 | Yager | 6,557,427 B2 | 5/2003 | Weigl et al. |
| 6,281,006 | B1 | 8/2001 | Heller et al. | 6,558,528 B1 | 5/2003 | Matzinger |
| 6,284,125 | B1 | 9/2001 | Hodges et al. | 6,560,471 B1 | 5/2003 | Heller et al. |
| 6,284,550 | B1 | 9/2001 | Carroll et al. | 6,561,978 B1 | 5/2003 | Conn et al. |
| 6,287,451 | B1 | 9/2001 | Winarta et al. | 6,561,989 B2 | 5/2003 | Whitson |
| 6,287,595 | B1 | 9/2001 | Loewy et al. | 6,562,625 B2 | 5/2003 | Modzelewski et al. |
| 6,287,875 | B1 | 9/2001 | Geisberg | 6,565,509 B1 | 5/2003 | Say et al. |
| 6,294,281 | B1 | 9/2001 | Heller | 6,565,738 B1 | 5/2003 | Henning et al. |
| 6,295,506 | B1 | 9/2001 | Heinonen et al. | 6,570,390 B2 | 5/2003 | Hirayama et al. |
| 6,299,757 | B1 | 10/2001 | Feldman et al. | 6,571,651 B1 | 6/2003 | Hodges |
| 6,300,123 | B1 | 10/2001 | Vadgama et al. | 6,572,822 B2 | 6/2003 | Jurik et al. |
| 6,300,141 | B1 | 10/2001 | Segal et al. | 6,574,425 B1 | 6/2003 | Weiss et al. |
| 6,300,142 | B1 | 10/2001 | Andrewes et al. | 6,576,101 B1 | 6/2003 | Heller et al. |
| 6,300,961 | B1 | 10/2001 | Finger et al. | 6,576,117 B1 | 6/2003 | Iketaki et al. |
| 6,309,526 | B1 | 10/2001 | Fujiwara et al. | 6,576,416 B2 | 6/2003 | Haviland et al. |
| 6,315,951 | B1 | 11/2001 | Markart | 6,576,461 B2 | 6/2003 | Heller et al. |
| 6,316,264 | B1 | 11/2001 | Corey et al. | 6,579,690 B1 | 6/2003 | Bonnecaze et al. |
| 6,325,917 | B1 | 12/2001 | Maxwell et al. | 6,591,125 B1 | 7/2003 | Buse et al. |
| 6,326,160 | B1 | 12/2001 | Dunn et al. | 6,592,744 B1 | 7/2003 | Hodges et al. |
| 6,329,161 | B1 | 12/2001 | Heller et al. | 6,592,745 B1 | 7/2003 | Feldman et al. |
| 6,330,464 | B1 | 12/2001 | Colvin, Jr. et al. | 6,594,514 B2 | 7/2003 | Berner et al. |
| 6,331,438 | B1 | 12/2001 | Aylott et al. | 6,599,406 B1 | 7/2003 | Kawanaka et al. |
| 6,333,019 | B1 | 12/2001 | Coppens | 6,599,407 B2 | 7/2003 | Taniike et al. |
| 6,335,203 | B1 | 1/2002 | Patel et al. | 6,600,997 B2 | 7/2003 | Deweese et al. |
| 6,338,790 | B1 | 1/2002 | Feldman et al. | 6,605,200 B1 | 8/2003 | Mao et al. |
| 6,340,428 | B1 | 1/2002 | Ikeda et al. | 6,605,201 B1 | 8/2003 | Mao et al. |
| 6,342,364 | B1 | 1/2002 | Watanabe et al. | 6,607,658 B1 | 8/2003 | Heller et al. |
| 6,344,490 | B1 | 2/2002 | DeGeorge et al. | 6,616,819 B1 | 9/2003 | Liamos et al. |
| 6,349,230 | B1 | 2/2002 | Kawanaka | 6,618,603 B2 | 9/2003 | Yaralli et al. |
| 6,358,752 | B1 | 3/2002 | Durst et al. | 6,618,934 B1 | 9/2003 | Feldman et al. |
| 6,377,894 | B1 | 4/2002 | Deweese et al. | 6,623,501 B2 | 9/2003 | Heller et al. |
| 6,377,896 | B1 | 4/2002 | Sato et al. | 6,627,057 B1 | 9/2003 | Bhullar et al. |
| 6,379,513 | B1 | 4/2002 | Chambers et al. | 6,632,349 B1 | 10/2003 | Hodges et al. |
| 6,389,891 | B1 | 5/2002 | D'Angelico et al. | 6,635,167 B1 | 10/2003 | Batman et al. |
| 6,391,558 | B1 | 5/2002 | Henkens et al. | 6,638,415 B1 | 10/2003 | Hodges et al. |
| 6,391,645 | B1 | 5/2002 | Huang et al. | 6,638,716 B2 | 10/2003 | Heller et al. |
| 6,394,952 | B1 | 5/2002 | Anderson et al. | 6,645,359 B1 | 11/2003 | Bhullar et al. |
| 6,395,227 | B1 | 5/2002 | Kiser et al. | 6,645,368 B1 | 11/2003 | Beaty et al. |
| 6,399,258 | B2 | 6/2002 | O'Brien et al. | 6,654,625 B1 | 11/2003 | Say et al. |
| 6,401,532 | B2 | 6/2002 | Lubbers | 6,656,702 B1 | 12/2003 | Yugawa et al. |
| 6,413,213 | B1 | 7/2002 | Essenpreis et al. | 6,660,141 B1 | 12/2003 | Minter et al. |
| 6,413,395 | B1 | 7/2002 | Bhullar et al. | 6,676,995 B2 | 1/2004 | Dick et al. |

| | | |
|---|---|---|
| 6,689,411 B2 | 2/2004 | Dick et al. |
| 6,716,620 B2 | 4/2004 | Bashir et al. |
| 6,719,887 B2 | 4/2004 | Hasegawa et al. |
| 6,723,371 B2 | 4/2004 | Chih-Lui |
| 6,740,518 B1 | 5/2004 | Duong et al. |
| 6,743,635 B2 | 6/2004 | Neel et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,776,888 B2 | 8/2004 | Yamamoto et al. |
| 6,777,243 B2 | 8/2004 | Fukuoka et al. |
| 6,787,013 B2 | 9/2004 | Chang et al. |
| 6,797,039 B2 | 9/2004 | Spencer |
| 6,800,488 B2 | 10/2004 | Khan et al. |
| 6,814,844 B2 | 11/2004 | Bhuliar et al. |
| 6,818,180 B1 | 11/2004 | Douglas et al. |
| 6,821,483 B2 | 11/2004 | Phillips et al. |
| 6,824,670 B2 | 11/2004 | Tokunaga et al. |
| 6,827,829 B2 | 12/2004 | Kawanaka et al. |
| 6,830,669 B2 | 12/2004 | Miyazaki et al. |
| 6,833,110 B2 | 12/2004 | Black |
| 6,841,389 B2 | 1/2005 | Novikov et al. |
| 6,856,125 B2 | 2/2005 | Kermani |
| 6,860,978 B2 | 3/2005 | Yamanishi et al. |
| 6,863,800 B2 | 3/2005 | Karinka |
| 6,881,322 B2 | 4/2005 | Tokunaga et al. |
| 6,881,550 B2 | 4/2005 | Phillips et al. |
| 6,881,551 B2 | 4/2005 | Heller |
| 7,018,843 B2 | 3/2006 | Heller |
| 7,022,218 B2 | 4/2006 | Taniike et al. |
| 7,041,206 B2 | 5/2006 | Gephart et al. |
| 7,050,843 B2 | 5/2006 | Shartle et al. |
| 7,390,667 B2 | 6/2008 | Burke et al. |
| 7,407,811 B2 | 8/2008 | Burke et al. |
| 7,429,865 B2 | 9/2008 | Dreibholz et al. |
| 7,488,601 B2 | 2/2009 | Burke et al. |
| 2001/0006149 A1 | 7/2001 | Taniike et al. |
| 2001/0006150 A1 | 7/2001 | Taniike et al. |
| 2001/0017269 A1 | 8/2001 | Heller et al. |
| 2001/0019831 A1 | 9/2001 | Phillips et al. |
| 2001/0028032 A1 | 10/2001 | Church et al. |
| 2001/0034068 A1 | 10/2001 | Spivey et al. |
| 2001/0039057 A1 | 11/2001 | Douglas et al. |
| 2001/0041830 A1 | 11/2001 | Varalli et al. |
| 2001/0042683 A1 | 11/2001 | Musho et al. |
| 2001/0052470 A1 | 12/2001 | Hodges et al. |
| 2001/0053535 A1 | 12/2001 | Ladisch et al. |
| 2001/0054319 A1 | 12/2001 | Heller et al. |
| 2001/0055784 A1 | 12/2001 | Noda et al. |
| 2002/0003087 A1 | 1/2002 | Chih-hui |
| 2002/0004196 A1 | 1/2002 | Whitson |
| 2002/0008038 A1 | 1/2002 | Heller et al. |
| 2002/0019707 A1 | 2/2002 | Cohen et al. |
| 2002/0023489 A1 | 2/2002 | Reimelt et al. |
| 2002/0025469 A1 | 2/2002 | Heller |
| 2002/0029058 A1 | 3/2002 | LeVaughn et al. |
| 2002/0033345 A1 | 3/2002 | Meade |
| 2002/0040850 A1 | 4/2002 | Liu et al. |
| 2002/0042090 A1 | 4/2002 | Heller et al. |
| 2002/0042558 A1* | 4/2002 | Mendelson ............ 600/323 |
| 2002/0043471 A1 | 4/2002 | Ikeda et al. |
| 2002/0044890 A1 | 4/2002 | Black |
| 2002/0053523 A1 | 5/2002 | Liamos et al. |
| 2002/0072784 A1 | 6/2002 | Sheppard et al. |
| 2002/0081588 A1 | 6/2002 | De Lumley-woodyear et al. |
| 2002/0082797 A1 | 6/2002 | Deweese et al. |
| 2002/0084184 A1 | 7/2002 | Chambers et al. |
| 2002/0084196 A1 | 7/2002 | Liamos et al. |
| 2002/0092612 A1 | 7/2002 | Davies et al. |
| 2002/0100685 A1 | 8/2002 | Huang et al. |
| 2002/0102739 A1 | 8/2002 | Nomura et al. |
| 2002/0112969 A1 | 8/2002 | Hodges et al. |
| 2002/0117404 A1 | 8/2002 | Maxwell et al. |
| 2002/0117639 A1 | 8/2002 | Paolini et al. |
| 2002/0121314 A1 | 9/2002 | Tao et al. |
| 2002/0125145 A1 | 9/2002 | Ohara et al. |
| 2002/0130042 A1 | 9/2002 | Moerman et al. |
| 2002/0130043 A1 | 9/2002 | Hodges et al. |
| 2002/0133064 A1 | 9/2002 | Ueno et al. |
| 2002/0137200 A1 | 9/2002 | Takahashi et al. |
| 2002/0137230 A1 | 9/2002 | Nadaoka et al. |
| 2002/0138275 A1 | 9/2002 | Amano et al. |
| 2002/0138356 A1 | 9/2002 | Dutta et al. |
| 2002/0139692 A1 | 10/2002 | Tokunaga et al. |
| 2002/0144895 A1 | 10/2002 | Stern et al. |
| 2002/0146835 A1 | 10/2002 | Modzelewski et al. |
| 2002/0148726 A1 | 10/2002 | Yamamoto et al. |
| 2002/0148739 A2 | 10/2002 | Liamos et al. |
| 2002/0150930 A1 | 10/2002 | Nadaoka et al. |
| 2002/0152793 A1 | 10/2002 | Sato et al. |
| 2002/0155030 A1 | 10/2002 | Matsuda et al. |
| 2002/0155615 A1 | 10/2002 | Novikov et al. |
| 2002/0157948 A2 | 10/2002 | Liamos et al. |
| 2002/0160517 A1 | 10/2002 | Modzelewski et al. |
| 2002/0164822 A1 | 11/2002 | Takahashi et al. |
| 2002/0168290 A1 | 11/2002 | Yuzhakov et al. |
| 2002/0168298 A1 | 11/2002 | Huhn et al. |
| 2002/0170823 A1 | 11/2002 | Housefield et al. |
| 2002/0175075 A1 | 11/2002 | Deng et al. |
| 2002/0175087 A1 | 11/2002 | Hodges et al. |
| 2002/0177135 A1 | 11/2002 | Doung et al. |
| 2002/0177788 A1 | 11/2002 | Hodges et al. |
| 2002/0179440 A1 | 12/2002 | Tokunaga et al. |
| 2002/0179441 A1 | 12/2002 | Yamanishi et al. |
| 2002/0179442 A1 | 12/2002 | Miyazaki et al. |
| 2002/0185385 A1 | 12/2002 | Charlton |
| 2002/0189941 A1 | 12/2002 | Katsuki |
| 2002/0192115 A1 | 12/2002 | Bhullar et al. |
| 2003/0000834 A1 | 1/2003 | Yoshioka et al. |
| 2003/0001295 A1 | 1/2003 | Okajima et al. |
| 2003/0004403 A1 | 1/2003 | Drinan et al. |
| 2003/0024811 A1 | 2/2003 | Davies et al. |
| 2003/0032875 A1 | 2/2003 | Taniike et al. |
| 2003/0036202 A1 | 2/2003 | Teodorcyzk et al. |
| 2003/0042137 A1 | 3/2003 | Mao et al. |
| 2003/0042150 A1 | 3/2003 | Ryu et al. |
| 2003/0046811 A1 | 3/2003 | Chang et al. |
| 2003/0054427 A1 | 3/2003 | Phillips et al. |
| 2003/0057132 A1 | 3/2003 | Wittenbrink et al. |
| 2003/0062263 A1 | 4/2003 | Stanford et al. |
| 2003/0064525 A1 | 4/2003 | Liess |
| 2003/0073151 A1 | 4/2003 | Phillips et al. |
| 2003/0073152 A1 | 4/2003 | Phillips et al. |
| 2003/0073153 A1 | 4/2003 | Phillips et al. |
| 2003/0079987 A1 | 5/2003 | Hodges et al. |
| 2003/0080001 A1 | 5/2003 | Hodges et al. |
| 2003/0080446 A1 | 5/2003 | Cheng |
| 2003/0087970 A1 | 5/2003 | Wittenbrink et al. |
| 2003/0088166 A1 | 5/2003 | Say et al. |
| 2003/0094383 A1 | 5/2003 | Kermani |
| 2003/0094384 A1 | 5/2003 | Vreeke et al. |
| 2003/0097981 A1 | 5/2003 | Dick et al. |
| 2003/0098233 A1 | 5/2003 | Kermani et al. |
| 2003/0098234 A1 | 5/2003 | Hasegawa et al. |
| 2003/0099773 A1 | 5/2003 | Dick et al. |
| 2003/0100030 A1 | 5/2003 | Nadaoka et al. |
| 2003/0100040 A1 | 5/2003 | Bonnecaze et al. |
| 2003/0100821 A1 | 5/2003 | Heller et al. |
| 2003/0102213 A1 | 6/2003 | Gotoh et al. |
| 2003/0106809 A1 | 6/2003 | Kermani et al. |
| 2003/0108976 A1 | 6/2003 | Braig et al. |
| 2003/0109798 A1 | 6/2003 | Kermani |
| 2003/0113907 A1 | 6/2003 | Roberts et al. |
| 2003/0132110 A1 | 7/2003 | Hasegawa et al. |
| 2003/0134347 A1 | 7/2003 | Heller et al. |
| 2003/0143113 A2 | 7/2003 | Yuzhakov et al. |
| 2003/0143116 A1 | 7/2003 | Zheng et al. |
| 2003/0143556 A1 | 7/2003 | Blackburn et al. |
| 2003/0146110 A1 | 8/2003 | Karinka et al. |
| 2003/0146436 A1 | 8/2003 | Parker et al. |
| 2003/0150724 A1 | 8/2003 | Kawanaka et al. |
| 2003/0152823 A1 | 8/2003 | Heller |
| 2003/0155237 A1 | 8/2003 | Surridge et al. |
| 2003/0155538 A1 | 8/2003 | Siepmann |
| 2003/0159944 A1 | 8/2003 | Pottgen et al. |
| 2003/0159945 A1 | 8/2003 | Miyazaki et al. |
| 2003/0164293 A1 | 9/2003 | Hodges et al. |
| 2003/0167862 A1 | 9/2003 | Hodges |

| Publication No. | Date | Inventors |
|---|---|---|
| 2003/0168338 A1 | 9/2003 | Gao et al. |
| 2003/0175841 A1 | 9/2003 | Watanabe et al. |
| 2003/0175946 A1 | 9/2003 | Tokunaga et al. |
| 2003/0176183 A1 | 9/2003 | Drucker et al. |
| 2003/0178322 A1 | 9/2003 | Iyengar et al. |
| 2003/0179914 A1 | 9/2003 | Tokunaga et al. |
| 2003/0180183 A1 | 9/2003 | Fukuoka et al. |
| 2003/0185705 A1 | 10/2003 | Otake |
| 2003/0187338 A1 | 10/2003 | Say et al. |
| 2003/0188427 A1 | 10/2003 | Say et al. |
| 2003/0190069 A1 | 10/2003 | Nikitin et al. |
| 2003/0199744 A1 | 10/2003 | Buse et al. |
| 2003/0199893 A1 | 10/2003 | Boecker et al. |
| 2003/0201194 A1 | 10/2003 | Heller et al. |
| 2003/0203498 A1 | 10/2003 | Neel et al. |
| 2003/0203503 A1 | 10/2003 | Fukuoka et al. |
| 2003/0217918 A1 | 11/2003 | Davies et al. |
| 2004/0005716 A9 | 1/2004 | Beaty et al. |
| 2004/0005721 A1 | 1/2004 | Tanike et al. |
| 2004/0016642 A1 | 1/2004 | Miyazaki et al. |
| 2004/0020777 A1 | 2/2004 | Miyamoto et al. |
| 2004/0067166 A1 | 4/2004 | Karinka et al. |
| 2004/0094432 A1 | 5/2004 | Neel et al. |
| 2004/0094433 A1 | 5/2004 | Neel et al. |
| 2004/0096928 A1 | 5/2004 | Hasegawa et al. |
| 2004/0099540 A1 | 5/2004 | Neel et al. |
| 2004/0104131 A1 | 6/2004 | Neel et al. |
| 2004/0106941 A1 | 6/2004 | Roe et al. |
| 2004/0118681 A1 | 6/2004 | Hellinga et al. |
| 2004/0123738 A1 | 7/2004 | Spencer |
| 2004/0127818 A1 | 7/2004 | Roe et al. |
| 2004/0127819 A1 | 7/2004 | Roe et al. |
| 2004/0157337 A1 | 8/2004 | Burke et al. |
| 2004/0182703 A1 | 9/2004 | Bell et al. |
| 2004/0206625 A1 | 10/2004 | Bhullar et al. |
| 2004/0235178 A1 | 11/2004 | Tokunaga et al. |
| 2004/0256248 A1 | 12/2004 | Burke et al. |
| 2004/0259180 A1 | 12/2004 | Burke et al. |
| 2004/0260511 A1 | 12/2004 | Burke et al. |
| 2005/0013731 A1 | 1/2005 | Burke et al. |
| 2005/0016844 A1 | 1/2005 | Burke et al. |
| 2005/0019212 A1 | 1/2005 | Bhullar et al. |
| 2008/0314882 A1 | 12/2008 | Bhullar et al. |

\* cited by examiner

Covariant Study
@8, 14, 24, 35, and 42°C

| Blood Glucoise (mg/dL) | Hematocrit (%) | | |
|---|---|---|---|
| | 20 | 45 | 70 |
| 50 | ✓ | ✓ | ✓ |
| 100 | ✓ | ✓ | ✓ |
| 150 | ✓ | ✓ | ✓ |
| 250 | ✓ | ✓ | ✓ |
| 300 | ✓ | ✓ | ✓ |
| 450 | ✓ | ✓ | ✓ |
| 550 | ✓ | ✓ | ✓ |

*Fig. 2*

| Block | 1 | 2 | 3 | 4 | 5 | 6 | 7 | |
|---|---|---|---|---|---|---|---|---|
| AC Frequency (kHz) DC (mV) | 10 | 10 | 20 | 2 | 1 | Open | DC=450 mV | |
| Duration (ms) | PS Data TC | PS Data TC | PS Data TC | PS Data TC | PS Data TC | PS Data TC | PS Skip DC | TC |
| | 50 300 25 | 50 100 25 | 50 100 25 | 50 100 25 | 50 100 25 | 50 100 25 | 50 100 2000 | 25 |
| Start times (ms) End Times (ms) | 50 350 | 425 525 | 600 700 | 775 875 | 950 1050 | 1125 1225 | 1300 1400 1400 3400 | |
| Output DATS | Y1 and P1 | Y2 and P2 | Y3 and P3 | Y4 and P4 | Y5 and P5 | None | DC1-DC8 | |

Note: PS=Preceeding waveform stabilization (50ms), TC=Trailing communication (25ms), Y=Admittance, P=Phase Covariant Study
@6,14,24,36,and 42°C

|  | | Hematocrit (%) | | | | |
|---|---|---|---|---|---|---|
|  | | 20 | 45 | 55 | 65 | 70 |
| Blood Glucose (mg/dL) | 30 | ✓ | ✓ | | | ✓ |
| | 60 | ✓ | ✓ | | | ✓ |
| | 90 | ✓ | ✓ | ✓ | ✓ | ✓ |
| | 250 | ✓ | ✓ | | | ✓ |
| | 400 | ✓ | ✓ | ✓ | ✓ | ✓ |
| | 600 | ✓ | ✓ | | | ✓ |

*Fig. 10*

| Reagent Thickness = ~4 μm | | | | | |
|---|---|---|---|---|---|
| Test Time (ms) | N | Bias | Precision | TSE(%) | NVAR |
| 1525 | 1597 | 0 | 5 | (10) | 4.3 |
| 1625 | 1597 | 0 | 4.8 | 9.6 | 4.1 |
| 1725 | 1597 | 0 | 4.7 | 9.3 | 4 |
| 1825 | 1597 | 0 | 4.5 | 9.1 | 3.9 |
| 1925 | 1597 | 0 | 4.4 | 8.9 | 3.8 |
| 2025 | 1597 | 0 | 4.4 | 8.8 | 3.8 |
| 2425 | 1597 | 0 | 4.5 | 9 | 3.9 |
| 3225 | 1597 | 0 | 5.3 | 10.5 | 4.6 |

| Reagent Thickness = ~2.5 μm | | | | | |
|---|---|---|---|---|---|
| Test Time (ms) | N | Bias | Precision | TSE(%) | NVAR |
| 1525 | 1636 | -0.3 | 5.4 | (11.2) | 4.6 |
| 1625 | 1636 | -0.2 | 5.1 | 10.3 | 4.3 |
| 1725 | 1636 | -0.1 | 4.9 | 10 | 4.2 |
| 1825 | 1636 | 0.0 | 4.9 | 9.9 | 4.2 |
| 1925 | 1636 | 0.0 | 5 | 10 | 4.3 |
| 2025 | 1636 | 0.0 | 5.1 | 10.2 | 4.3 |
| 2425 | 1636 | 0.0 | 5.2 | 10.5 | 4.4 |
| 3225 | 1636 | -0.1 | 5.2 | 10.6 | 4.4 |

| Reagent Thickness = ~2.0 μm | | | | | |
|---|---|---|---|---|---|
| Test Time (ms) | N | Bias | Precision | TSE(%) | NVAR |
| 1525 | 1604 | -0.7 | 6.6 | (13.9) | 5.3 |
| 1625 | 1604 | -0.6 | 6.2 | 13 | 5 |
| 1725 | 1604 | -0.5 | 5.9 | 12.4 | 4.8 |
| 1825 | 1604 | -0.4 | 5.7 | 11.8 | 4.7 |
| 1925 | 1604 | -0.2 | 5.5 | 11.3 | 4.6 |
| 2025 | 1604 | -0.2 | 5.4 | 11 | 4.5 |
| 2425 | 1604 | -0.2 | 5 | 10.1 | 4.2 |
| 3225 | 1604 | -0.1 | 4.8 | 9.6 | 4 |

*Fig. 12*

| Reference Glucose | Hematocrit (%) | Y 200 ms 1024 Hz | Y 200 ms 2048 Hz | Y 200 ms 10240 Hz | Y 200 ms 20480 Hz | Phase @200 ms 1024 Hz | Phase @200 ms 2048 Hz | Phase @200 ms 10240 Hz | Phase @200 ms 20480 Hz |
|---|---|---|---|---|---|---|---|---|---|
| 572 | 20 | 268.58 | 406.87 | 759.26 | 851.76 | 44.27 | 42.71 | 18.53 | 7.25 |
| 583 | 46 | 237.80 | 344.56 | 577.89 | 626.19 | 43.83 | 38.29 | 15.26 | 4.58 |
| 562 | 71 | 218.39 | 293.25 | 435.33 | 464.08 | 39.60 | 32.31 | 11.90 | 2.79 |
| 239 | 20 | 254.74 | 398.85 | 761.59 | 868.02 | 48.22 | 44.56 | 20.04 | 7.39 |
| 258 | 45 | 236.64 | 345.04 | 582.79 | 640.09 | 45.41 | 39.41 | 15.41 | 4.63 |
| 214 | 70 | 221.75 | 297.90 | 435.27 | 473.02 | 41.43 | 32.95 | 12.20 | 3.26 |
| 83 | 20 | 250.68 | 382.30 | 758.64 | 855.33 | 51.61 | 46.97 | 20.36 | 7.73 |
| 92 | 45 | 241.07 | 360.75 | 606.30 | 671.79 | 49.35 | 41.31 | 15.39 | 5.67 |
| 93 | 70 | 223.16 | 303.18 | 443.60 | 470.82 | 41.96 | 34.51 | 11.31 | 3.50 |

*Fig. 17A*

| Test Time | Corrected using 1,2,10,20 kHz | | | Uncorrected | | | |
|---|---|---|---|---|---|---|---|
| | 500 ms | 600 ms | 1000 ms | 1500 ms | 500 ms | 600 ms | 1000 ms | 1500 ms |
| TSE(%) | 14.20 | 10.10 | 7.40 | 7.90 | 53.80 | 52.10 | 49.60 | 49.50 |
| Bias | -0.40 | -0.20 | -0.10 | -0.10 | -7.80 | -6.50 | -5.30 | -5.40 |
| Precision | 6.90 | 4.90 | 3.60 | 3.90 | 23.00 | 22.30 | 22.10 | 22.00 |
| Nvar | 6.90 | 5.10 | 3.50 | 3.70 | 4.80 | 4.10 | 2.70 | 2.40 |

*Fig. 18*

Mulit-Sine AC Corrected @ 4 Test Times

| Test Time | Corrected using 1,2,10,20 KHz | | | | Uncorrected | | | |
|---|---|---|---|---|---|---|---|---|
| | 625 ms | 725 ms | 1025 ms | 1525 ms | 625 ms | 725 ms | 1025 ms | 1525 ms |
| TSE(%) | 10.8 | 10.2 | 10.8 | 11.7 | 48.4 | 47.5 | 46.8 | 47 |
| Bias | -0.2 | -0.2 | -0.2 | -0.3 | -3.9 | -3.9 | -4 | -4.1 |
| Precision | 5.3 | 5 | 5.3 | 5.7 | 22.3 | 21.8 | 21.4 | 21.4 |
| Nvar | 4.7 | 4.6 | 4.9 | 5.2 | 5.1 | 4.3 | 3.5 | 3.2 |

Fig. 26

Target versus Actual values [G] and % HCT

| RUN | Target [G] | PCA1 [G] | PCA2 [G] | PCA3 [G] | Average PCA [G] | CV % | Target %Hct | Actual %Hct |
|---|---|---|---|---|---|---|---|---|
| 1 | 550 | 541.1 | 541.0 | 536.7 | 539.6 | 0.5 | 20.0 | 20.5 |
| 2 | 550 | 558.9 | 558.6 | 558.4 | 558.6 | 0.1 | 45.0 | 45.0 |
| 3 | 550 | 584.6 | 586.7 | 581.9 | 584.4 | 0.4 | 70.0 | 73.5 |
| 4 | 450 | 455.6 | 459.5 | 402.8 | 439.3 | 7.2 | 20.0 | 20.0 |
| 5 | 450 | 458.1 | 458.2 | 459.6 | 458.6 | 0.2 | 45.0 | 45.0 |
| 6 | 450 | 479.9 | 480.2 | 474.8 | 478.3 | 0.6 | 70.0 | 73.0 |
| 7 | 300 | 313.5 | 309.0 | 311.2 | 311.2 | 0.7 | 20.0 | 21.0 |
| 8 | 300 | 307.2 | 307.3 | 306.0 | 306.8 | 0.2 | 45.0 | 45.0 |
| 9 | 300 | 319.1 | 325.7 | 320.3 | 321.7 | 1.1 | 70.0 | 72.5 |
| 10 | 250 | 257.8 | 258.0 | 257.2 | 257.7 | 0.2 | 20.0 | 19.0 |
| 11 | 250 | 251.9 | 263.5 | 259.2 | 258.2 | 2.3 | 45.0 | 45.0 |
| 12 | 250 | 262.9 | 268.3 | 266.7 | 265.9 | 1.0 | 70.0 | 72.0 |
| 13 | 150 | 138.9 | 137.9 | 140.6 | 139.2 | 1.0 | 20.0 | 19.0 |
| 14 | 150 | 141.0 | 140.8 | 138.8 | 140.2 | 0.9 | 45.0 | 45.0 |
| 15 | 150 | 137.8 | 137.1 | 139.4 | 138.1 | 0.9 | 70.0 | 70.0 |
| 16 | 100 | 94.6 | 94.7 | 93.3 | 94.2 | 0.8 | 20.0 | 20.0 |
| 17 | 100 | 85.1 | 89.6 | 98.6 | 91.1 | 7.6 | 45.0 | 46.0 |
| 18 | 100 | 93.6 | 92.6 | 92.2 | 92.8 | 0.8 | 70.0 | 72.0 |
| 19 | 50 | 44.4 | 44.8 | 46.0 | 45.1 | 1.9 | 20.0 | 19.0 |
| 20 | 50 | 36.9 | 36.9 | 37.5 | 37.1 | 1.0 | 45.0 | 45.0 |
| 21 | 50 | 32.1 | 33.4 | 31.9 | 32.5 | 2.4 | 70.0 | 72.0 |

Estimated vs. Measured Dry Coating Thickness, based on Coat Weight

| Coat Weight | Estimated Dry coating Film Thickness (from coating parameters) | Measured Dry Coating Film Thickness (from Dektak profilometry) |
|---|---|---|
| g/m$^2$ | µm | µm |
| 50 | 4.08 | 3.56 |
| 40 | 3.26 | 3.34 |
| 30 | 2.45 | 2.46 |
| 25 | 2.04 | 2.09 |
| 20 | 1.63 | 1.66 |

AC Admittance vs. % Hematocrit for the 30g/m$^2$ coating

| DC Test time | TSE(%) Correction with 20 and 2 KHz | TSE(%) Correction with 10 and 1 KHz |
|---|---|---|
| 900 | 7.2 | 8.0 |
| 1100 | 7.3 | 8.2 |
| 1500 | 8.6 | 9.6 |
| 2000 | 8.7 | 10.6 |
| 2500 | 8.1 | 9.7 |
| 3000 | 7.2 | 8.6 |

*FIG. 40*

SYSTEM AND METHOD FOR DETERMINING THE CONCENTRATION OF AN ANALYTE IN A SAMPLE FLUID

REFERENCE TO RELATED APPLICATIONS

This application is a continuation-in-part of U.S. Utility patent application Ser. No. 10/871,966, filed Jun. 18, 2004, now U.S. Pat. No. 7,749,437, which claims the benefit of U.S. Provisional Application No. 60/480,397, filed Jun. 20, 2003. This application is also a continuation-in-part of U.S. Utility patent application Ser. No. 10/871,673, filed Jun. 18, 2004, now U.S. Pat. No. 7,727,467, which claims the benefit of U.S. Provisional Application No. 60/332,397, filed Jun. 20, 2003. This application is also a continuation-in-part of U.S. Utility patent application Ser. No. 12/505,124, filed Jul. 17, 2009, which is a divisional of U.S. Utility patent application Ser. No. 12/330,757, filed Dec. 9, 2008, now U.S. Pat. No. 7,977,112, which is a continuation of U.S. Utility patent application Ser. No. 10/688,561, filed Oct. 17, 2003, now issued as U.S. Pat. No. 7,488,601, issued Feb. 10, 2009, which claims the benefit of U.S. Provisional Application No. 60/480,298, filed Jun. 20, 2003. This application is also a continuation-in-part of U.S. Utility patent application Ser. No. 11/746,465, filed May 9, 2007, which is a continuation-in-part of U.S. patent application Ser. No. 10/688,312, filed Oct. 17, 2003, now issued as U.S. Pat. No. 7,390,667, issued Jun. 24, 2008. The contents of these applications and patents are hereby incorporated by reference herein.

TECHNICAL FIELD OF THE INVENTION

The present invention relates to a measurement method and apparatus for use in measuring concentrations of an analyte in a fluid. The invention relates more particularly, but not exclusively, to a method and apparatus which may be used for measuring the concentration of glucose in blood.

BACKGROUND OF THE INVENTION

Measuring the concentration of substances, particularly in the presence of other, confounding substances, is important in many fields, and especially in medical diagnosis. For example, the measurement of glucose in body fluids, such as blood, is crucial to the effective treatment of diabetes.

Diabetic therapy typically involves two types of insulin treatment: basal and bolus. Basal insulin refers to continuous, e.g. time-released insulin. Bolus insulin treatment provides additional doses of faster acting insulin to regulate fluctuations in blood glucose caused by a variety of factors, including the meal-time metabolization of sugars and carbohydrates, etc. Proper regulation of blood glucose fluctuations requires accurate measurement of the concentration of glucose in the blood. Failure to do so can produce extreme complications, including blindness or impaired circulation in the extremities, which can ultimately deprive the diabetic of use of his or her fingers, hands, feet, etc.

Multiple methods are known for measuring the concentration of analytes in a blood sample, such as, for example, glucose. Such methods typically fall into one of two categories: optical methods and electrochemical methods. Optical methods generally involve reflectance or absorbance spectroscopy to observe the spectrum shift in a reagent. Such shifts are caused by a chemical reaction that produces a color change indicative of the concentration of the analyte. Electrochemical methods generally involve, alternatively, amperometric or coulometric responses indicative of the concentration of the analyte. See, for example, U.S. Pat. No. 4,233,029 to Columbus, U.S. Pat. No. 4,225,410 to Pace, U.S. Pat. No. 4,323,536 to Columbus, U.S. Pat. No. 4,008,448 to Muggli, U.S. Pat. No. 4,654,197 to Lilja et al., U.S. Pat. No. 5,108,564 to Szuminsky et al., U.S. Pat. No. 5,120,420 to Nankai et al., U.S. Pat. No. 5,128,015 to Szuminsky et al., U.S. Pat. No. 5,243,516 to White, U.S. Pat. No. 5,437,999 to Diebold et al., U.S. Pat. No. 5,288,636 to Pollmann et al., U.S. Pat. No. 5,628,890 to Carter et al., U.S. Pat. No. 5,682,884 to Hill et al., U.S. Pat. No. 5,727,548 to Hill et al., U.S. Pat. No. 5,997,817 to Crismore et al., U.S. Pat. No. 6,004,441 to Fujiwara et al., U.S. Pat. No. 4,919,770 to Priedel, et al., U.S. Pat. No. 6,054,039 to Shieh, and U.S. Pat. No. 6,645,368 to Beaty et al., which are hereby incorporated by reference in their entireties.

For the convenience of the user, reducing the time required to display an indication of the glucose level in a blood sample has been a goal of system designers for many years. Test times have been reduced from early colorimetric products that took approximately two minutes to display a reading, to test times on the order of 20-40 seconds. More recently, test times shorter than ten seconds have been described (see, for example, U.S. Pat. Nos. 7,276,146 and 7,276,147), and several products currently on the market advertise test times of about five seconds. Shorter test times of less than two seconds have been discussed in various patent applications (see, for example, U.S. Patent Application Publication Nos. 2003/0116447A1 and 2004/0031682A1). But the true utility of a short test time is not completely reached with these teachings in terms of the results being substantially unaffected by confounding interferents.

An important limitation of electrochemical methods for measuring the concentration of a chemical in blood is the effect of confounding variables on the diffusion of analyte and the various active ingredients of the reagent. Examples of limitations to the accuracy of blood glucose measurements include variations in blood composition or state (other than the aspect being measured). For example, variations in hematocrit (concentration of red blood cells), or in the concentration of other chemicals in the blood, can effect the signal generation of a blood sample. Variations in the temperature of the blood samples is yet another example of a confounding variable in measuring blood chemistry. The utility of a reported blood glucose response after a short test time is questionable in applications where the results are not compensated for other sample variables or interferents such as hematocrit and temperature.

With respect to hematocrit in blood samples, prior art methods have relied upon the separation of the red blood cells from the plasma in the sample, by means of glass fiber filters or with reagent films that contain pore-formers that allow only plasma to enter the films, for example. Separation of red blood cells with a glass fiber filter increases the size of the blood sample required for the measurement, which is contrary to test meter customer expectations. Porous films are only partially effective in reducing the hematocrit effect, and must be used in combination with increased delay time and/or AC measurements (see below) to achieve the desired accuracy.

Prior art methods have also attempted to reduce or eliminate hematocrit interference by using DC measurements that include longer incubation time of the sample upon the test strip reagent, thereby reducing the magnitude of the effect of sample hematocrit on the measured glucose values. Such methods also suffer from greatly increased test times.

Other attempts to reduce or eliminate hematocrit and temperature interference are taught in U.S. Pat. No. 7,407,811, as well as in the disclosures of the parent cases to this application, in which an AC potential of a low amplitude is applied to a sample in order to determine certain sample characteristics based on phase angle (also referred to herein as "phase") and admittance information from the current response to the AC excitation signal. As it is taught, multiple frequencies of an AC excitation signal are applied in sequential blocks, followed by a conventional DC excitation signal. However, those disclosures indicate the inventors' belief that there are limits to the minimum time each frequency must be applied in order to obtain useful, consistent and reasonably reproducible information, from both the AC and DC excitation signals. Even then, the shortest total test time practically achievable from a complete AC method was 3 seconds. Alternatively, to achieve a practical analysis in less than 3 seconds, a limit was placed on the number of frequency blocks used during the AC excitation, i.e. 2 blocks rather than 4. However, reducing the number of frequency blocks used may have a negative affect on the level of accuracy attainable in correcting for multiple interferents, e.g., hematocrit and temperature. As has been taught in these previous disclosures of AC excitation, correction of the indicated glucose can be achieved for multiple interferents by obtaining multiple correction factors, such as the phase and/or admittance response data resulting from multiple frequencies of an AC signal excitation. Multiple correction factors are particularly beneficial when they measure individual or different aspects of interferents or when they are influenced by one interferent more than the other.

Furthermore, the correction factors or even the measurements used for determining the desired analyte concentration may also be used for calculating and optionally reporting additional parameters such as the hematocrit level or hematocrit range of the blood. By reducing the number of potential correction factors, e.g. measuring the phase and/or admittance from only two rather than three, four or more frequencies of an AC excitation, potentially useful information could be forsaken. Information such as hematocrit level or hematocrit range, for example, could be useful information for a user, especially for health care providers in a clinical setting where patients who are more susceptible to medically significant abnormal hematocrits due to illness or treatment could be identified during a routine blood glucose test. Providing a hematocrit level, for example, in addition to the glucose concentration would be a valuable piece of information in some settings, which could be lost as a result of the solutions presented by the prior art.

Thus, a system and method are needed that more accurately measure blood glucose, even in the presence of confounding variables, including variations in hematocrit, temperature and the concentrations of other chemicals in the blood. Further needed are such system and method with test times of less than 2 seconds. A system and method are likewise needed that accurately measure any medically significant component of any biological fluid with test times of less than 2 seconds. It is an object of the present invention to provide such a system and method.

SUMMARY OF THE DISCLOSED EMBODIMENTS

In one embodiment, a method for determining a concentration of a medically significant component of a biological fluid is disclosed, comprising the steps of: applying a first signal having an AC component to the biological fluid; measuring a first current response to the first signal; applying a second signal comprising a DC signal to the biological fluid; measuring a second current response to the second signal; combining the first and second responses; and determining an indication of the concentration of the medically significant component. In other embodiments, the time for completing the steps is no more than about 2 seconds. In yet other embodiments, the Total System Error from the method is no more than about 10%. In yet other embodiments, the first signal comprises an AC signal comprising a multi-frequency excitation waveform wherein different AC frequencies are generally simultaneously applied rather than sequentially applied in order to minimize the time for completing application of the first and second signals.

Other embodiments of a system and method will be understood from the description herein and as set forth in the claims appended hereto.

BRIEF DESCRIPTION OF THE DRAWINGS

The invention will be further described, by way of example only, with reference to the accompanying drawings, in which:

FIG. 2 is a table showing the glucose, hematocrit and temperature levels used in a first covariate study described herein.

FIG. 10 is a table showing the glucose, hematocrit and temperature levels of whole blood samples used in a first study described herein.

FIG. 12 is a table showing the measurement performance of three reagent thicknesses used in a second study described herein.

FIG. 17A is a table of 200 ms admittance and phase response data for a third covariate blood glucose measurement study obtained using the methods disclosed herein.

FIG. 18 is a table showing both uncorrected blood glucose measurement evaluations at several test times, as well as measurement evaluations for the same data corrected using the methods disclosed herein, in a third study described herein.

FIG. 26 is a table showing target versus actual values for the results of the fourth covariate study described herein.

FIG. 40 is a table showing TSE for corrected responses at the different DC test times corrected according to the fifth study described herein.

DETAILED DESCRIPTION OF THE VARIOUS EMBODIMENTS

Figure 1:
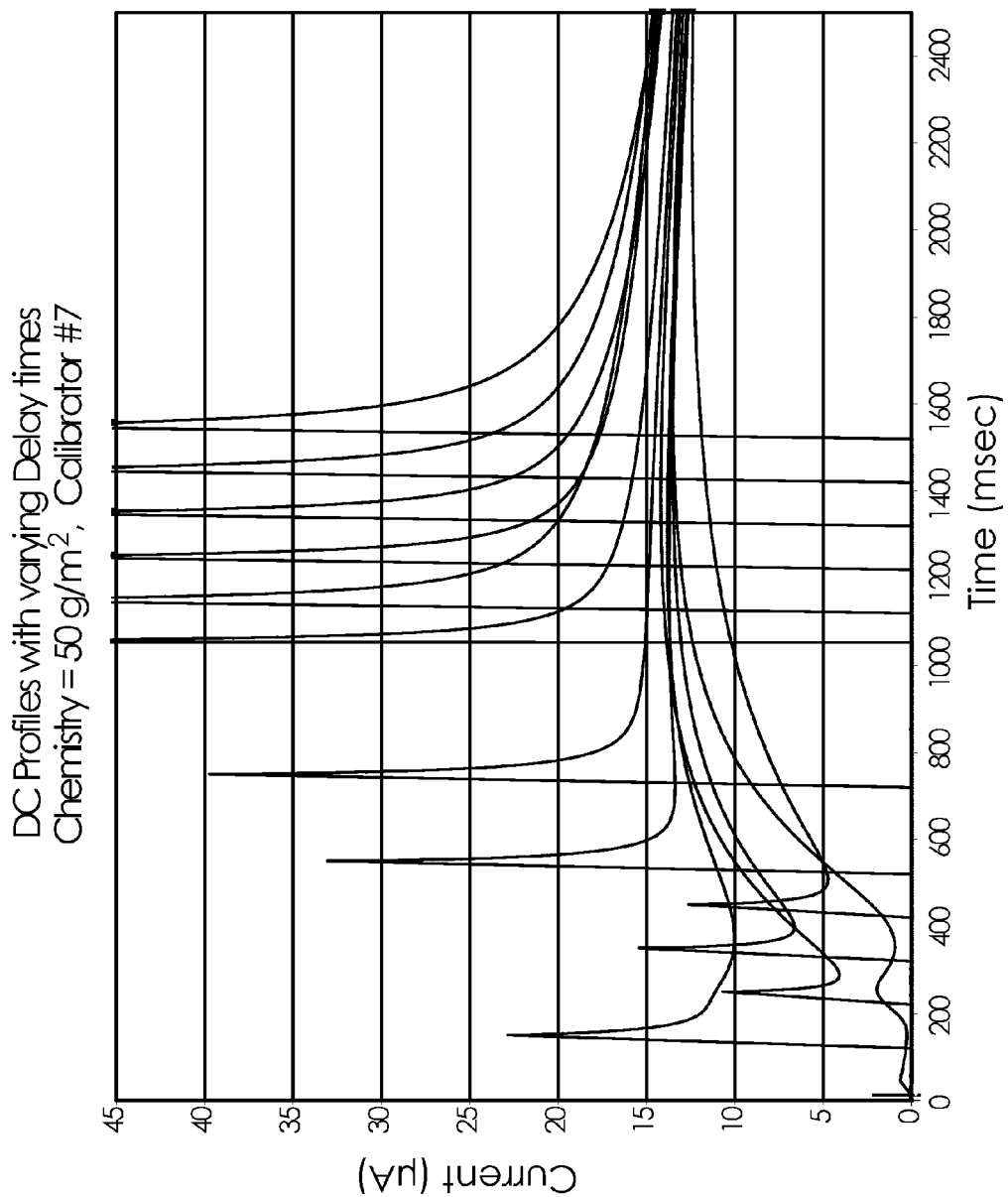
FIG. 1 is a plot of current versus time for measurements using a biosensor having a reagent layer thickness of about 3.6 μm, parameterized for time between sample application and application of the DC excitation.

For the purposes of promoting an understanding of the principles of the invention, reference will now be made to the embodiments illustrated in the drawings, and specific language will be used to describe those embodiments. It will nevertheless be understood that no limitation of the scope of the invention is intended. Alterations and modifications in the illustrated device, and further applications of the principles of the invention as illustrated therein, as would normally occur to one skilled in the art to which the invention relates are contemplated and are desired to be protected. In particular, although the invention is discussed in terms of a blood glucose test device and measurement methods, it is contemplated that the invention can be used with devices for measuring other analytes and other sample types. Such alternative embodiments require certain adaptations to the embodiments discussed herein that would be obvious to those skilled in the art.

A system and method according to the present invention permit the accurate measurement of an analyte in a fluid in an ultra-fast test time, namely no more than about 2 seconds. In particular, the measurement of the analyte remains accurate despite the presence of interferents, which would otherwise cause error. For example, a blood glucose meter according to the present invention measures the concentration of blood glucose within whole blood samples without error that is typically caused by variations in the hematocrit level of the sample and the temperature of the sample. The accurate measurement of blood glucose is invaluable to the prevention of blindness, loss of circulation, and other complications of inadequate regulation of blood glucose in diabetics. An additional advantage of a system and method according to the present invention is that measurements can be made much more rapidly and with much smaller sample volumes, making it more convenient for the diabetic person to measure their blood glucose. Likewise, accurate and rapid measurement of other analytes in blood, urine, or other biological fluids provides for improved diagnosis and treatment of a wide range of medical conditions.

It will be appreciated that electrochemical blood glucose meters typically (but not always) measure the electrochemical response of a blood sample in the presence of a reagent. The reagent reacts with the glucose to produce charge carriers that are not otherwise present in blood. Consequently, the electrochemical response of the blood in the presence of a given signal is intended to be primarily dependent upon the concentration of blood glucose. Secondarily, however, the electrochemical response of the blood to a given signal may be dependent upon other factors, including hematocrit and temperature. See, for example, U.S. Pat. Nos. 5,243,516; 5,288,636; 5,352,351; 5,385,846; and 5,508,171, which discuss the confounding effects of hematocrit on the measurement of blood glucose, and which are hereby incorporated by reference in their entireties. In addition, certain other chemicals can influence the transfer of charge carriers through a blood sample, including, for example, uric acid, bilirubin, and oxygen, thereby causing error in the measurement of glucose.

The various embodiments disclosed herein relate to systems and methods that allow shorter test times to be achieved, while still delivering an analyte measurement (be it blood glucose or another fluid sample analyte) corrected for confounding interferents (be they hematocrit and temperature, or other interferents). Test times of less than two seconds, including times less than one second, are enabled by the systems and methods disclosed herein. As used herein, "Total Test Time" is defined as the length of time from sample detection (or sample dose sufficiency, if both are detected) when a first electrical signal is to be applied to the sample, to the taking of the last measurement used in the concentration determination calculations.

In addition to shorter Total Test Times, the embodiments disclosed herein result in analyte measurements having lower Total System Error, or "TSE". TSE generally comprises a combined measure of accuracy and precision of a system or method. It is typically calculated as (Absolute Bias)+2*(Precision), where Bias=Average of Normalized Error; Precision=StdDev(Normalized Error). Normalized Error is typically calculated relative to a standard reference value. For example, in the context of a blood glucose measurement, Normalized Error=(Predicted glucose−Reference glucose) for a Reference glucose sample less than or equal to 75 mg/dl; but Normalized Error=(Predicted glucose−Reference glucose)*100/(Reference glucose) for a Reference glucose sample greater than 75 mg/dl.

As used herein, the phrase "a signal having an AC component" refers to a signal which has some alternating potential (voltage) portions. For example, the signal may be an "AC signal" having 100% alternating potential (voltage) and no DC portions; the signal may have AC and DC portions separated in time; or the signal may be AC with a DC offset (AC and DC signals superimposed). In the latter instance, the signal may still be described as having an AC component even though the polarity of the variable potential does not alternate.

Examples 1 and 2 describe details of experiments in which Total Test Time was reduced. In each example, an AC block is used in order to generate correction data to be combined algorithmically with a DC measurement, similar to the known measurement sequence utilized in the ACCU-CHEK® Aviva meter. That is, multiple AC potential frequencies are applied in a sequential fashion with current response and other measurement data determined for each frequency. However, in Examples 1 and 2, the Total Test Time is reduced by reducing the time for each sequential AC frequency block, as well as the time for the DC block. Example 1 details an experiment using these condensed time blocks in a covariate study, using a biosensor with a common reagent layer thickness. Example 2 details an experiment with the condensed times in a covariate study using biosensors having variable reagent layer thicknesses.

Measurement sequences for Examples 1 and 2 were conducted using an in-house data acquisition test stand (DATS potentiostat) comprising a bank of blood glucose meters configured as a multi-meter test stand using a modified code key to program desired measurement parameters. Although the meters could be programmed or configured with a variety of methods and durations for a test sequence, there were a few limitations, such as the choice of frequencies available pre-programmed in the meter hardware. This in-house test stand will be hereinafter referred to as the "DATS".

Certain embodiments of the present invention disclosed herein generally utilize the collection of AC test data at multiple frequencies over a shorter time period by using multi-frequency excitation waveform techniques. Examples 3 and 4 describe the details of experiments in which multi-frequency excitation waveforms were used. These multi-frequency excitation waveforms are formed by adding a plurality of individual waveforms of varying frequency together so that the fluid sample is excited by multiple frequencies at the same time. Multi-frequency excitation waveforms allow not only short measurement times, but also adaptive measurement sequences, because AC signal data collection does not permanently alter the sensed chemistry in the way that a DC measurement does because of the alternating polarity of the applied excitation. Moreover, the additional frequencies of the AC signals are applied at low excitation AC potentials, per the methods disclosed in co-pending published U.S. patent applications US-2004-0157339-A1, US-2004-0157337-A1, 2004/0157338-A1, US-2004-0260511-A1, US-2004-0256248-A1 and US-2004-0259180-A1, in order to generate a non-faradaic current response from which a phase angle provides an indication of certain interfering factors, from which indication a determination of one or more interferent corrections can be made and used for more accurately determining the analyte concentration in the fluid sample.

The resulting sample response can then be measured and the contribution from each excitation frequency component can be deduced by use of Fourier Transform techniques, such as a Discrete Fourier Transform (DFT). Although the various examples disclosed herein utilize multi-sine excitation waveforms, those skilled in the art will recognize that the multi-frequency waveform may be constructed using individual waveforms having any desired shape, such as triangular, square, sawtooth, delta, etc., just to name a few non-limiting examples. The component AC waveforms used to create the multi-frequency waveform may each have any desired frequency and any desired amplitude. The use of multi-frequency techniques not only shortens the time necessary to collect the desired data (since the AC measurements are made simultaneously rather than sequentially), but also correlates better for correction since the sample is varying less during the data collection corresponding to each applied frequency. Also, the AC measurement can be made closer in time to the DC measurement. Better correlation between the state of the sample during the respective AC and DC measurements allows for better interferent compensation even if the sample is not in steady state.

Measurements for Examples 3 and 4 were conducted with an electrochemical test stand constructed on the basis of VXI components from Agilent, and programmable to apply AC and DC potentials to sensors in requested combinations and sequences and to measure the resulting current responses of the sensors. Data were transferred from the electrochemical analyzer to a desktop computer for analysis using Microsoft® Excel®. The measurements could be carried out by any commercially available programmable potentiostat with an appropriate frequency response analyzer and digital signal acquisition system. For commercial use, the method can be carried out in a dedicated low-cost hand-held measurement device, such as the ACCU-CHEK® AVIVA™ blood glucose meter, in which the firmware is configured to enable application of AC signals in a multi-frequency waveform. In such a case the measurement parameters may be contained in or provided to the firmware of the meter, and the measurement sequence and data evaluation executed automatically with no user interaction. For example, using a programmable potentiostat as described above, measurements were conducted and results analyzed in a manner such that Total Test Times of less than 2 seconds after the analyte-containing sample was applied to a biosensor and detected by the equipment are possible. Similarly, the firmware of the ACCU-CHEK® AVIVA™ blood glucose meter may be provided with measurement parameters configured and arranged to cause the measurement sequence to occur within the same time periods, namely Total Test Times of less than 2 seconds after the analyte-containing sample is applied to a biosensor and detected by the meter. The measurement result may be displayed on the digital display of the meter when the evaluation of the measurement data is complete, typically 25-50 ms after the last measurement is taken.

EXAMPLE 1

Sequential Multiple AC Frequency Test with Fast Total Test Time

U.S. Pat. No. 7,407,811 teaches use of sequentially applied multiple frequency AC blocks followed by a DC block. For example, Example 5 described in U.S. Pat. No. 7,407,811 utilizes sequential applications of AC excitation followed by a DC excitation. The excitation signal comprised a 10 kHz AC signal applied for approximately 1.8 seconds, a 20 kHz AC signal applied for approximately 0.2 seconds, a 2 kHz AC signal applied for approximately 0.2 seconds, a 1 kHz AC signal applied for approximately 0.2 seconds, and a DC signal applied for approximately 0.5 seconds. The Total Test Time was 3.0 seconds.

Figure 24:
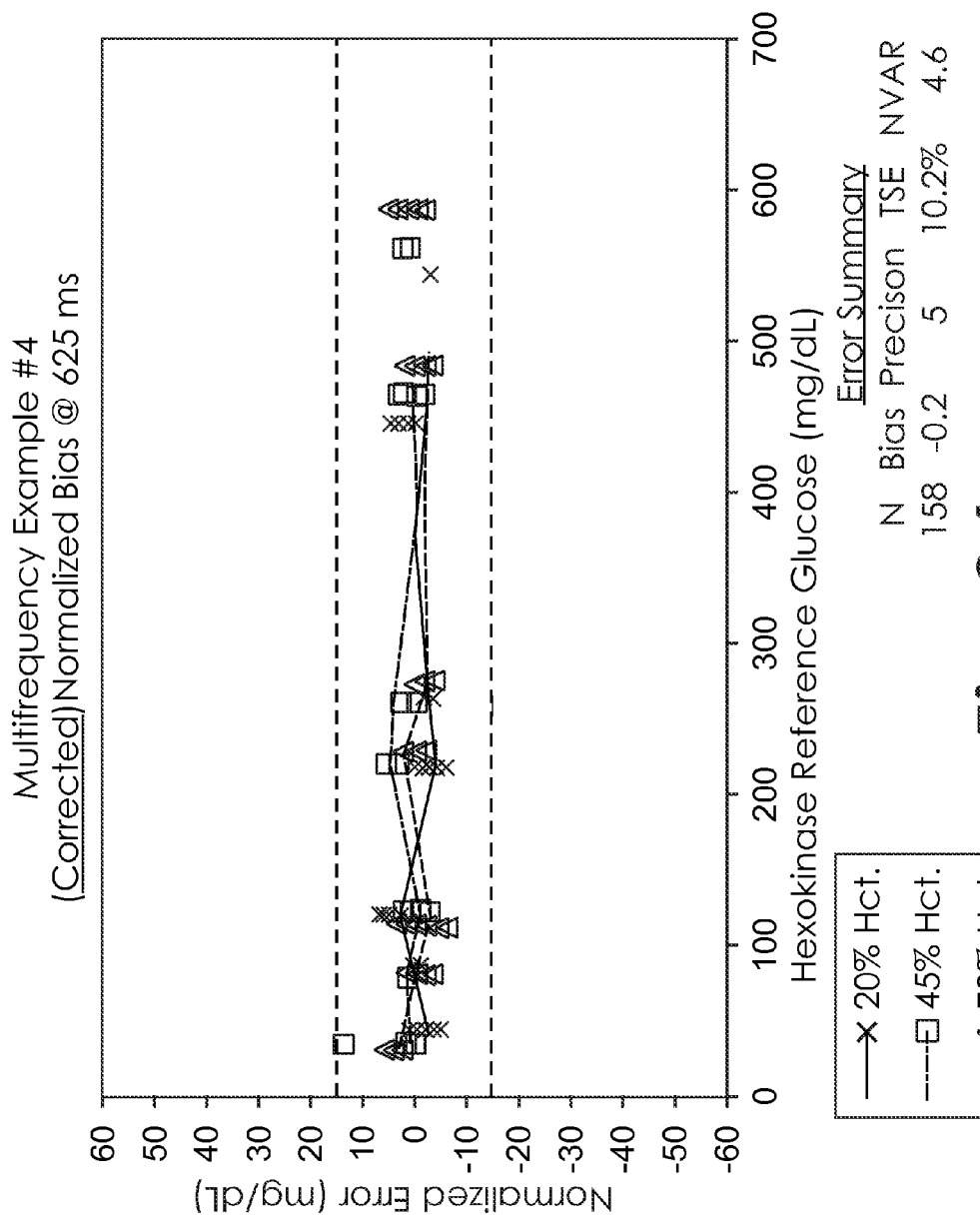
FIG. 24 is a graph of normalized error versus reference glucose for the data of FIG. 23 corrected using the methods disclosed herein.

In Example 6 of that same patent, it was desired to obtain Total Test Times as low as 1.1 seconds using the same test strip design that was used for Example 5 in that patent. In order to achieve this, the inventors did not believe that they could simply apply the sequential excitations of Example 5 for shorter periods of time. As stated in the patent:

"Using the same test strip 1700 and reagent described above for Example 5, the excitation profile illustrated in FIG. 24 was utilized in order to decrease the Total Test Time. As described above with respect to Example 5, it was determined that the phase angle at 20 kHz and at 10 kHz were most closely correlated with the hematocrit estimation. It was therefore decided to limit the AC portion of the excitation to these two frequencies in Example 6 in order to decrease the Total Test Time. In order to make further reductions in Total Test Time, the 10 kHz AC excitation was applied simultaneously with the DC signal (i.e. an AC signal with a DC offset), the theory being that this combined mode would allow for the collection of simultaneous results for DC current, AC phase and AC admittance, providing the fastest possible results. Therefore, the 20 kHz signal was applied for 0.9 seconds. Thereafter, the 10 kHz and DC signals were applied simultaneously for 1.0 second after a 0.1 second interval."

(U.S. Pat. No. 7,407,811, col. 23, ll. 23-40). The inventors of U.S. Pat. No. 7,407,811 therefore believed that in order to shorten the Total Test Time below 3.0 seconds, they needed to remove two of the AC excitation blocks (those at 2 kHz and 1 kHz) and apply one of the remaining two AC excitation blocks concurrently with the DC excitation.

Figure 7:
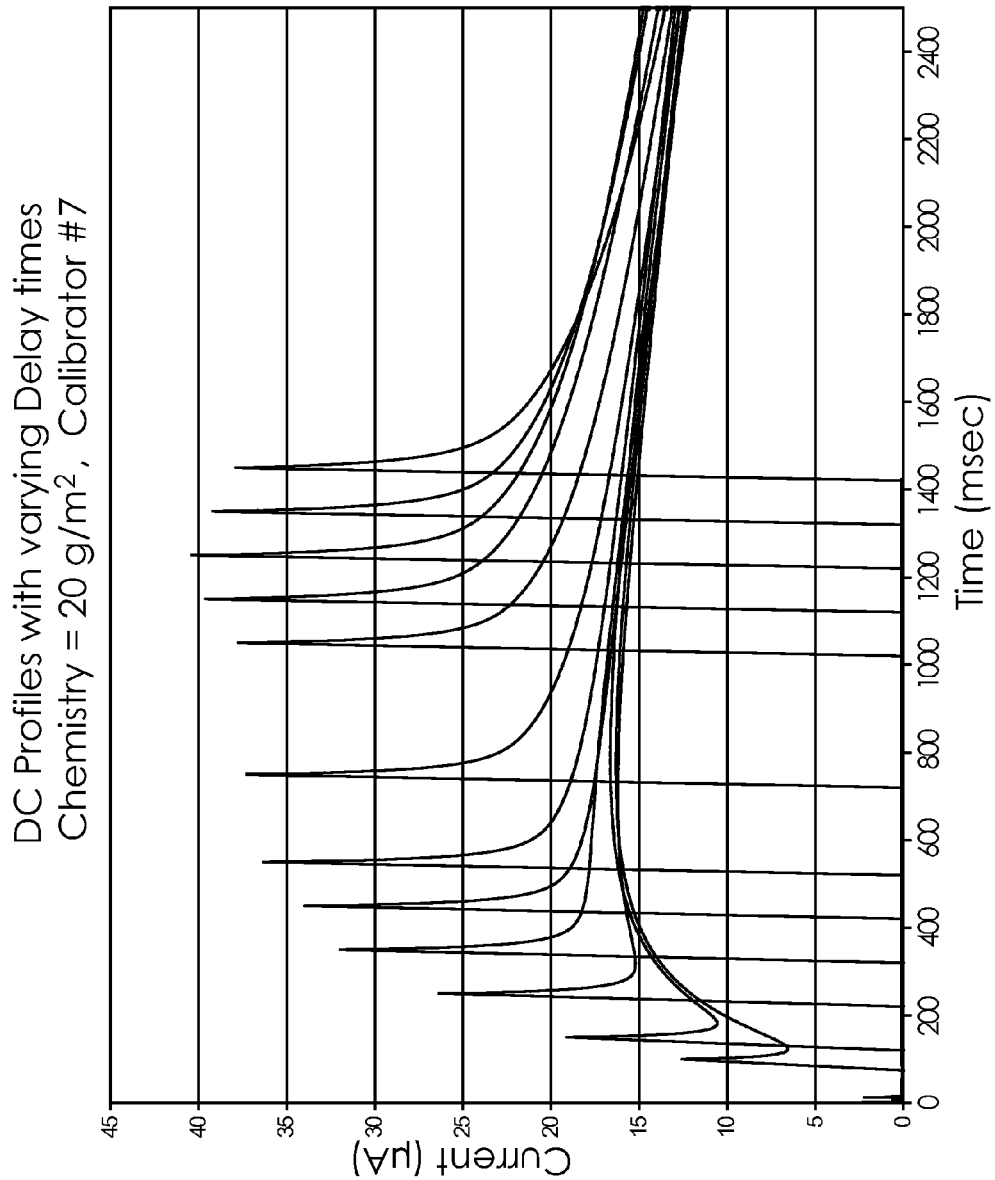
FIG. 7 is a plot of current versus time for measurements using a biosensor having a reagent layer thickness of about 1.6 μm, parameterized for time between sample application and application of the DC excitation.

One reason for this belief in the prior art is illustrated in FIGS. 1 and 7, where the measured DC response of a sample applied to the reagent chemistry is shown for various tests where the timing of the application of the DC excitation signal after sample application is varied. It can be seen that when the DC excitation is applied very quickly after sample application, the response does not exhibit the expected Cottrellian decay, thereby making accurate determinations of the sample glucose concentration impossible for fast test times. This is because enzyme and mediator availability, hydration, and diffusion within the reagent layer limit how soon the DC measurement can be made in a reproducible fashion. Reagent hydration and coating uniformity from sensor to sensor is a significant factor in how fast the DC response can be measured.

We have found that shorter AC times are possible because information to correlate with interferences such as hematocrit is presented in the AC response data even at early times. Although there is some stabilization of AC over the first few 100 ms, the signals for AC even at short times correlate well with the hematocrit interference. Using information for all desired frequencies gathered at the same interval from the desired glucose DC response enables good correlation or correction of the DC glucose response with the AC measured hematocrit interference.

The present Example 1 was conducted to demonstrate the feasibility of running the prior art sequential multiple AC frequency test methodology at a faster rate using sensors slot die coated with a uniform reagent formulation containing glucose oxidase. (Slot die coating of uniform reagents are described in U.S. Patent Application Publication No. 2005/0008537, which is incorporated herein by reference in its entirety). The sensor electrodes were made by the process of gold sputtering (~50 ηm) onto Melinex 329 followed by laser ablation through a chrome-on-quartz mask to form the pattern of the conductive layer to define the working and dose sufficiency electrodes. The structures used were similar to that shown in U.S. Pat. No. 7,407,811, at FIG. 33. The electrodes included a pair of dose sufficiency electrodes independent of a pair of measurement electrodes. Measurements were made using the DATS. A benefit of the DATS configuration is the ease of setup and fast, multi-channel data collection in environmental chambers at different temperatures. Using a DATS comprising existing meters configured for use with AC excitation measurement methods did present some limitations in terms of programmability including specific transition times required between blocks and also the available AC frequencies, essentially all basic, non-programmable aspects of the meters used with the DATS. However, using such existing meters was useful in that the sequential multiple AC frequency method examined in Example 1 (and in Example 2, below) could be backwardly compatible for use with the existing meters.

A covariate study was performed with whole blood samples having seven different glucose target concentrations (50, 100, 150, 250, 300, 450 and 550 mg/dL), three different hematocrit target concentrations (25%, 45% and 70%) and five different temperatures (8, 14, 24, 35 and 42 degrees C.). The table of FIG. 2 details the whole blood sample compositions used for this Example 1.

AC data was collected using sequentially applied AC excitation signals of 10 kHz, 20 kHz, 2 kHz and 1 kHz at 9 mV RMS. Then, after a 100 ms open circuit, a DC potential of 450 mV was applied starting at 1300 ms. DC measurement data was collected every 100 ms starting at 1400 ms, and the 1525 ms DC data point was analyzed in this Example 1 (i.e. the tests utilized a Total Test Time of 1.525 seconds). (DC data points were taken at times later than the Total Test Time in order to confirm the viability of the shorter Total Test Time. Because the viability of a Total Test Time at, e.g., 1.525 seconds or less was confirmed, the DC data points at longer times were not used for calculating final results.) The table of FIG. 3 tabulates the excitation signal composition and timing, while this data is presented graphically in a general way in FIG. 4.

Figure 5:
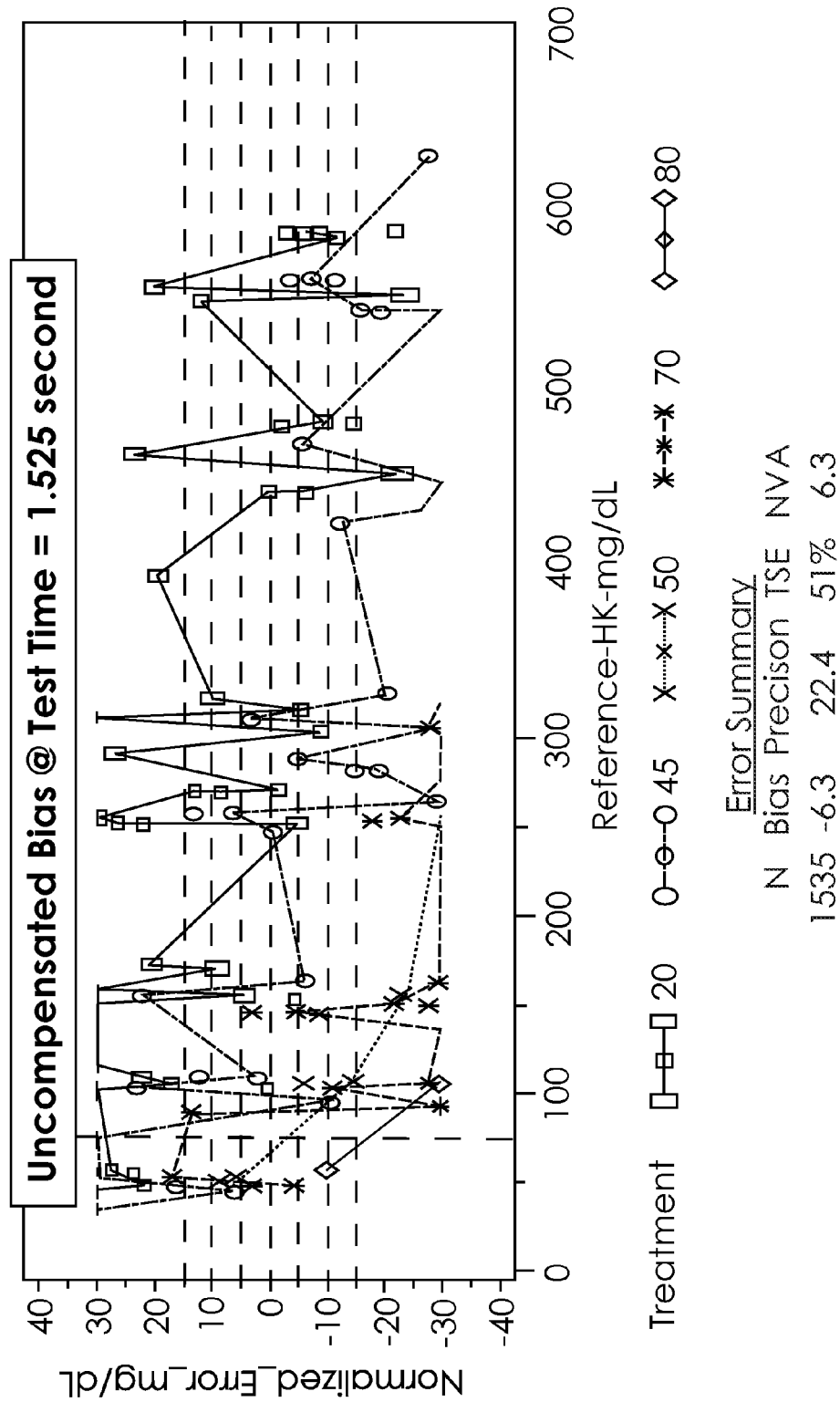
FIG. 5 is a graph of normalized error versus reference glucose for uncorrected measurement data from a first study described herein.

FIG. 5 plots the normalized error versus the reference glucose for approximately 1600 data points for all 105 covariant samples ([G], % HCT, ° C.), using only the uncorrected DC measurement taken at 1525 ms. Determining the predicted glucose from the DC measurement was performed using well known prior art techniques. As will be readily apparent to those skilled in the art, the performance of the measurement system with such a short DC-only test time is extremely poor, with a Total System Error of 51%.

Figures 3, 4:
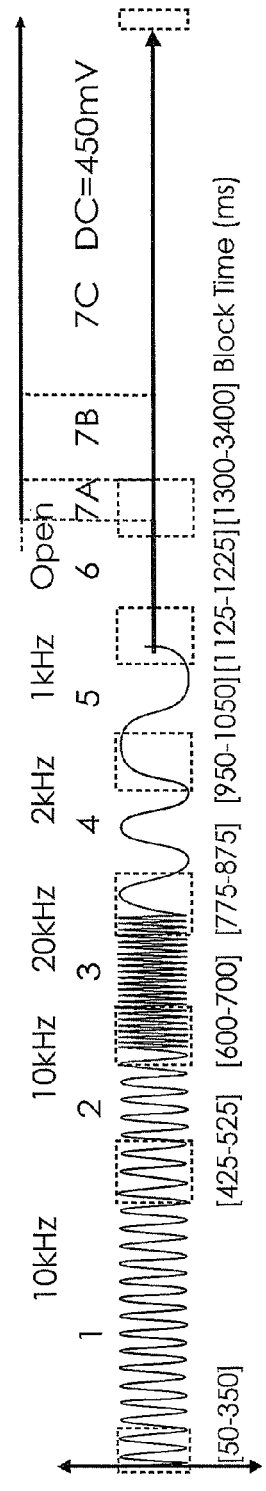
FIG. 3 tabularly illustrates the excitation signal profile and timing for a first study described herein.
FIG. 4 graphically illustrates the excitation signal profile and timing for a first study described herein.

As shown in FIGS. 3 and 4, the AC excitation potentials (1 through 5) for this Example 1 were applied sequentially. The sequence described was started after a 10 kHz signal was first applied (not shown) to detect sample application (dose detection) and the filling of the capillary test chamber (sample sufficiency) determination. The use of AC measurements for drop detect and dose sufficiency is described in U.S. Pat. No. 7,597,793, which is hereby incorporated herein by reference.

After the sample sufficiency determination, a 300 ms 10 kHz block was applied for AC stabilization, followed by four additional AC data blocks each of 100 ms duration at 10 kHz, 20 kHz, 2 kHz and 1 kHz signals. All times herein are started in relation to detection of sample dose sufficiency. Furthermore, Block 1 was kept in the sequence of FIG. 3 mainly for backward compatibility to an ACCU-CHEK® AVIVA™-related meter failsafe, which is not relevant to the present invention. In addition, Block 1 was used to stabilize the AC prior to the next block at the same frequency. One of the goals of some of this work was to show a backwards compatible short test time for the product platform of ACCU-CHEK® AVIVA™ meters. Additional experiments were conducted with only two frequencies to examine the limits of the effectiveness of correction in sequential AC/DC vs. test time. See, e.g. FIG. 8.

After the AC measurements, the measurement electrodes were then held at an open circuit for 100 ms, followed by application of a 450 mV DC signal. Between each excitation block, there was a 75 ms delay consisting of a 50 ms pre-stabilization and a 25 ms trailing data communication period. Test times were evaluated at 1525 ms (Test Time=1.525 seconds uses DC at 1.5 sec+0.025 s communication time)

AC admittance values were captured for each of the four 100 ms AC excitation blocks in order to correct the DC glucose measurement for the interfering effects of hematocrit and temperature using the following equation:

$$\text{Predicted Glucose}=INT+Y_{i2}*Y_2+P_{i2}*P_2+Y_{i3}*Y_3+P_{i3}*P_3+Y_{i4}*Y_4+P_{i4}*P_4+Y_{i5}*Y_5+P_{i5}*P_5+\exp(SLOPE+Y_{s2}*Y_2+P_{s2}*P_2+Y_{s3}*Y_3+P_{s3}*P_3+Y_{s4}*Y_4+P_{s4}*P_4+Y_{s5}*Y_5+P_{s5}*P_5)*DC**POWER \quad \text{(equation 1)}$$

where: Yi2, Yi3, Yi4, Yi5, Ys2, Ys3, Ys4 and Ys5 are constants

Pi2, Pi3, Pi4, Pi5, Ps2, Ps3, Ps4 and Ps5 are constants

Y2 is the admittance magnitude at 10 kHz (second block)

Y3 is the admittance magnitude at 20 kHz

Y4 is the admittance magnitude at 2 kHz

Y5 is the admittance magnitude at 1 kHz

P2 is the phase angle at 10 kHz (second block)

P3 is the phase angle at 20 kHz

P4 is the phase angle at 2 kHz

P5 is the phase angle at 1 kHz

INT is the intercept

SLOPE is the slope

DC is the uncorrected glucose response predicted with the DC measurement $$POWER=Const+Y_{p2}*Y_2+P_{p2}*P_2+Y_{p3}*Y_3+P_{p3}*P_3+Y_{p4}*Y_4+P_{p4}*P_4+Y_{p5}*Y_5+P_{p5}*P_5$$

Equation 1 demonstrates that the system's dose-response can be approximated by a power model. The slope and power of this power model are influenced by covariates such as temperature and hematocrit. Since the AC measurements (admittance and phase) are sensitive to these covariates, they are used in the slope and power terms to compensate for the covariate effects. The parameter estimates are established by parameter estimation with data collected where glucose, temperature and hematocrit are covaried. The DC value in this example was selected from one measured DC point, and Equation 1 is specific to a single DC value. For more DC values, i.e. more than one current response measurement taken during the DC block, a more general representation is:

$$\text{Predicted Glucose}=ba_0+a_1*Ieff+a_2*Peff+a_3*Yeff+(b_4+\exp(b_0+b_2*Peff+b_3*Yeff))*Ieff**(c_0+c_2*Peff+c_3*Yeff)$$

where: $Ieff=bV_0+bV_1*DC_1+bV_2*DC_2+bV_3*DC_3+bV_4*DC_4+bV_5*DC_5+bV_6*DC_6$ $Peff=bP_0+bP_1*P_1+bP_2*P_2+bP_3*P_3+bP_4*P_4+bP_5*P_5+bP_6*P_6$ $Yeff=bY_0+bY_1*Y_1+bY_2*Y_2+bY_3*Y_3+bY_4*Y_4+bY_5*Y_5+bY_6*Y_6$ The use of AC admittance magnitude and phase data to correct DC glucose response data for the effects of hematocrit and temperature is discussed in detail in U.S. Pat. No. 7,407,811.

Figure 6:
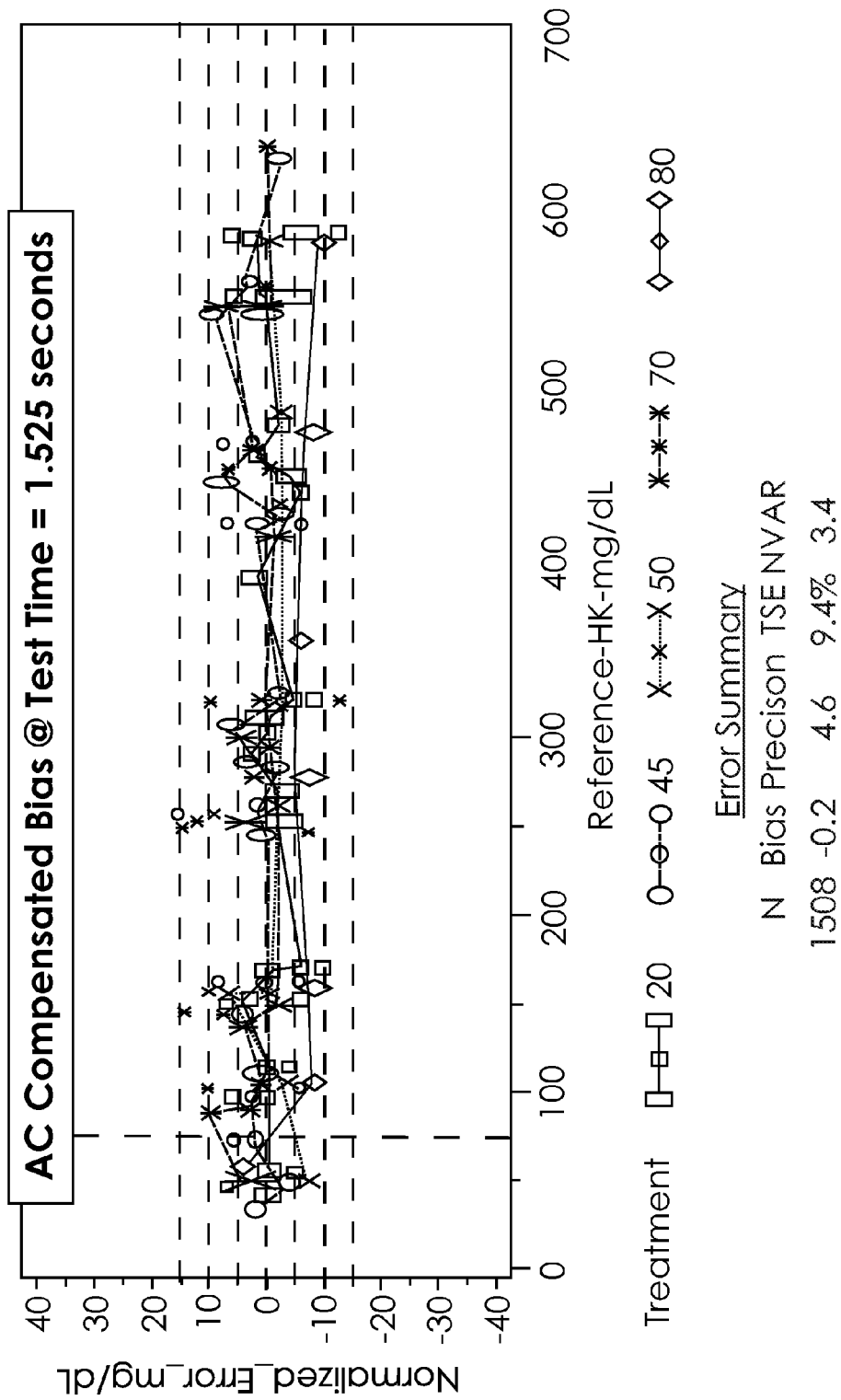
FIG. 6 is a graph of normalized error versus reference glucose for the data of FIG. 5 corrected using the methods described herein.

Like FIG. 5, FIG. 6 also plots the normalized error versus the reference glucose for all 105 samples, except that the DC measurement taken at 1525 ms has been corrected using the AC measurements and the methodology discussed hereinabove. Such correction allows the measurement system to compensate for the interfering effects of hematocrit and temperature. As can be seen, all measurement results now fall with +/−15% normalized error, with a total system error of 9.4%, all with a test time of only 1.525 seconds.

This Example 1 therefore demonstrates that an extremely short test time of 1.525 seconds can be achieved using multiple serial AC excitation frequencies in order to probe the sample and measure interferents that prevent accurate assessment of the glucose value, and to correct the measured glucose value to remove the effects of these interferents upon the measurement. This surprising result is in contravention to the teachings of the prior art as pointed out above.

Control of Reagent Thickness

Some of the embodiments disclosed herein, including embodiments shown from the description of Example 2 below, also utilize accurate control of the bio sensor reagent thickness through the use of a uniform method of applying the reagent to the biosensor surface, such as by slot die coating, for example. The reagent coatings disclosed herein are generally about 1.6-5 μm in thickness. The uniformity of the reagent coating, and thus the resulting uniform dissolution/hydration of the reagent film with the fluid sample, enables reproducibility that correlates well with the AC measurements to provide accurately compensated glucose. Non-uniform reagent thicknesses are detrimental to achieving faster methods and improved performance because of more variability in the measurements, especially at short times. For robust performance, we strive for a very uniform film. For a description of methods and disclosure relating to coating uniform films, see U.S. Patent Application Publication No. 2005/0008537, referred to above.

FIG. 1 and FIG. 7 illustrate the measured DC response of a sample applied to the reagent chemistry for various tests where the timing of the application of the DC excitation signal after sample application is varied from about 75 ms to 1400 ms. Hydration of FIG. 1 is less uniform strip to strip than the thinner reagent in FIG. 7. Applying the DC excitation too soon after sample application can result in non-Cottrellian responses and therefore inaccurate glucose concentration measurements.

Figures 30, 31:
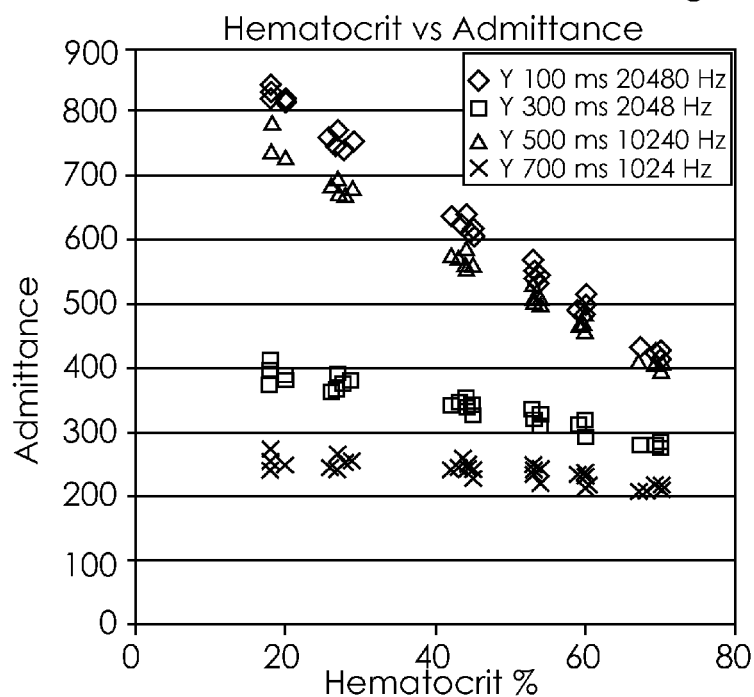
FIG. 30 is a table of estimated and measured dry coating film thickness according to coat weight in a known wet reagent application process.
FIG. 31 is a graph of admittance magnitude versus hematocrit from the fifth covariate study described herein.

Using coating methods as generally described in U.S. Patent Application Publication No. 2005/0008537, the reagent coating for FIG. 1 (50 g/m$^2$ coat weight) was approximately 3.6 μm and for FIG. 7 (20 g/m$^2$ coat weight) was approximately 1.6 μm. It can be seen that when the DC excitation is applied very quickly after sample application to the thinner reagent layer, the response begins to exhibit the expected Cottrellian-like decay characteristics much more quickly, thereby making accurate determinations of the sample glucose concentration possible for fast test times. This is because enzyme availability, hydration, and diffusion within the reagent layer, which limit how soon the DC measurement can be made, are improved with the thinner and or more uniform reagent layer thickness. FIG. 30 shows a table of coat weight settings and the estimated and actual measured dry coating film thicknesses, using wet reagent coating methods described in the U.S. 2005/0008537 publication. The equipment operating parameters required to achieve each coat weight will be appreciated from that publication and ordinary skill in the art in that regard.

Technology and methodologies useful for forming thin reagent strips on biosensors are disclosed in U.S. Patent Application Publication Nos. 2005/0016844 and 2005/0008537, the disclosures of which are hereby incorporated by reference herein in their entireties.

Figure 8:
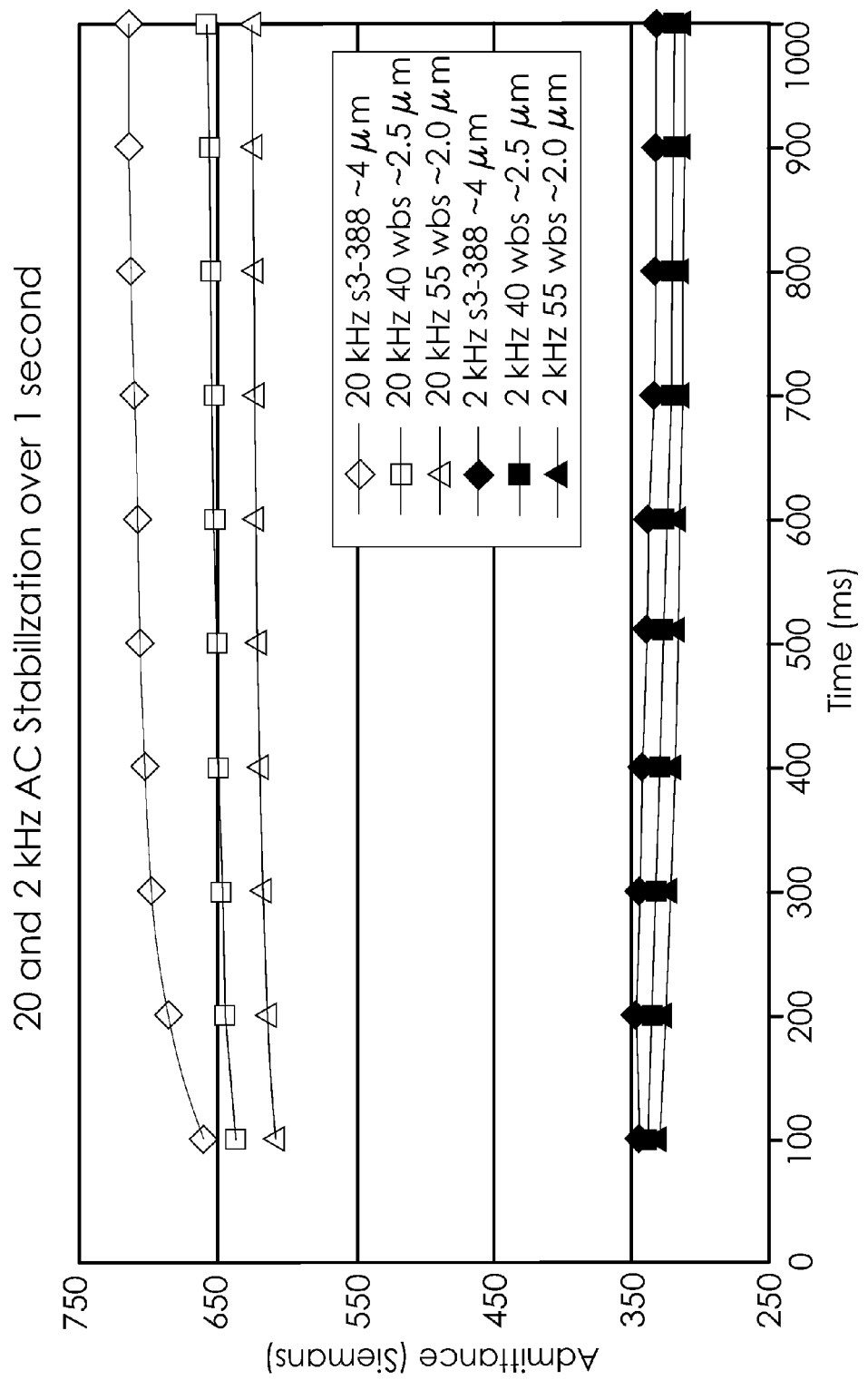
FIG. 8 is a plot of admittance versus time showing stabilization of the AC response in a first study described herein.

FIG. 8 summarizes tests performed on biosensors having a reagent coating formed thereon at thicknesses of 4 μm, 2.5 μm and 2.0 μm. Table 1 shows the general formulation of the wet reagent coated on the biosensors used in FIG. 8. The reagent was similar to that of ACCU-CHEK® AVIVA™ biosensors, but prepared with a milled silica. Milled silica was used to reduce the mean particle size of the silica due to concerns that the unmilled silica may have particle sizes that would be detrimental to thinner coatings. They were coated at different coat weights leading to different measured thicknesses. The goal was to start with a reagent mass for glucose biosensors that had some previous optimization at least for the upper thickness level. Then a slot die coating method was used to prepare reagent thicknesses from about 4 um to 2 μm by adjusting the coat weight using the same reagent mass. By making the reagents in this manner, the concentrations of the active ingredients that were initially optimized for the thicker coat weight are also reduced.

TABLE 1

| Wet Reagent | |
|---|---|
| | % w/w |
| Keltrol F | 0.22% |
| CMC | 0.57% |
| Sipernat FK320 DS (milled) | 2.02% |
| PVP K25 | 1.91% |
| Propiofan | 2.88% |
| GlucDOR wt | 0.40% |
| PQQ | 0.01% |
| Na-Succinate | 0.29% |
| Trehalose | 0.48% |
| KH$_2$PO$_4$ | 0.39% |
| K$_2$HPO$_4$ × 3 H$_2$O | 1.19% |
| Mediator 31.1144 | 0.93% |
| Mega 8 | 0.28% |
| Geropon T77 | 0.03% |
| KOH | 0.14% |
| Water total | 88.27% |
| Sum | 100.00% |

Blood samples were applied to each of the biosensors and AC excitation frequencies of either 2 kHz or 20 kHz were applied to the biosensors as the reagent was hydrated with the sample. Admittance data was measured every 100 ms for one second and plotted in FIG. 8. As can be seen, the AC admittance has stabilized in less than 400 ms after sample application, and the AC data at 100 ms was shown to be adequate for use in correcting the resultant DC glucose test using the procedure disclosed hereinbelow. From the data represented in FIGS. 1 and 7, it is clear that thin reagents stabilize quite fast after sample application. Of the films tested, the thinner reagents gave AC responses that stabilized faster and in a more reproducible manner.

Figure 9:
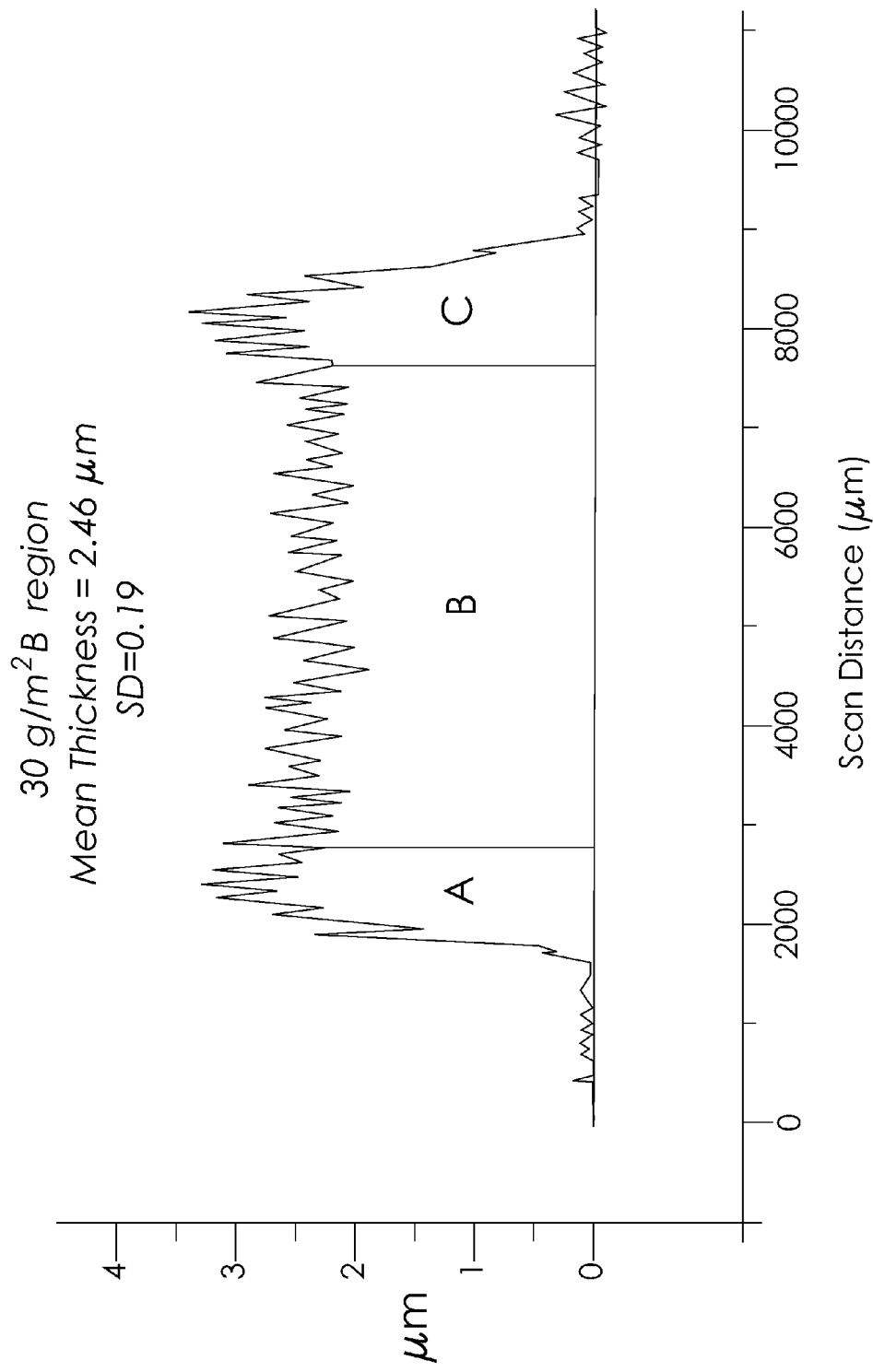
FIG. 9 is a plot showing the cross-sectional thickness of the biosensor reagent stripe in a first study described herein.

The ability to achieve fast test times as disclosed herein is greatly influenced by the rate of hydration of the enzyme and mediator in the reagent film, and the rate of diffusion of the reaction products to the electrode surface under the reagent film. The use of the slot die coating methodologies for deposition of reagent layers disclosed in U.S. Patent. Application Publication Nos. 2005/0016844 and 2005/0008537 allows deposition of uniformly thin film reagents for faster and more reproducible dissolution of reagents, fill times and hydration profiles. FIG. 9 shows a surface profilometry measurement of a thin film reagent deposited on a biosensor using these methods to a target thickness of 2.5 μm (nominal coat weight=30 g/m$^2$). As can be seen, the mean thickness in the central B region of the reagent strip is 2.46 μm. Enzyme availability, hydration, and diffusion are faster and more uniformly behaved with thin reagent films (in one embodiment, approximately 1.6-10 μm in thickness, and in other embodiments, approximately 1.6-5 μm in thickness).

Thin films benefit measurements in terms of faster hydration that permits measuring sooner after sample application. The AC stabilization appears to be less affected by film thickness than the DC response. A more Cottrellian-like behavior is observed in response to DC excitation at earlier times when the films are thinner. This can be seen by comparison of FIG. 1 and FIG. 7. FIG. 1 shows current responses for thicker films, i.e. 50 g/m$^2$, which as illustrated give variable early I vs. T traces when DC excitation is started around 100-700 ms after sample sufficiency is detected. In contrast, as shown in FIG. 7, the current responses follow a nice trend for the 20 g/m$^2$ for the same time range. In addition, the I vs. T response becomes more Cottrellian-like at about 300 ms after applying the DC potential. There are some limitations that need to be considered with regard to thin films, however. There is a minimum amount of enzyme needed on the sensor both for obtaining a linear response and maintaining the required long-term stability of the sensor. The films in this example, because they were made from the same reagent mass, had proportionally less enzyme as they were made thinner. The lower limit of film thickness generally depends on the concentration of enzymes in the reagent mass to provide adequate response and stability. It is also understood that there would be some lower limit of thickness where the coating methods and variability of the thickness of the substrate would not provide a uniform coating thickness. For other issues and disclosure relating to control of uniform and homogeneous film thickness, see, e.g., U.S. Patent Application Publication No. 2005/0008537 referred to hereinabove.

EXAMPLE 2

Sequential Multiple AC Frequency Test with Fast Total Test Time and Varying Reagent Thickness A covariate study testing multiple whole blood samples for glucose concentration was performed using the electrode and testing structures similar to the ACCU-CHEK® AVIVA™ biosensor available from Roche Diagnostics, Inc. of Indianapolis, Ind. USA. A pyrroloquinoline quinone dependent glucose dehydrogenase (PQQ-GDH) based reagent with the same or substantially similar formulation from Table 1 (above) was applied to the biosensors in one of three thicknesses: 2 µm, 2.5 µm and 4 µm. A covariate study was performed with whole blood samples similar to Example 1 but with six glucose concentrations, five hematocrit levels, and five temperatures, as detailed in FIG. 10.

Figure 11:
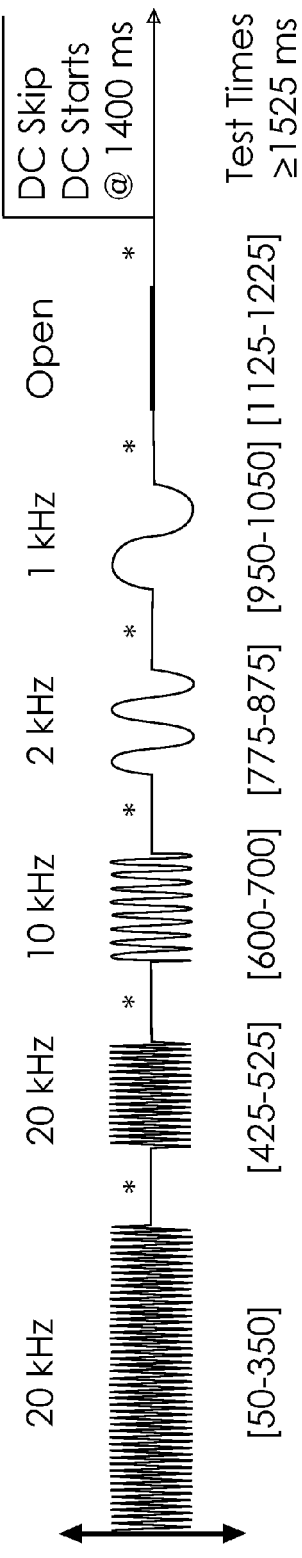
FIG. 11 illustrates the excitation signal profile and timing used for a second study described herein.

The AC excitation potentials for this Example 2 were applied sequentially as detailed in FIG. 11. A 10 kHz dose detection and sample sufficiency method (not shown) was followed by a 300 ms 20 kHz signal followed by 100 ms applications of 20 kHz, 10 kHz, 2 kHz and 1 kHz signals. The measurement electrodes were then held at an open circuit for 100 ms, followed by application of a 550 mV DC signal. Because of the pre-set timing parameters in the existing meters of the DATS, there was a 50 ms stabilization delay and a 25 ms trailing data communication period between each excitation block. Measurements of the response to the DC signal were extracted at Total Test Times starting at about 1500 ms, and measured at 100 ms intervals. AC admittance values were captured for each of the AC excitation blocks in order to correct the DC glucose measurement for the interfering effects of hematocrit and temperature using the following equation:

Predicted Glucose=INT+$Yi2*Y2+Pi2*P2+Yi3*Y3+$
$Pi3*P3+Yi4*Y4+Pi4*P4+Yi5*Y5+Pi5*P5$+exp
(SLOPE+$Ys2*Y2+Ps2*P2+Ys3*Y3+Ps3*P3+$
$Ys4*Y4+Ps4*P4+Ys5*Y5+Ps5*P5$)
*DC**POWER         (equation 2)

where: Yi2, Yi3, Yi4, Yi5, Ys2, Ys3, Ys4 and Ys5 are constants
Pi2, Pi3, Pi4, Pi5, Ps2, Ps3, Ps4 and Ps5 are constants
Y2 is the admittance magnitude at 20 kHz (second block)
Y3 is the admittance magnitude at 10 kHz
Y4 is the admittance magnitude at 2 kHz
Y5 is the admittance magnitude at 1 kHz
P2 is the phase angle at 20 kHz (second block)
P3 is the phase angle at 10 kHz
P4 is the phase angle at 2 kHz
P5 is the phase angle at 1 kHz
INT is the intercept
SLOPE is the slope
DC is the uncorrected glucose response predicted with the DC measurement POWER=Const+$Yp2*Y2+Pp2*P2+Yp3*Y3+Pp3*P3+$
$Yp4*Y4+Pp4*P4+Yp5*Y5+Pp5*P5$ It will be appreciated that Equation 2 is substantially the same as Equation 1 from Example 1. The primary difference is only in the sequence order of applying the different frequencies, wherein the Example 1 applied frequency sequence was 10-20-2-1 kHz, and the Example 2 applied frequency sequence was 20-10-1 kHz.

The uncorrected glucose response from the DC measurement (i.e. uncorrected for the interfering effects of hematocrit and temperature) was determined using well-known prior art techniques. This DC glucose response was then corrected for the interfering effects of hematocrit and temperature using the AC admittance magnitude and phase measurement data as detailed above in equation 2. The Total System Error, bias, precision and NVar were calculated for each and these are tabulated in FIG. 12. As can be seen, the Total System Error for all three reagent thicknesses were very good at Total Test Times as low as 1.525 seconds.

As referred to above, Total System Error, or TSE, is a combined measure of accuracy and precision of the system. It is typically defined as: (Absolute Bias)+2*(Precision). The details are as follows:

Bias=Average of Normalized Error;

Precision=StdDev(Normalized Error);

where

Normalized Error=(Predicted Glucose−Reference Glucose) when Reference Glucose<=75 mg/dl; and Normalized Error=(Predicted Glucose−Reference Glucose)*100/(Reference Glucose) when Reference Glucose>75 mg/dl.

Figure 13:
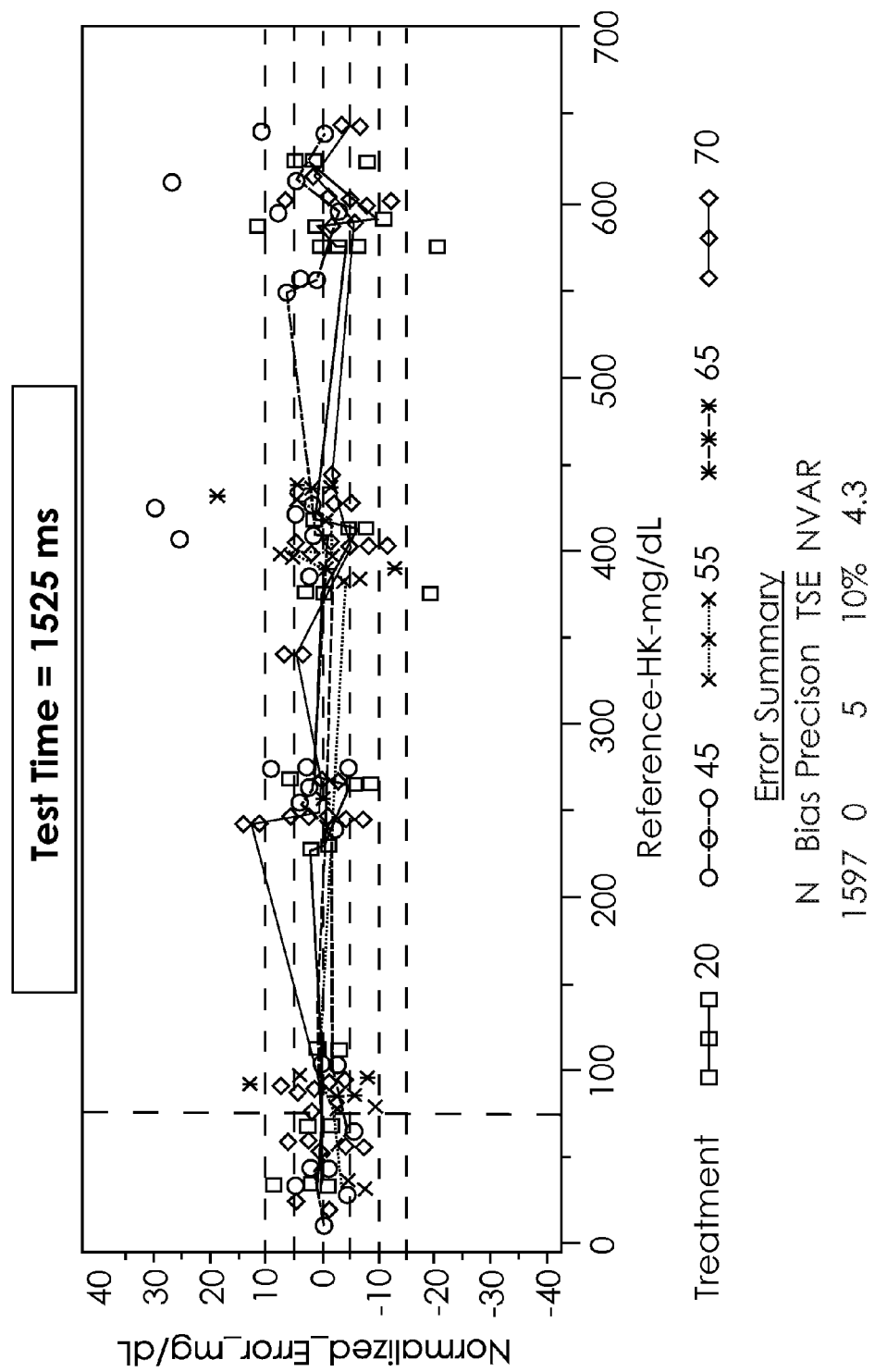
FIG. 13 is a plot of normalized error versus reference glucose level for a second study described herein.

FIG. 13 plots the normalized error versus the reference glucose value for the DC measurement data corrected using the AC measurements as detailed hereinabove. Only the DC measurement taken at 1500 ms was used (+25 ms for communications), therefore this data represents a realistic total test time of 1.525 seconds. The interfering effects of the hematocrit and temperature have been substantially reduced, with a Total System Error of 10.0% for the entire covariate study.

Figure 14:
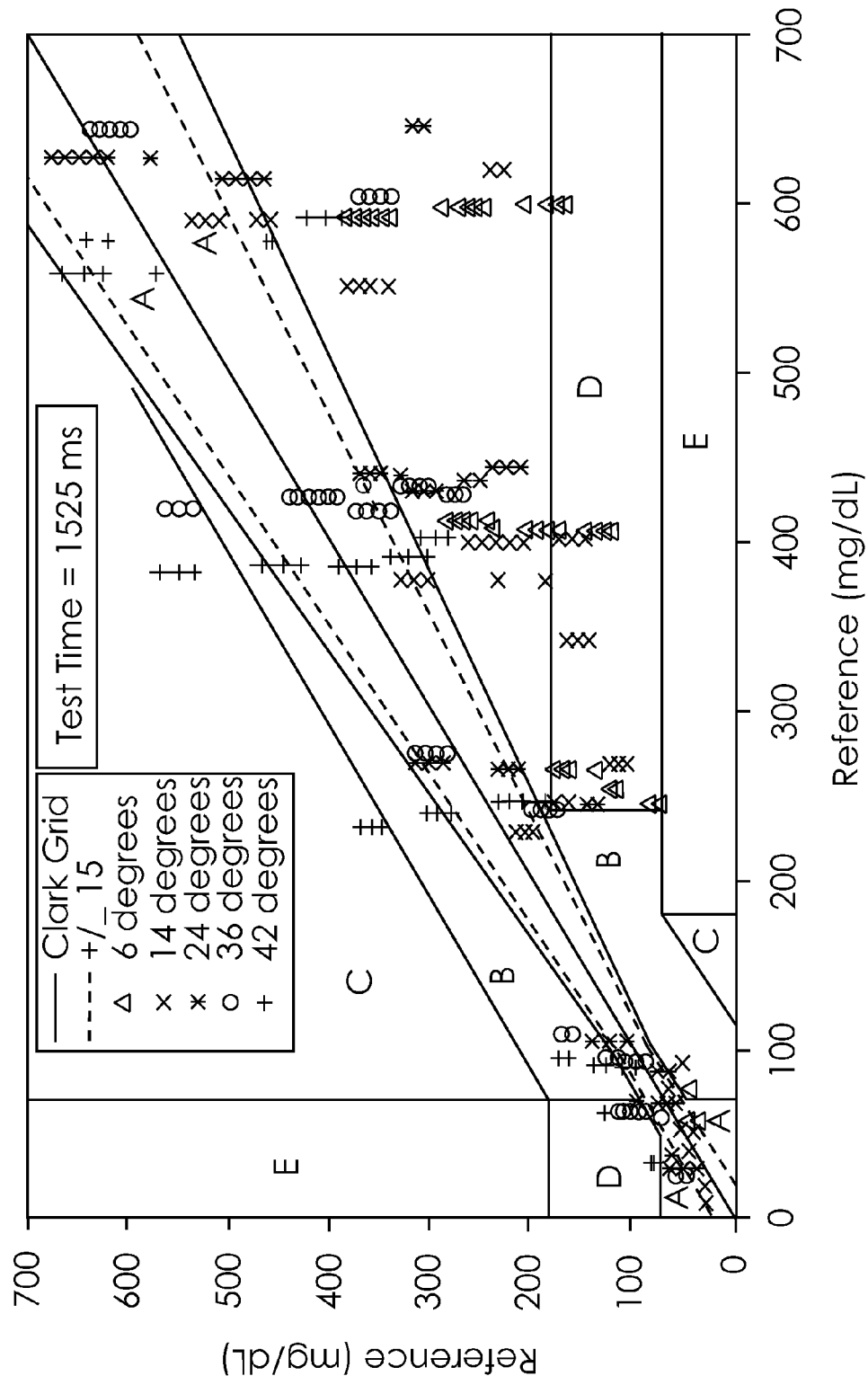
FIG. 14 is a Clark Error Grid showing predicted glucose versus reference glucose for the uncorrected DC data obtained in a second study described herein.

FIG. 14 is a Clark Error Grid showing the predicted glucose value versus reference glucose value for all of the uncorrected DC glucose measurements taken at 1525 ms. The Clarke Error Grid Analysis (EGA) was developed in 1987 to quantify the clinical accuracy of patient estimates of their current blood glucose as compared to the blood glucose value obtained in their meter. See Clarke W L, Cox D, Gonder-Frederick L A, Carter W, Pohl S L: *Evaluating clinical accuracy of systems for self-monitoring of blood glucose. Diabetes Care* 10:622-628, 1987. The Clark Error Grid has since been used to quantify the clinical accuracy of blood glucose estimates generated by test meters as compared to a reference value. The EGA is generally accepted as a standard methodology for determining the accuracy of blood glucose meters.

The Clark Error Grid breaks down a scatter plot of test results from a reference glucose meter and an evaluated glucose meter into five regions. Region A are those values within 20% of the reference sensor, Region B contains points that are outside of 20% but would not lead to inappropriate treatment, Region C are those points leading to unnecessary treatment, Region D are those points indicating a potentially dangerous failure to detect hypoglycemia, and Region E are those points that would confuse treatment of hypoglycemia for hyperglycemia and vice-versa. In FIG. 14, the dashed lines additionally indicate values within 15% of the reference sensor.

As can be readily seen in FIG. 14, the uncorrected glucose values fall well outside the +/−15% error window, which is the desired error window set forth in a Clark Error Grid. This level of accuracy would be considered to be unacceptable in a glucose test meter according to general industry practice for blood glucose monitoring systems, as well as according to FDA guidelines.

Figure 15:
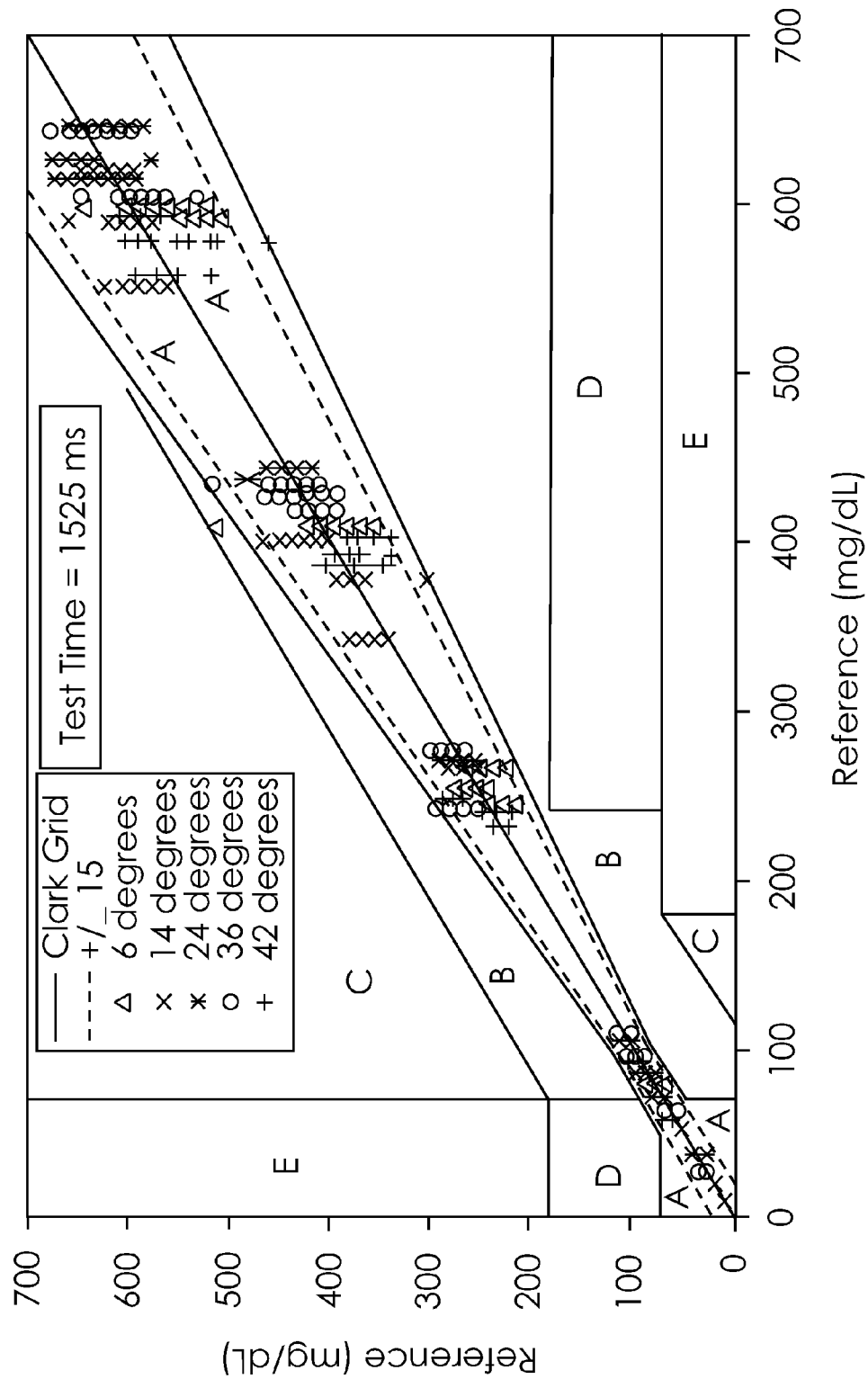
FIG. 15 is a Clark Error Grid showing predicted glucose versus reference glucose for the DC data of FIG. 14 corrected using AC measurement data.

FIG. 15 is a Clark Error Grid showing the same DC test data shown in FIG. 14, except that the data has been corrected for the interfering effects of hematocrit and temperature using the methodology described hereinabove. As can be readily seen in FIG. 15, the performance of the measurement system when corrected for hematocrit and temperature using the AC measurement data is far superior to using only the DC measurement results to predict the glucose values at extremely fast Total Test Times.

As can be seen from the above Example 2, the use of thin reagent films, such as about 1.6-5 µm in thickness supports the ability to perform accurate glucose determinations, corrected for the interfering effects of hematocrit and temperature, with Total Test Times below 2 seconds. The uniformity of the reagent coating, and thus the resulting uniform dissolution/hydration of the reagent film with the fluid sample, is believed to enable reproducibility that correlates well with the AC measurements to provide accurately compensated glucose test results.

From Examples 1 and 2, it has become clear that, despite the previous understanding in the art, shorter test times can be achieved by shortened sequential AC blocks and/or by use of fewer sequential AC frequencies. However, using more frequencies can provide benefits in measurement correction, especially when correcting for multiple variables or when desired to actually provide an indication of the level or general range of one or more such variables in addition to the analyte measurement. In order to accomplish this, and still achieve the shortest possible test, the use of multi-frequency excitation waveforms was explored, such as set forth in Examples 3 and 4.

Multi-Frequency Excitation

As noted herein, some of the embodiments disclosed herein utilize the collection of AC test data at multiple frequencies over a shorter time period by using multi-frequency excitation waveform techniques. These multi-frequency excitation waveforms are formed by adding a plurality of individual waveforms of varying frequency together so that the fluid sample is excited by multiple frequencies substantially simultaneously, rather than sequentially.

The resulting sample response can then be measured and this measurement will contain the sample response to all of the excitation frequencies. The specific contribution from each excitation frequency component can be then deduced by use of Fourier Transform techniques, such as a Discrete Fourier Transform (DFT). Although the various examples disclosed herein utilize multi-sine excitation waveforms, those skilled in the art will recognize that the multi-frequency waveform may be constructed using individual waveforms having any desired shape, such as triangular, square, sawtooth, delta, etc., just to name a few non-limiting examples. The component AC waveforms used to create the multi-frequency waveform may each have any desired frequency and any desired amplitude. The use of multi-frequency techniques not only shortens the time necessary to collect the desired data (since the AC measurements are made simultaneously rather than sequentially), but also correlates better for correction since the sample is varying less during the data collection corresponding to each applied frequency. This is particularly true for tests utilizing a very fast Total Test Time, where the measurements are made very shortly after sample application and the sample is still undergoing diffusion and reaction with the reagent chemistry. Also, the AC measurement can be made closer in time to the DC measurement. Better correlation between the AC and DC allows for better interferent compensation even if the sample is not in steady state.

An exemplary prior art measurement sequence for a blood glucose testing system that corrects for the interfering effects of hematocrit and temperature, such as those disclosed in U.S. Pat. No. 7,407,811, is as follows:

Step 1: Blood is applied to a biosensor in a meter.
Step 2: AC measurements are taken of the sample for drop detect and/or dose sufficiency.
Step 3: AC measurements are taken over a period of time to allow calculation of correction factors for hematocrit and temperature. In many instances, multiple AC excitation frequencies are applied to the sample sequentially.
Step 4: DC measurements are taken to measure the raw (uncorrected) glucose response.
Step 5: The raw DC response is compensated for hematocrit and temperature effects using the AC measurement-derived correction factors.
Step 6: Measurement result is displayed to the user.

This procedure has some drawbacks with respect to obtaining a measurement result in less than 2 seconds. While accurate measurement results may be obtained by correcting the raw DC glucose measurement with the AC-derived data on hematocrit and temperature, the additional time required to collect the AC data lengthens the total test time and also separates in time the various AC and DC measurements that are used to arrive at the final measurement result. This separation in time of the various AC and DC measurements can be of some concern in some situations since the sample under test continues to undergo chemical reactions with the reagents and the reagents are being hydrated during this time. That is, in a measurement sequence in which an AC signal is applied with different waveform frequencies sequentially, the admittance and phase data for each frequency, while still useful for the correction of the subsequent raw DC response measurement, is not ideal because each data point is taken at a different time during the progression of the sample-reagent hydration-reaction dynamics. By applying all frequencies simultaneously within the AC excitation waveform, the admittance and phase data for each frequency is still separately discernible and advantageously relates to the same state of the sample-reagent dynamics.

Figure 29:
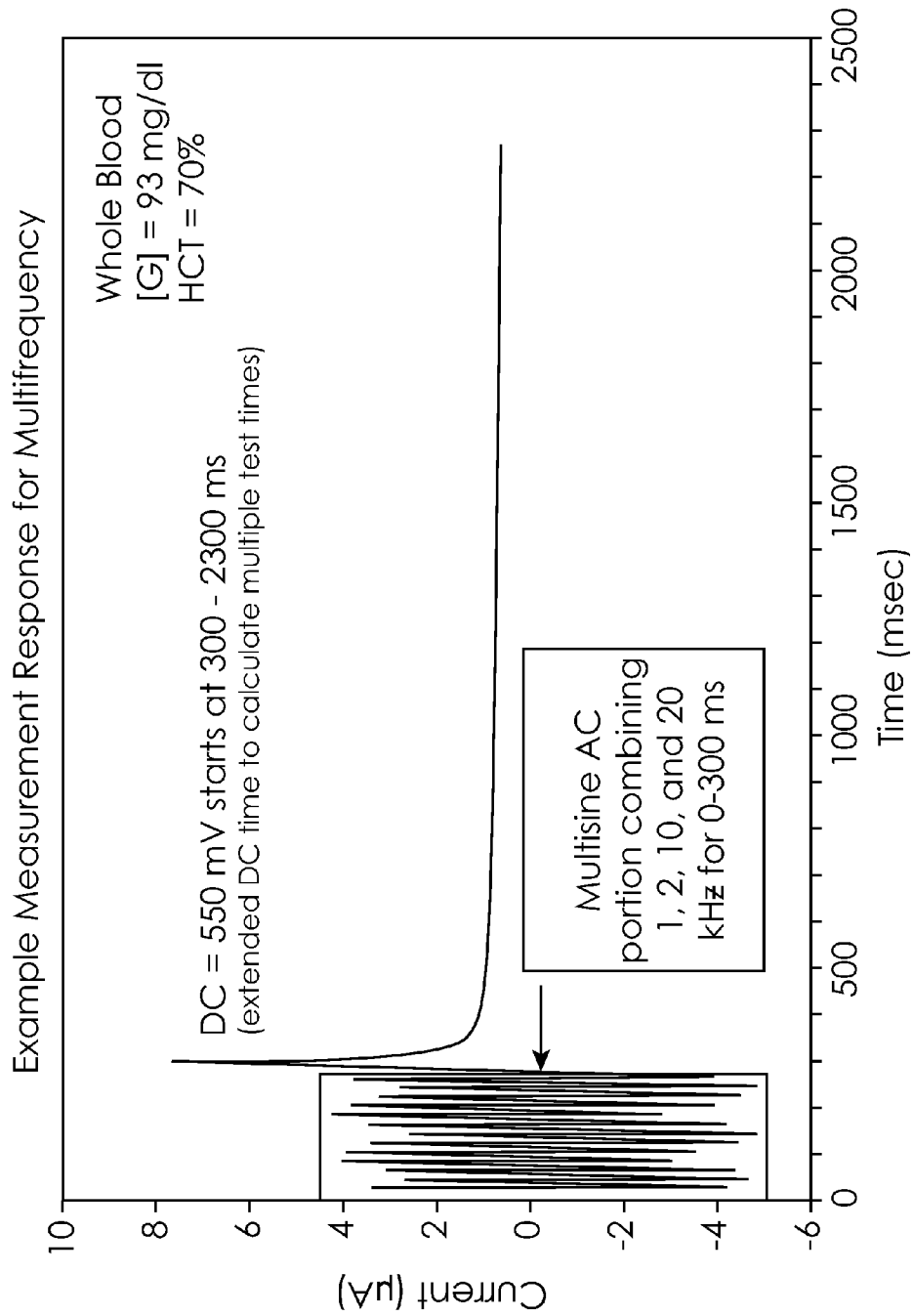
FIG. 29 is an exemplary current response resulting from a measurement sequence comprising a multi-frequency AC excitation waveform followed by a DC excitation, performed on a whole blood sample having a target glucose concentration of 93 mg/dL and 70% hematocrit.

A current response measured from application of an exemplary multi-frequency AC excitation waveform followed by application of a DC signal is illustrated in FIG. 29. For Examples 3 and 4, data acquisition was conducted using an electrochemical test stand constructed on the basis of VXI components from Agilent, and programmable to apply AC and DC potentials to sensors in requested combinations and sequences and to measure the resulting current responses of the sensors.

EXAMPLE 3

Multi-Frequency AC Test with Fast Total Test Time

The measurements conducted for Example 3 were made with electrode structures similar to that of ACCU-CHEK® AVIVA™ biosensors and reagents the same or similar to the formulation set forth in Table 1 (above). These sensors were fabricated using generally the same technology as ACCU-CHEK® AVIVA™ biosensors using a combination of processes including sputtering, laser ablation, reagent slot die coating, and lamination.

The measurement sequence consisted of three basic blocks. The first measurement block (not shown) utilized a 10240 Hz sine wave excitation applied to the test strips in order to detect sample dose sufficiency (filling of the capillary test chamber sufficient to conduct a measurement). The use of AC measurements for drop detect and dose sufficiency is described in U.S. Pat. No. 7,597,793, referred to hereinabove.

After sufficient sample was detected, the second measurement block was begun using a multi-sine (also known as polyphonic) waveform for a short time interval (as detailed below) to simultaneously collect AC admittance magnitude and phase data for each frequency of interest. The multi-sine waveform used for this Example 3 was constructed by summing sine waves of four frequencies (1024, 2048, 10240 and 20480 Hz). These frequencies were selected because they are known to be useful for correction of interferents, according to Applicants' prior disclosures regarding use of AC excitation which are referred to hereinabove. The higher frequency ranges of about 20 and about 10 kHz are known to provide useful correction for hematocrit. The lower frequency ranges of about 1 and about 2 kHz were included because of the known potential for useful discrete measurements. Generally, this combination of frequencies allow for correction of multiple parameters such as hematocrit and temperature. It is well understood that these values do not have to be specifically 20 kHz, for example, but only in a range where the interferents can be measured reasonably independent of the glucose response which is to be corrected. A higher frequency may correlate more with one interferent such as hematocrit, whereas another frequency may correlate more with another interferent. Optimization of the frequency or combination of frequencies that would provide the best overall correction response would be useful, and is well within the skill of a person of ordinary skill in the art in view of this disclosure. However, in working with multi-frequency AC waveforms to reduce the time to collect response data from multiple frequencies while still providing good correction and short total test times, it was decided that using the frequencies in these known ranges would be useful in order to rely on past experience. In addition, previous experience shows that data from more than one frequency can correct for multiple interferents better than measuring at only one frequency. Four frequencies were chosen here so that previously programmed data analysis routines could be used. However, two, three or even five or more frequencies, for example, may just as well supply adequate correction. Some discrete AC methods with only two AC frequencies have been conducted.

Figure 16:
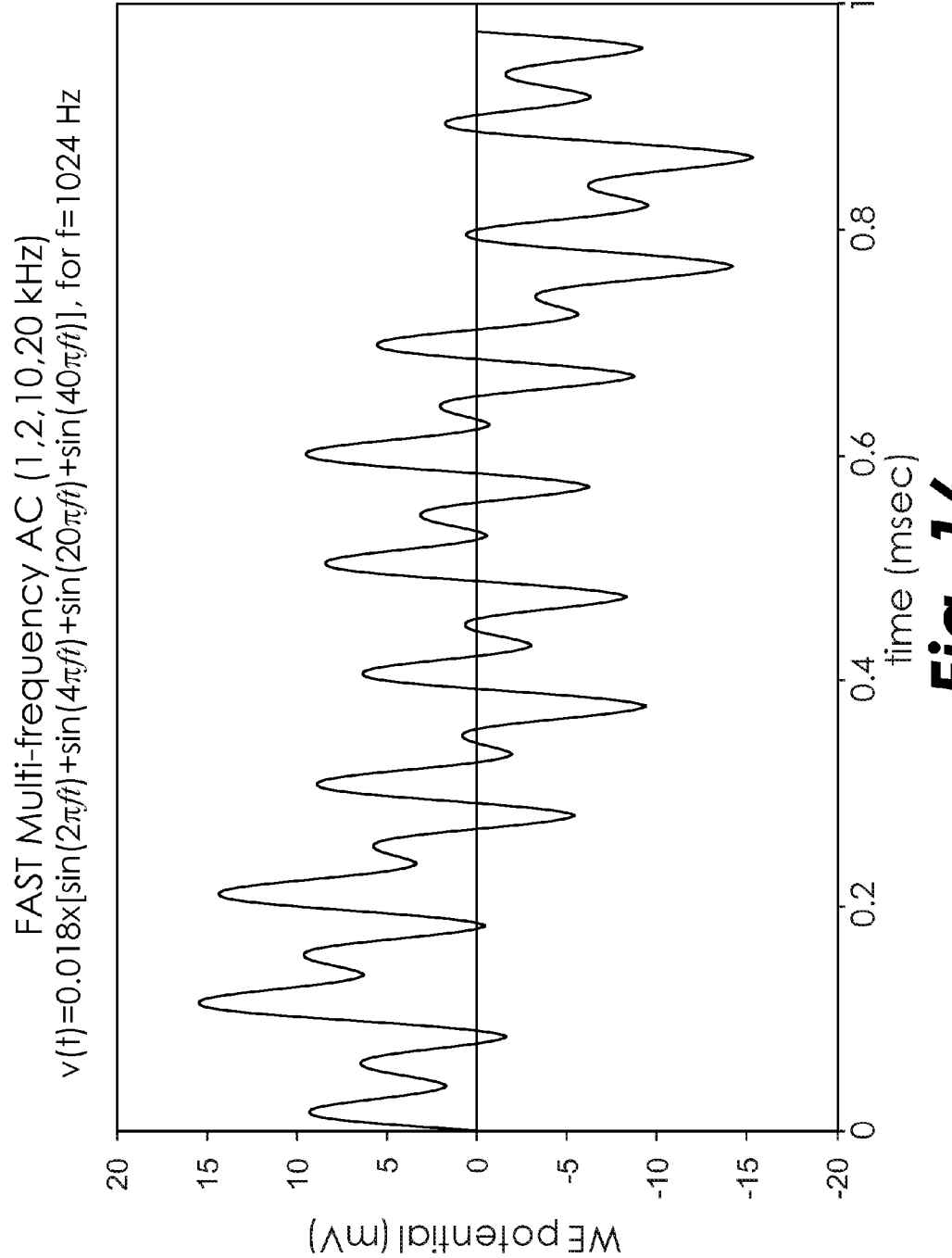
FIG. 16 is a plot of one embodiment multi-sine excitation waveform used in a third study described herein.

For Example 3, the multi-sine waveform consisted of one period of the 1024 Hz signal, two periods of the 2048 Hz signal, 10 periods of the 10240 Hz signal, and 20 periods of the 20480 Hz signal. The peak amplitude was set at 12.7 mV, but due to the multi-sine nature of the signal, the actual RMS value would be significantly lower. (RMS is the root mean square value of the waveform SQRT[(1/N)*SUM($x^2$)].) The waveform comprised 16000 data points that were input to a digital-to-analog converter and is illustrated in FIG. 16.

One benefit of using the multi-sine excitation waveform is that the AC measurement time required to collect data for all four frequencies is reduced because the measurements are made simultaneously. Another benefit of the multi-sine excitation waveform is that the AC measurement data for all of the frequencies is collected simultaneously and is thus less affected by the fact that the sample is changing as it reacts with the reagent.

The multi-sine waveform was applied to the test sample for 300 ms after an indication of dose sufficiency and analyzed in 100 ms intervals. Although this Example 3 utilized a 300 ms measurement period, longer, shorter and even variable time periods may be employed with similar results. Generally, to achieve a Total Test Time of two seconds or less, the range for the multi-sine measurement period in one embodiment is 100 ms to 1900 ms. With the ACCU-CHEK® AVIVA™ test structures used, 200-500 ms was a sufficient period to give reproducible AC responses from the test sample.

Figure 17B:
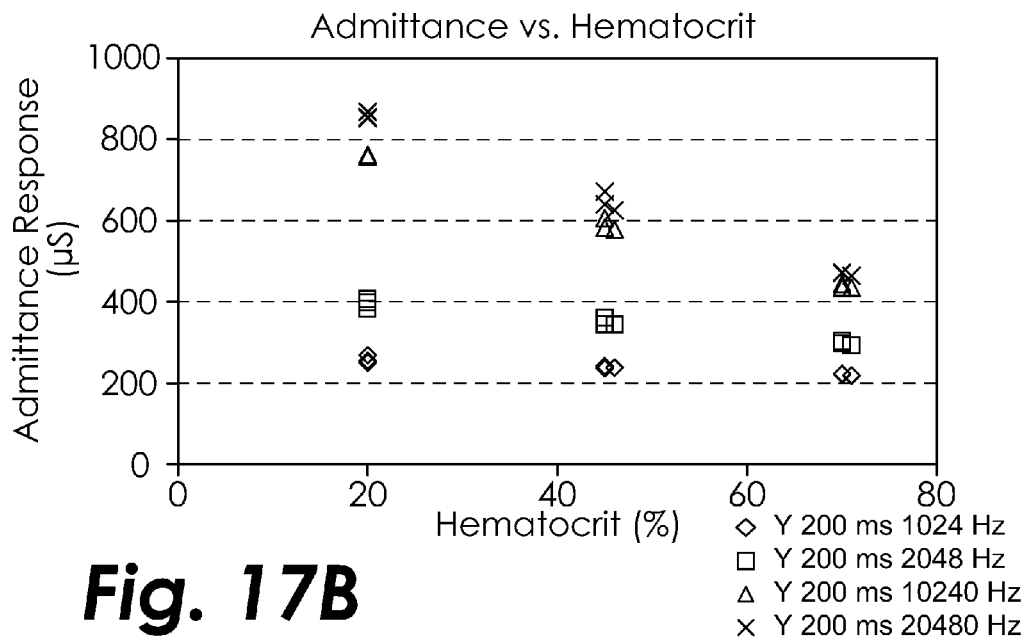
FIG. 17B is a graph of admittance magnitude versus hematocrit from the data table of FIG. 17A.
Figure 17C:
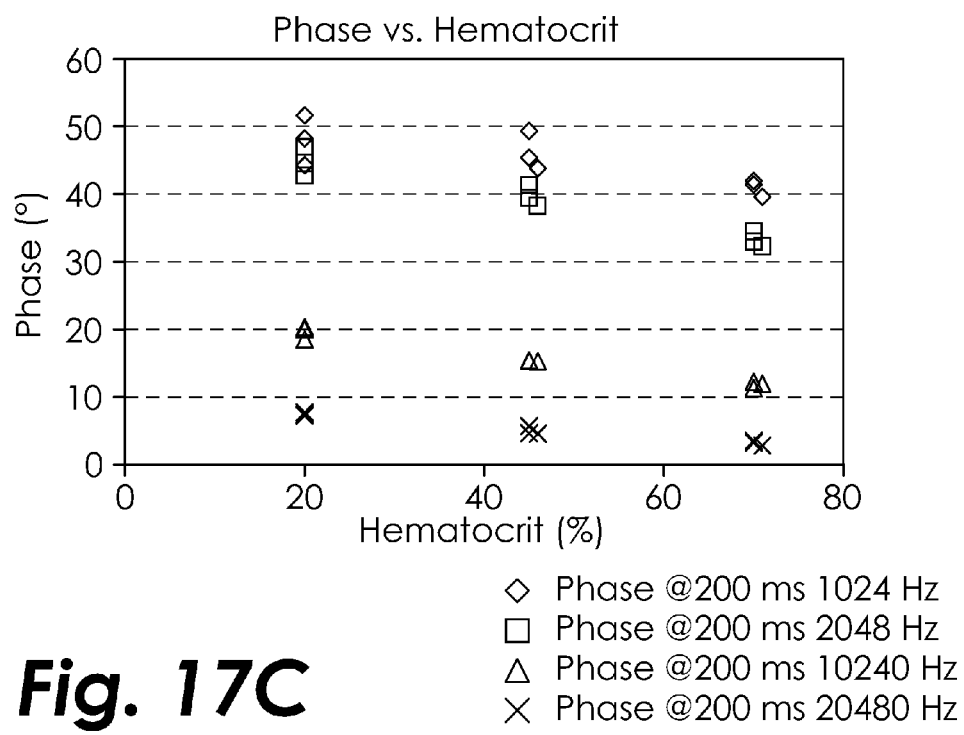
FIG. 17C is a graph of phase versus hematocrit from the data table of FIG. 17A.

Although the various excitation frequencies are applied to the sample simultaneously using the multi-sine signal, the responses attributable to each frequency component can be extracted from the AC measurement data using an appropriate mathematical function, such as a Fast Fourier Transform (FFT) or a Discrete Fourier Transform (DFT) or other mathematical techniques, as will be appreciated by those skilled in the art. Admittance magnitude and phase data for each frequency was extracted in the present Example 3 using DFT. This extracted admittance data for each frequency is shown in FIG. 17A for the time point correlating to 200 ms after dose sufficiency for all nine samples tested. A graph of phase to hematocrit at each frequency for Example 3 is illustrated in FIG. 17B, and a graph of admittance magnitude to hematocrit at each frequency for Example 3 is illustrated in FIG. 17C.

The second measurement block consisted of a 550 mV DC signal applied to the sample in order to obtain a raw (uncorrected) predicted glucose reading, as is known in the art. Four DC time points were extracted from the measurement data as 100 ms average data points with ending data points at 500, 600, 1000 and 1500 ms (i.e. for Total Test Times of 0.5, 0.6, 1.0 and 1.5 seconds).

Nine whole blood samples were prepared for a covariate study using target glucose concentrations of 90, 250 and 600 mg/dL and target hematocrit values of 20, 45 and 70%. For each sample tested, each DC time point was analyzed by nonlinear fit and the 300 ms AC admittance magnitude and phase data was used to calculate the predicted glucose response compensated for the effects of hematocrit and temperature using the following equation:

$$\text{Predicted Glucose} = \text{INT} + Yi1^*Y1 + Pi1^*P1 + Yi2^*Y2 + Pi2^*P2 + Yi3^*Y3 + Pi3^*P3 + Yi4^*Y4 + Pi4^*P4 + \exp(\text{SLOPE} + Ys1^*Y1 + Ps1^*P1 + Ys2^*Y2 + Ps2^*P2 + Ys3^*Y3 + Ps3^*P3 + Ys4^*Y4 + Ps4^*P4)^* \text{DC}^{**}\text{POWER}$$ (equation 3)

where: Yi1, Yi2, Yi3, Yi4, Ys1, Ys2, Ys3 and Ys4 are constants
Pi1, Pi2, Pi3, Pi4, Ps1, Ps2, Ps3 and Ps4 are constants
Y1 is the admittance magnitude at 1024 Hz
Y2 is the admittance magnitude at 2048 Hz
Y3 is the admittance magnitude at 10240 Hz
Y4 is the admittance magnitude at 20480 Hz
P1 is the phase angle at 1024 Hz
P2 is the phase angle at 2048 Hz
P3 is the phase angle at 10240 Hz
P4 is the phase angle at 20480 Hz
INT is the intercept
SLOPE is the slope
DC is the uncorrected glucose response predicted with the DC measurement $$\text{POWER is} = \text{Const} + Yp1^*Y1 + Pp1^*P1 + Yp2^*Y2 + Pp2^*P2 + Yp3^*Y3 + Pp3^*P3 + Yp4^*Y4 + Pp4^*P4.$$

Again this equation is the same form as Equations 1 and 2, but as can be seen the variables range from Y1 to Y4 and P1 to P4 for the simultaneous AC at 200 ms, rather than Y2-Y5 and P2-P5 which are used in Equations 1 and 2.

As discussed above, the use of AC admittance magnitude and phase data to correct DC glucose response data for the effects of hematocrit and temperature is discussed in U.S. Pat. No. 7,407,811.

The uncorrected glucose response from the DC measurement (i.e. uncorrected for the interfering effects of hematocrit and temperature) was determined using well-known prior art techniques. This DC glucose response was then corrected for the interfering effects of hematocrit and temperature using the AC admittance magnitude and phase measurement data as detailed above in equation 3. The Total System Error (TSE), bias, precision and NVar were calculated for each Total Test Time (for both corrected and uncorrected results) and these are tabulated in FIG. 18. As can be readily seen, the performance of the measurement system when corrected for hematocrit and temperature using the AC measurement data is far superior to using only the DC measurement results to predict the glucose values. Furthermore, acquiring the AC measurement data simultaneously for multiple excitation frequencies permits extremely fast Total Test Times with measurement results exhibiting very good TSE values for Total Test Times of 1.5 seconds, 1.0 second, 0.6 seconds and 0.5 seconds.

Figure 19:
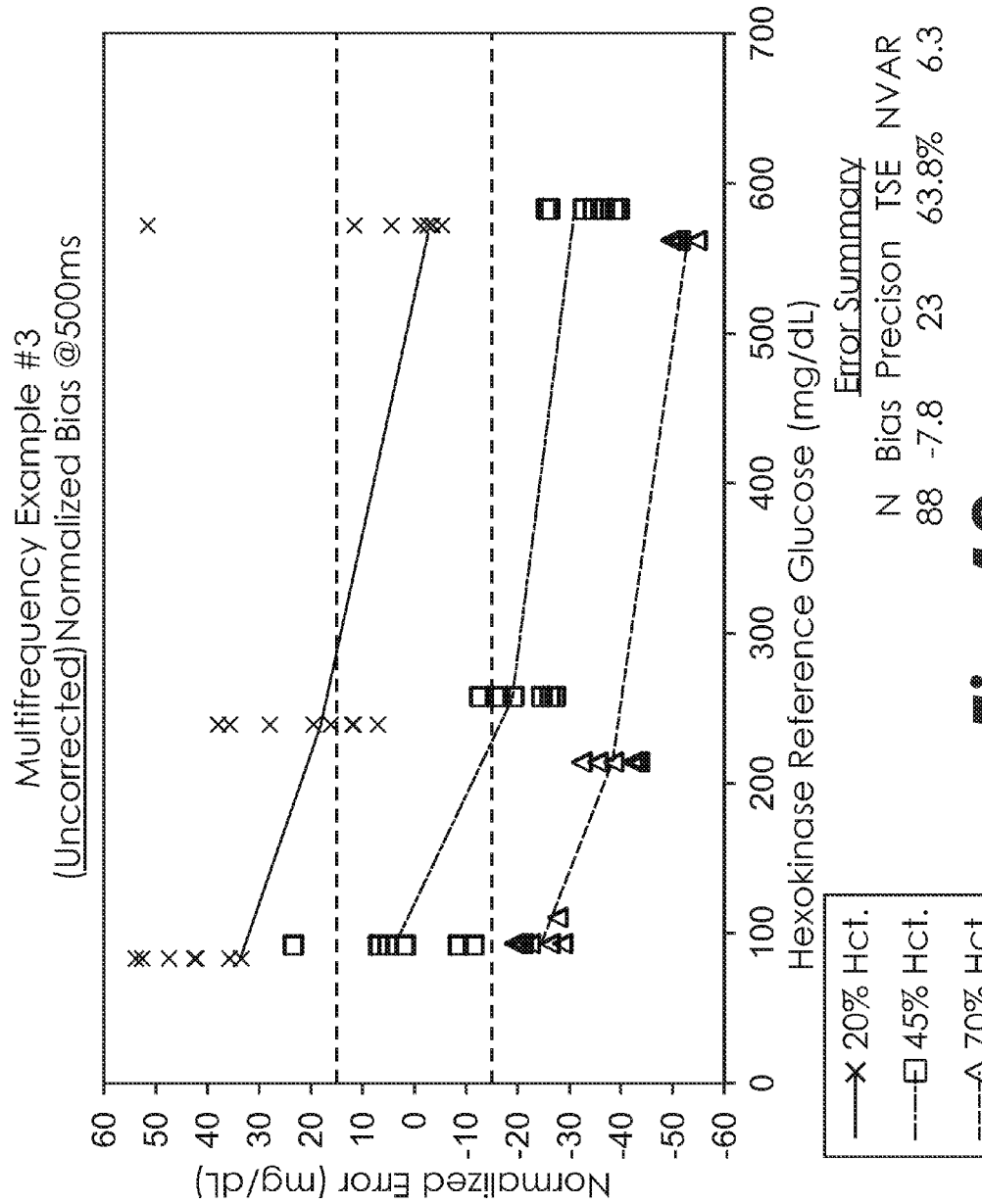
FIG. 19 is a graph of normalized error versus reference glucose for uncorrected measurement data from a third study described herein.
Figure 20:
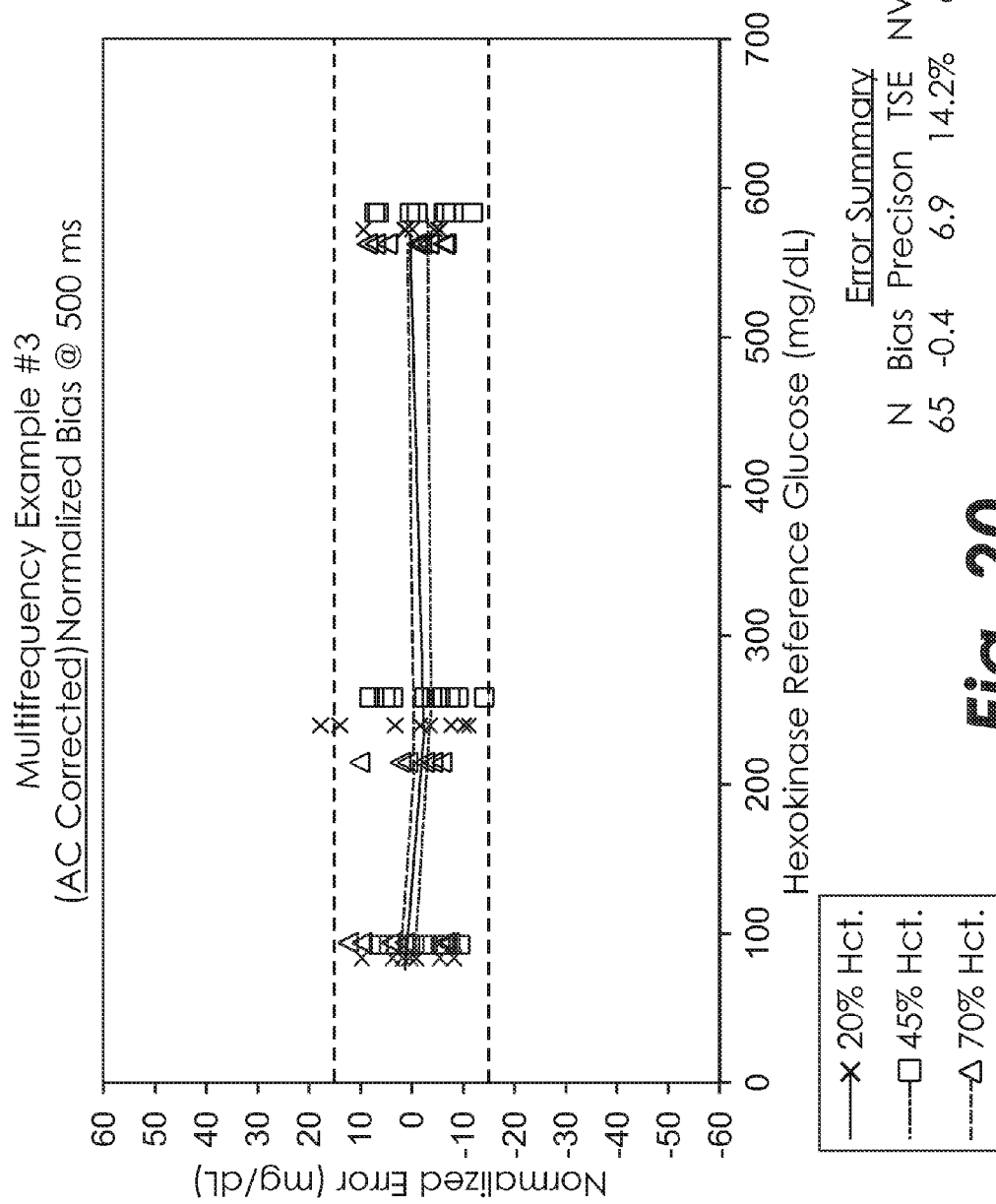
FIG. 20 is a graph of normalized error versus reference glucose for the data of FIG. 19 corrected using the methods disclosed herein.

FIG. 19 plots the normalized error versus the reference glucose value for the uncorrected glucose measurements, and a significant dependence on the hematocrit value can be seen in the data. The Total System Error is 53.8%. FIG. 20 plots the normalized error versus the reference glucose value for the same measurements, only this time the DC measurement data has been corrected using the AC measurement as detailed hereinabove. The interfering effect of the hematocrit has clearly been substantially reduced, with a Total System Error of 14.2%. This reduction was achieved using only the AC measurement data taken at 500 ms after the dose sufficiency indication.

Figure 21:
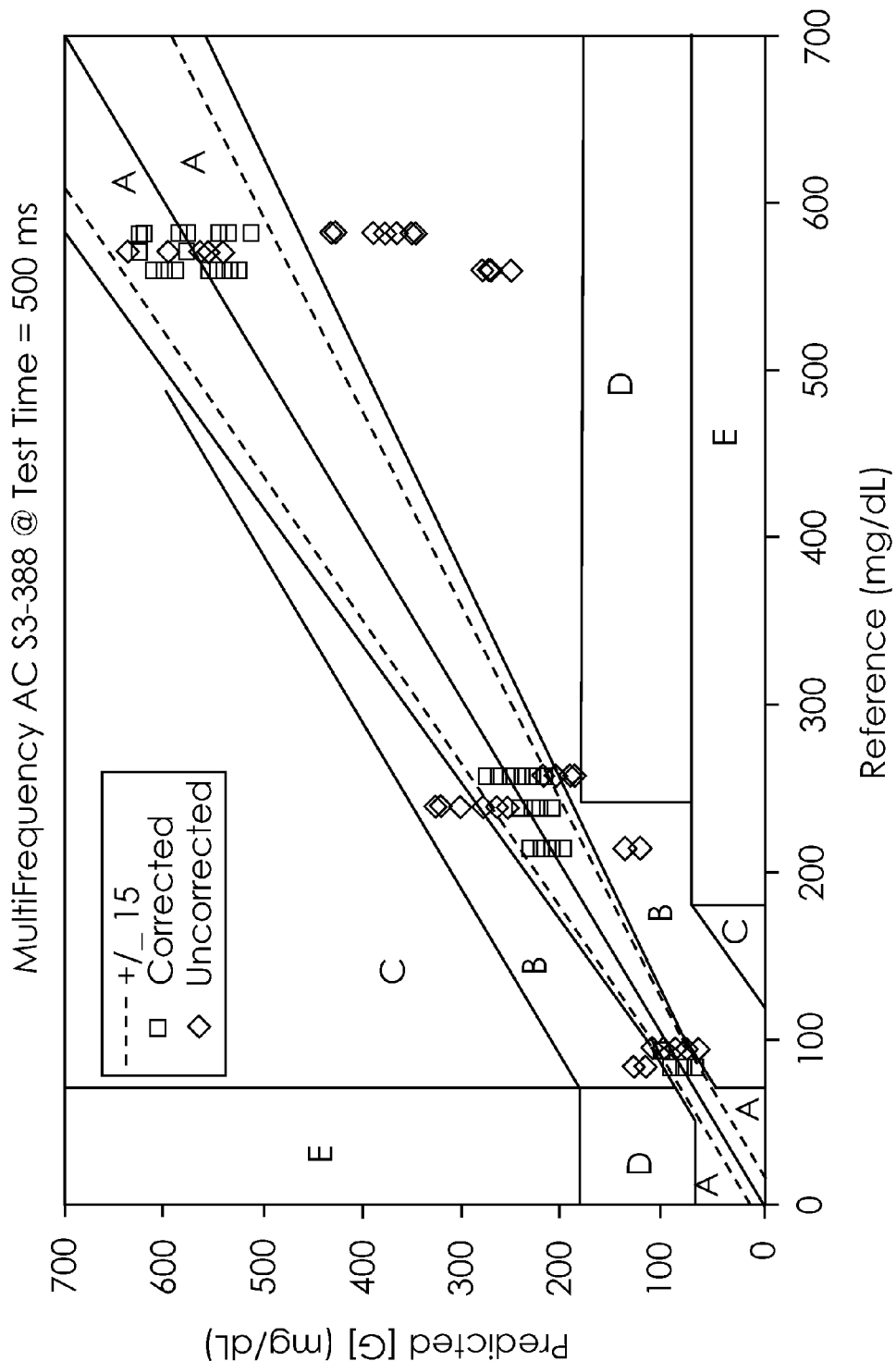
FIG. 21 is a Clark Error Grid showing predicted glucose versus reference glucose for both the uncorrected data of FIG. 19 and the corrected data of FIG. 20.

FIG. 21 is a Clark Error Grid showing the predicted glucose value versus reference glucose value for all of the above 500 ms data points, both corrected and uncorrected. As can be readily seen, the uncorrected glucose values fall well outside the +/−15% error window, while the corrected data are all within this limit. Therefore, the use of multi-frequency excitation to achieve a one-half second glucose Total Test Time was demonstrated.

The above data of this Example 3 clearly shows that the use of the multi-frequency excitation techniques disclosed herein allow extremely short test times by allowing the sample to be simultaneously excited by multiple frequencies and the sample responses to those frequencies to be simultaneously measured. Even at one-half second Total Test Times, the data provides a significant reduction in the DC measurement error caused by interferents, and allows essentially instantaneous measurement results to be reported to the user with a measurement accuracy well within accepted industry standards.

EXAMPLE 4

Multi-Frequency AC Test with Fast Total Test Time

The measurements conducted for Example 4 were made with the same electrode structures and reagents as Example 3 and the same measurement sequencing. However, whereas the Example 3 measurements were performed on samples having three different target analyte concentrations and three different hematocrit levels for each concentration, the Example 4 measurements were performed on samples having seven different target analyte concentrations and three hematocrit levels for each concentration.

As was found in Example 3, it was learned from the measurements of Example 4 that a benefit of using the multi-sine excitation waveform is that the AC measurement time required to collect data for all four frequencies is reduced because the measurements are made simultaneously. Another benefit of the multi-sine excitation waveform is that the AC measurement data for all of the frequencies is collected simultaneously and is thus less affected by the fact that the sample is changing as it reacts with the reagent.

Twenty-one whole blood samples were prepared for a covariate study using target glucose concentrations of 50, 100, 140, 250, 300, 450 and 550 mg/dL and target hematocrit values of 20, 45 and 70%. For each sample tested, each DC time point was analyzed by nonlinear fit and the 300 ms AC admittance magnitude and phase data was used to calculate the predicted glucose response compensated for the effects of hematocrit and temperature using the following equation:

$$\text{Predicted Glucose} = \text{INT} + Yi1*Y1 + Pi1*P1 + Yi2*Y2 + Pi2*P2 + Yi3*Y3 + Pi3*P3 + Yi4*Y4 + Pi4*P4 + \exp(\text{SLOPE} + Ys1*Y1 + Ps1P1 + Ys2*Y2 + Ps2*P2 + Ys3*Y3 + Ps3*P3 + Ys4*Y4 + Ps4*P4)*DC**\text{POWER} \quad \text{(equation 4)}$$

where: Yi1, Yi2, Yi3, Yi4, Ys1, Ys2, Ys3 and Ys4 are constants
Pi1, Pi2, Pi3, Pi4, Ps1, Ps2, Ps3 and Ps4 are constants
Y1 is the admittance magnitude at 1024 Hz
Y2 is the admittance magnitude at 2048 Hz
Y3 is the admittance magnitude at 10240 Hz
Y4 is the admittance magnitude at 20480 Hz
P1 is the phase angle at 1024 Hz
P2 is the phase angle at 2048 Hz
P3 is the phase angle at 10240 Hz
P4 is the phase angle at 20480 Hz
INT is the intercept
SLOPE is the slope
DC is the uncorrected glucose response predicted with the DC measurement $$\text{POWER is} = \text{Const} + Yp1*Y1 + Pp1*P1 + Yp2*Y2 + Pp2*P2 + Yp3*Y3 + Pp3*P3 + Yp4*Y4 + Pp4*P4.$$

Again, Equation 4 is the same form as Equations 1 and 2, but as with Equation 3 from Example 3, one can see that the variables range from Y1 to Y4 and P1 to P4 for the simultaneous AC at 200 ms, rather than Y2-Y5 and P2-P5 which are used in Equations 1 and 2.

Figure 27:
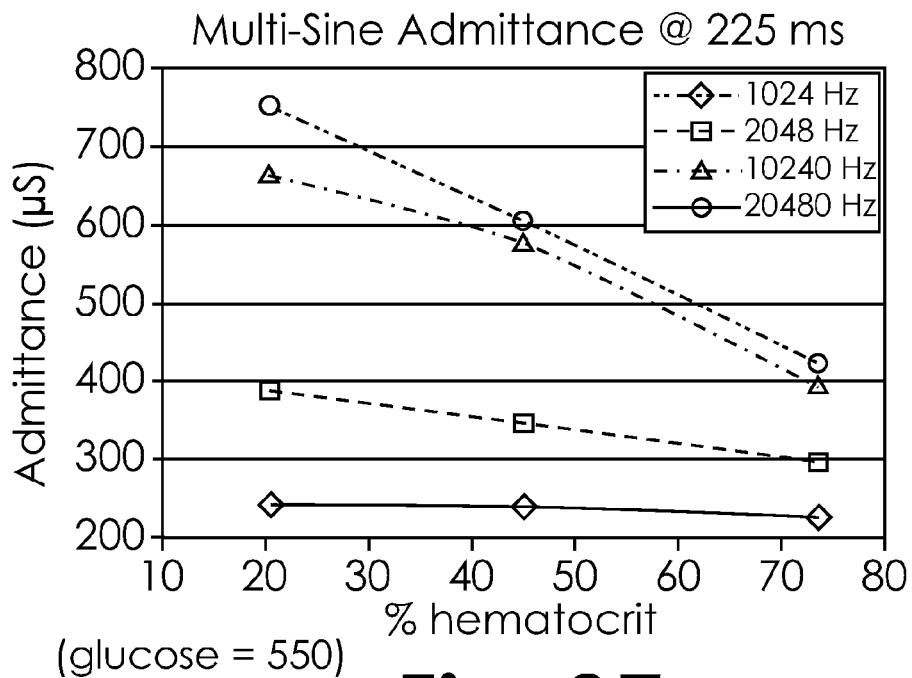
FIG. 27 is a graph of admittance magnitude versus hematocrit from the fourth covariate study described herein.
Figure 28:
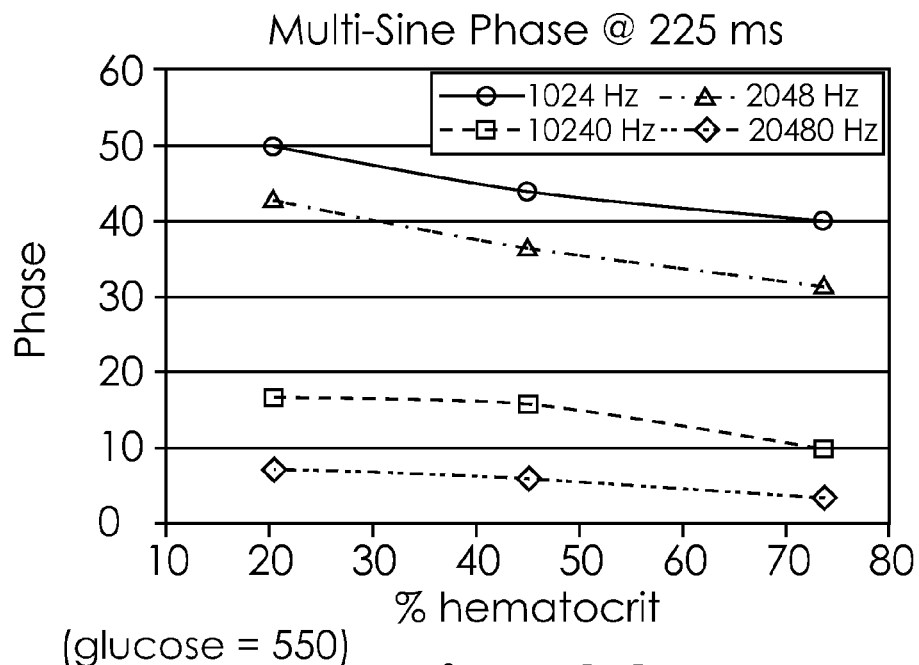
FIG. 28 is a graph of phase versus hematocrit from the fourth covariate study described herein.

As discussed in Example 3, the use of AC admittance magnitude and phase data to correct DC glucose response data for the effects of hematocrit and temperature is discussed in U.S. Pat. No. 7,407,811. A graph of admittance magnitude to hematocrit at each frequency for Example 4 is illustrated in FIG. 27, and a graph of phase to hematocrit at each frequency for Example 4 is illustrated in FIG. 28.

Figures 22, 23:
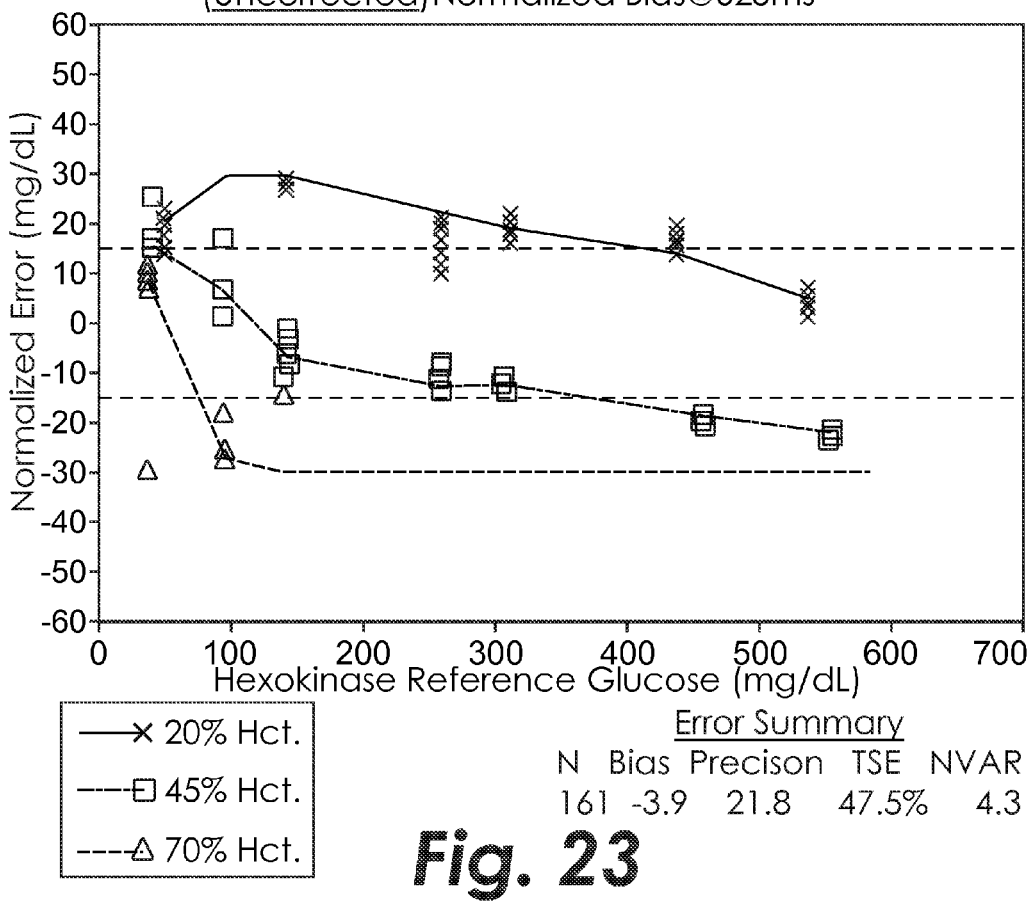
FIG. 22 is a table showing both uncorrected blood glucose measurement evaluations at several test times, as well as measurement evaluations for the same data corrected using the methods disclosed herein, in a fourth study described herein.
FIG. 23 is a graph of normalized error versus reference glucose for uncorrected measurement data from a fourth study described herein.

The uncorrected glucose response from the DC measurement (i.e. uncorrected for the interfering effects of hematocrit and temperature) was determined using well-known prior art techniques. This DC glucose response was then corrected for the interfering effects of hematocrit and temperature using the AC admittance magnitude and phase measurement data as detailed above in equation 4. The Total System Error (TSE), bias, precision and NVar were calculated for each Total Test Time (for both corrected and uncorrected results) and these are tabulated in FIG. 22. As can be readily seen, the performance of the measurement system when corrected for hematocrit and temperature using the AC measurement data is far superior to using only the DC measurement results to predict the glucose values. Furthermore, acquiring the AC measurement data simultaneously for multiple excitation frequencies permits extremely fast Total Test Times. As shown in FIG. 22, measurement results exhibit very good TSE values at Total Test Times of 1.525 seconds, 1.025 seconds, 0.725 seconds and 0.625 seconds.

FIG. 23 plots the normalized error versus the reference glucose value for the uncorrected glucose measurements, and a significant dependence on the hematocrit value can be seen in the data. The Total System Error is 47.5%. FIG. 24 plots the normalized error versus the reference glucose value for the same measurements, only this time the DC measurement data has been corrected using the AC measurement as detailed hereinabove. The interfering effect of the hematocrit has clearly been substantially reduced, with a Total System Error of 10.2%. The measurement data for each of the 21 measurement runs can be seen in FIG. 26.

Figure 25:
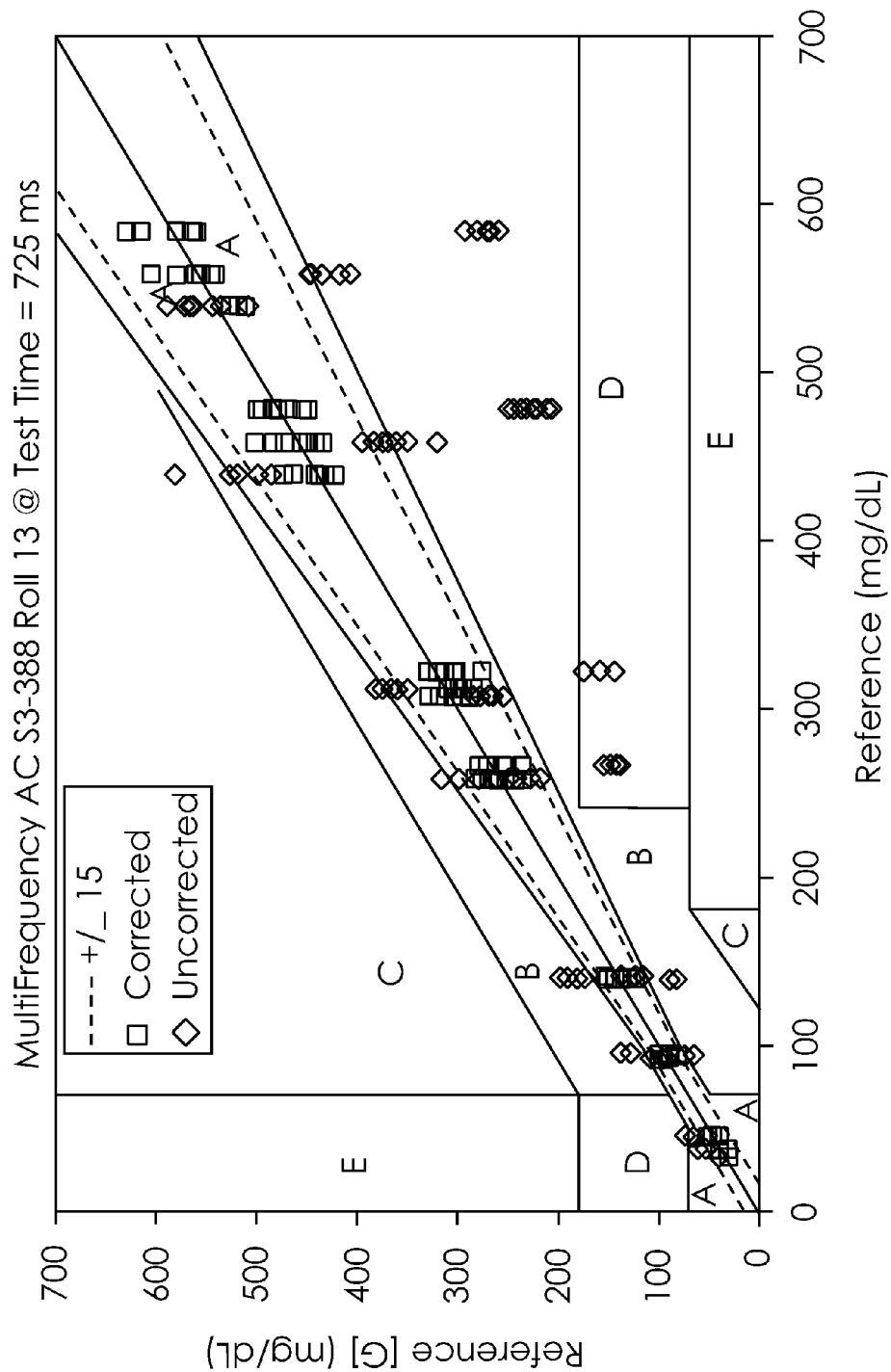
FIG. 25 is a Clark Error Grid showing predicted glucose versus reference glucose for both the uncorrected data of FIG. 23 and the corrected data of FIG. 24.

FIG. 25 is a Clark Error Grid showing the predicted glucose value versus reference glucose value for all of the 725 ms data points, both corrected and uncorrected. As can be readily seen, most of the uncorrected glucose values fall well outside the +/−15% error window, while the corrected data are all within this limit. Therefore, the use of multi-frequency excitation to achieve a less than three-quarters of a second glucose Total Test Time was demonstrated.

The above data of this Example 4 clearly shows that the use of the multi-frequency excitation techniques disclosed herein allow extremely short test times by allowing the sample to be simultaneously excited by multiple frequencies and the sample responses to those frequencies to be simultaneously measured. Even at sub-three-quarter second Total Test Times, the data provides a significant reduction in the DC measurement error caused by interferents, and allows essentially instantaneous measurement results to be reported to the user with a measurement accuracy well within accepted industry standards.

EXAMPLE 5

Sequential Multiple AC Frequency Test with Fast Total Test Time at Various DC Time Points This Example 5 was conducted similarly to Example 2 (above), using test sensors having a reagent film thickness based on a nominal 30 g/m² coat weight application which, as shown in FIG. 30, corresponds approximately to a thickness of 2.45 um. Unlike Example 2, however, data acquisition was conducted using an electrochemical test stand constructed on the basis of VXI components from Agilent, and programmable to apply AC and DC potentials to sensors in requested combinations and sequences and to measure the resulting current responses of the sensors. This was done because, as noted with regard to Examples 1 and 2, the existing meters used with the DATS for those measurements comprise pre-set parameters in which mandatory time blocks are required for a preceding waveform stabilization, trailing communication after each frequency block, and a pre-set "skip" period in the initial 100 ms of DC signal application during which no current response can be measured. For this Example 5, however, it was desired to apply sequential multiple AC frequencies without the limitations of the pre-set timing conditions imposed by the existing meters of the DATS. The Agilent-based test stand used for Example 3 and 4 provided the flexibility to program a desired measurement sequence in this way.

The purpose of Example 5 was to explore different ways in which a set of four short 200 ms AC excitation blocks applied sequentially and having frequencies of 20, 2, 10, and 1 kHz can be used to correct a DC glucose response, co-varied with hematocrit, at a single generally uniform reagent film thickness. The AC excitation blocks were applied starting at a time zero, which is the time at which sufficient sample dosing is detected. Thus, the AC excitation blocks begin at time zero with no open period in between, ending at about 800 ms, at which time the DC excitation was applied.

The DC response data was collected starting at 800 ms through 3700 ms. This dataset was used to analyze the data with varying AC and DC parameters. The goal was to determine if good performance could be reached with this uniform thin film at short test times, and to determine the effect of using one or multiple AC responses for the corrections. FIG. 31 shows the AC response vs. hematocrit for the 4 AC frequencies measured. All of these data show an inverse relationship of admittance response to increased hematocrit. As can be seen, the measurements at the higher frequencies of 20 kHz and 10 kHz exhibit generally similar responses, and the measurements at the lower frequencies of 2 kHz and 1 kHz exhibit generally similar responses. However, the higher frequencies have a greater hematocrit vs. admittance relationship.

Figure 32:
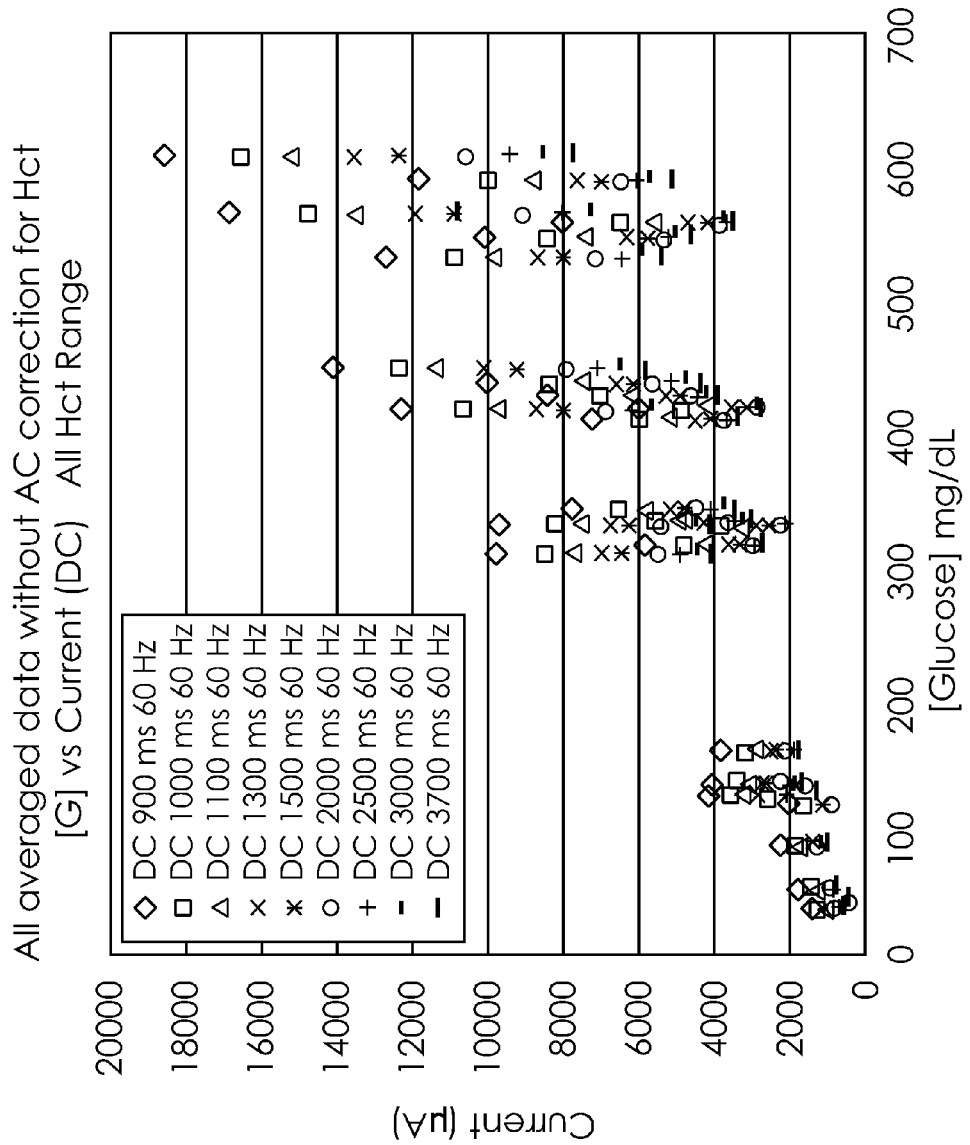
FIG. 32 is a graph of DC current response measured at different test times and co-varied by hematocrit.
Figure 33:
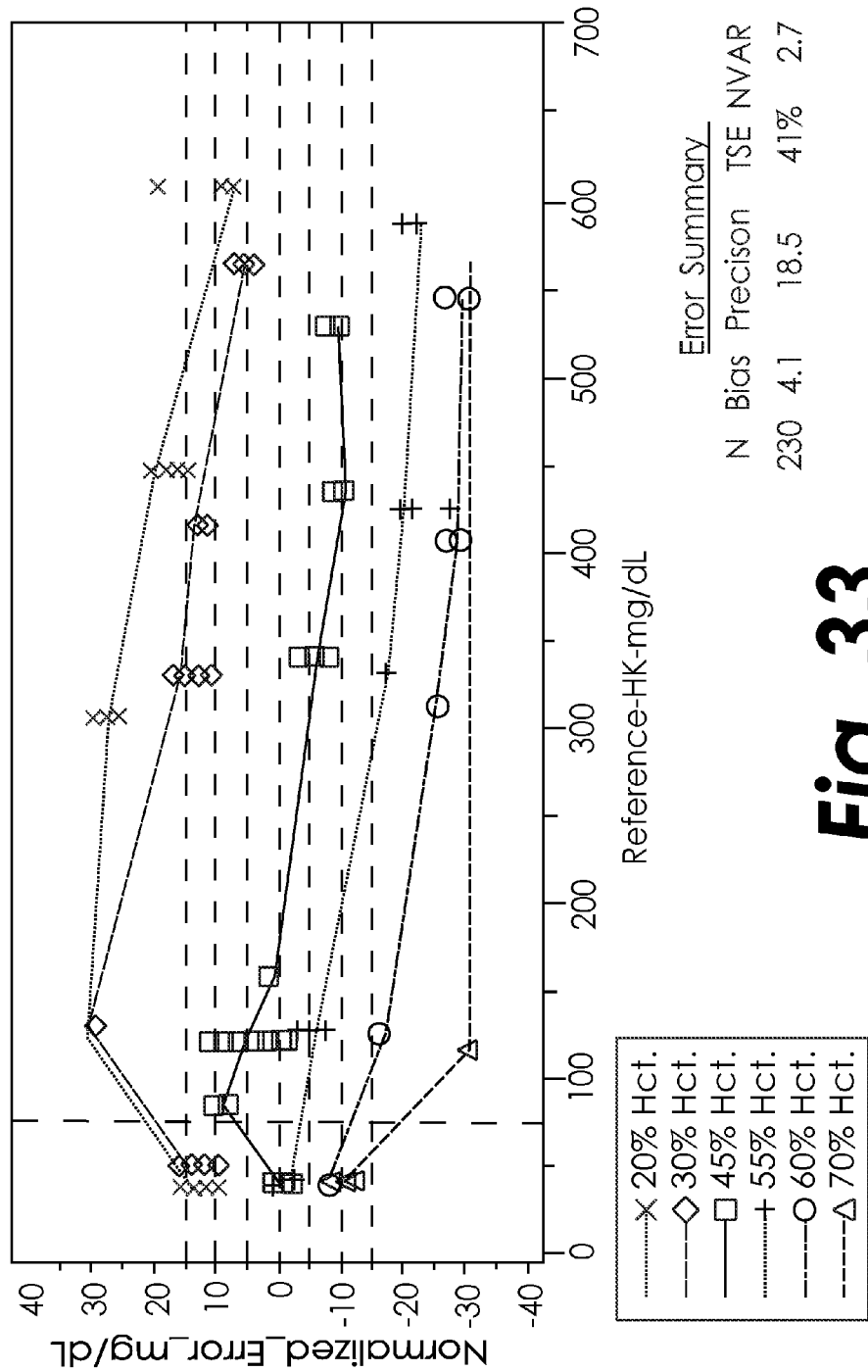
FIG. 33. is a graph of normalized error versus reference glucose for uncorrected DC measurement data measured at 900 ms, from the fifth study described herein.
Figure 34:
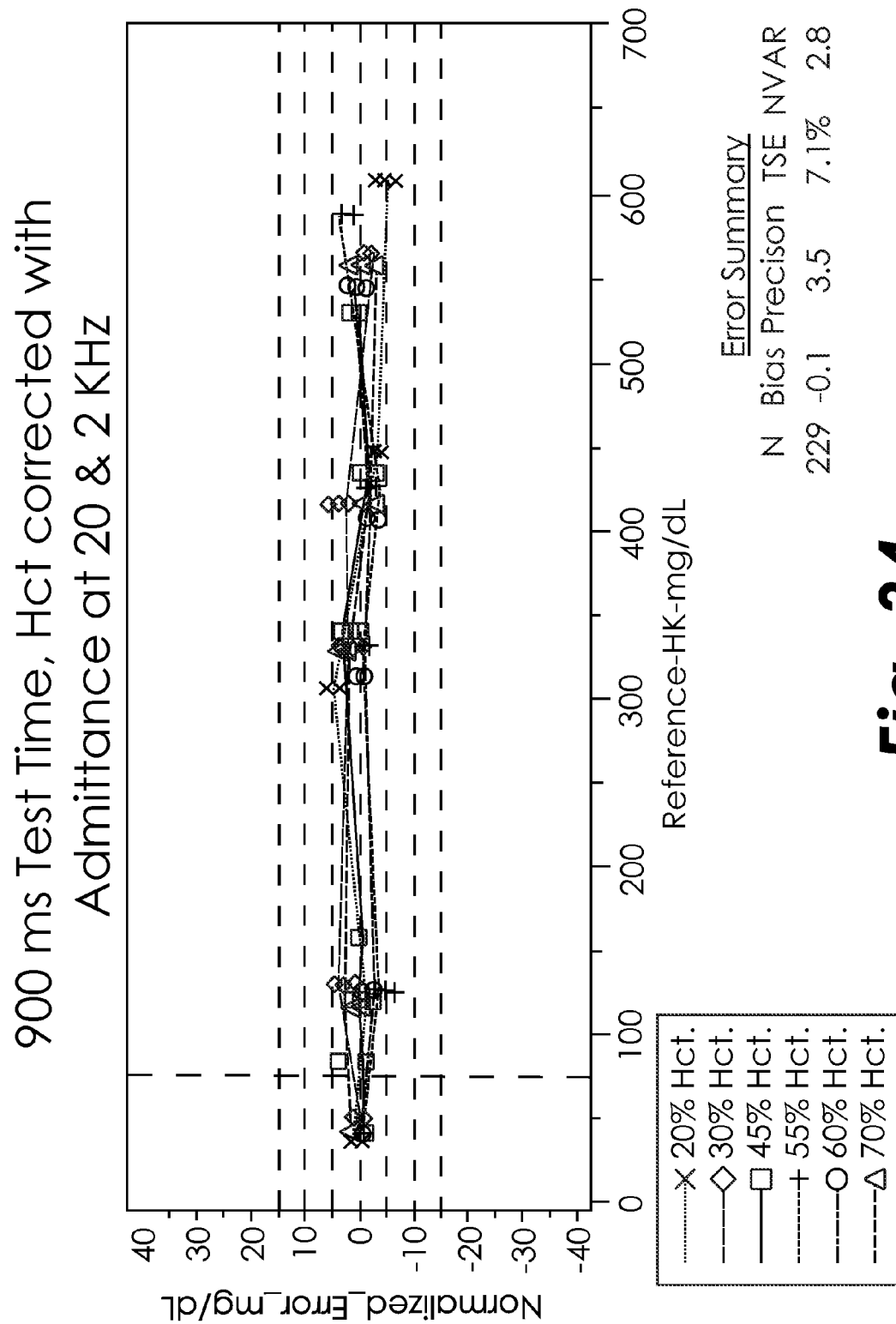
FIG. 34 is a graph of normalized error versus reference glucose for DC measurement data measured at 900 ms and corrected according to the fifth study described herein.
Figure 35:
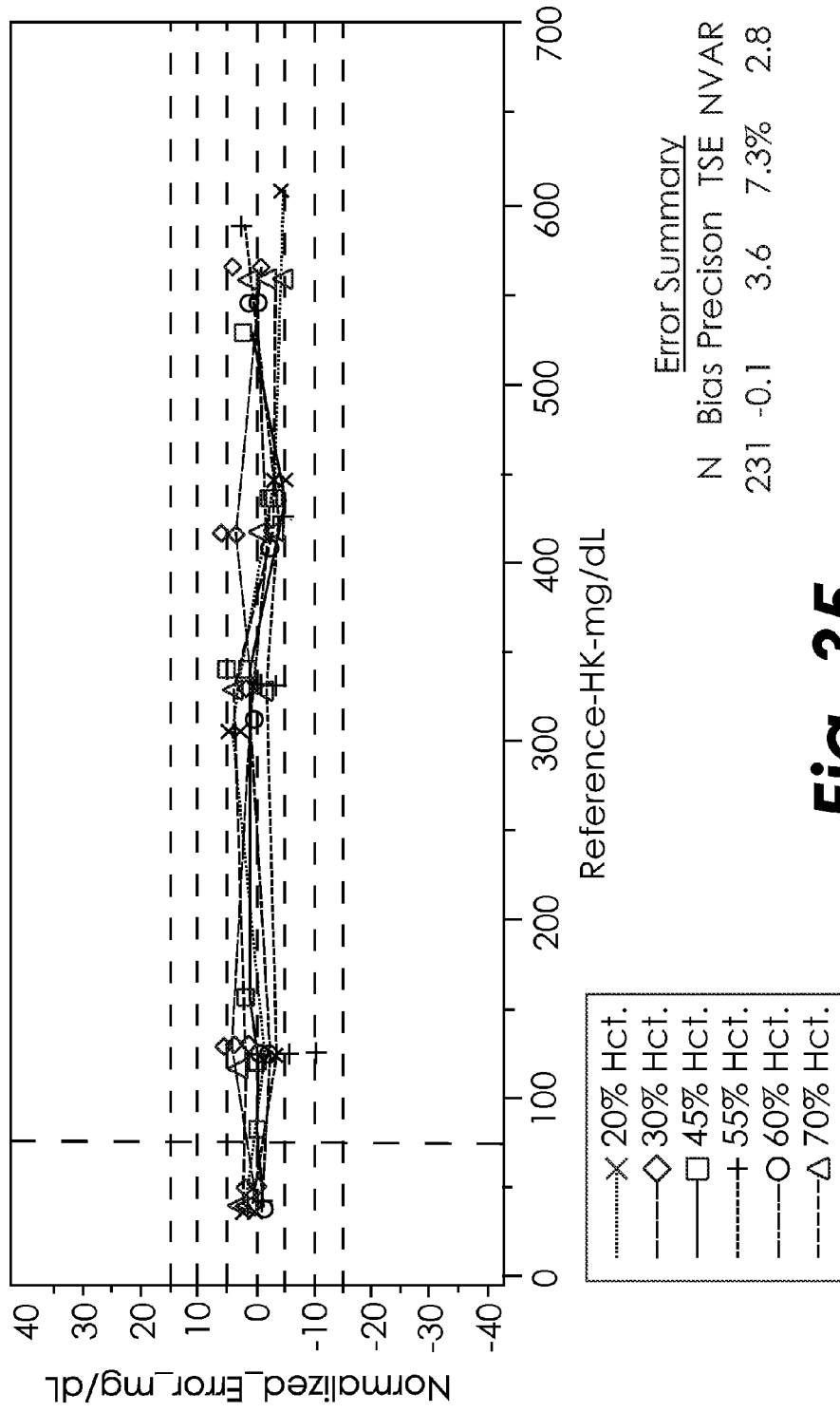
FIG. 35 is a graph of normalized error versus reference glucose for DC measurement data measured at 1100 ms and corrected according to the fifth study described herein.
Figure 36:
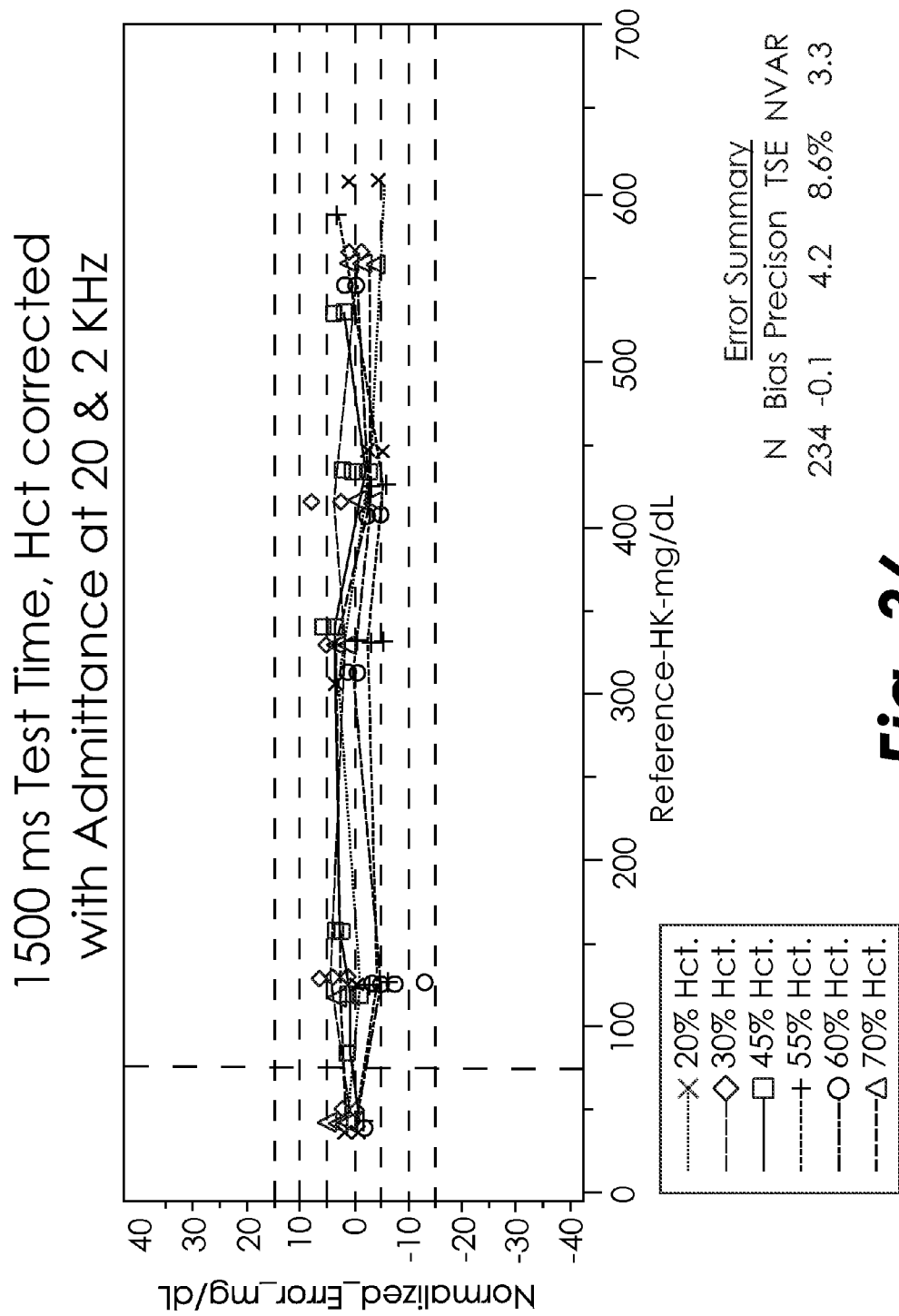
FIG. 36 is a graph of normalized error versus reference glucose for DC measurement data measured at 1500 ms and corrected according to the fifth study described herein.
Figure 37:
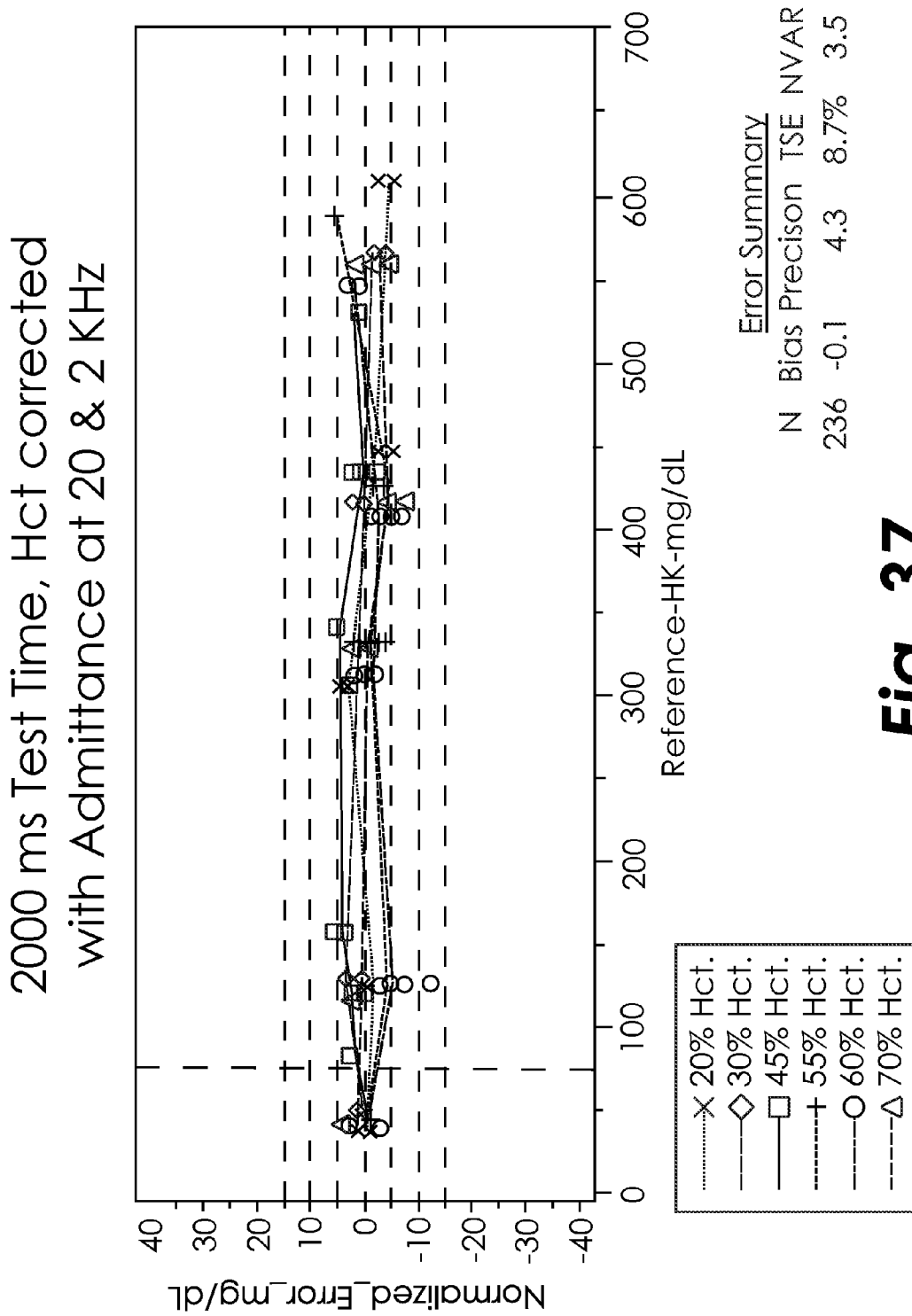
FIG. 37 is a graph of normalized error versus reference glucose for DC measurement data measured at 2000 ms and corrected according to the fifth study described herein.
Figure 38:
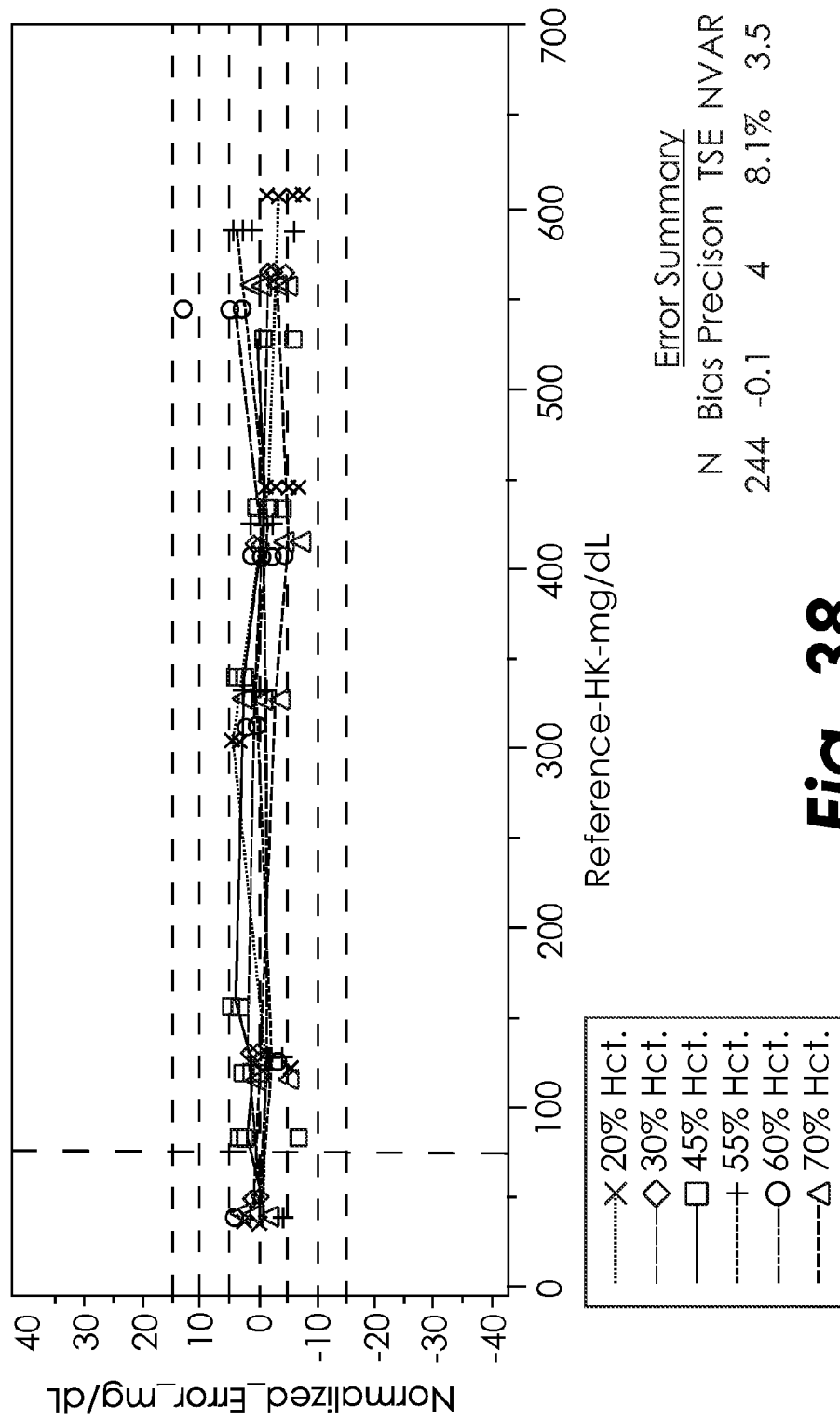
FIG. 38 is a graph of normalized error versus reference glucose for DC measurement data measured at 2500 ms and corrected according to the fifth study described herein.
Figure 39:
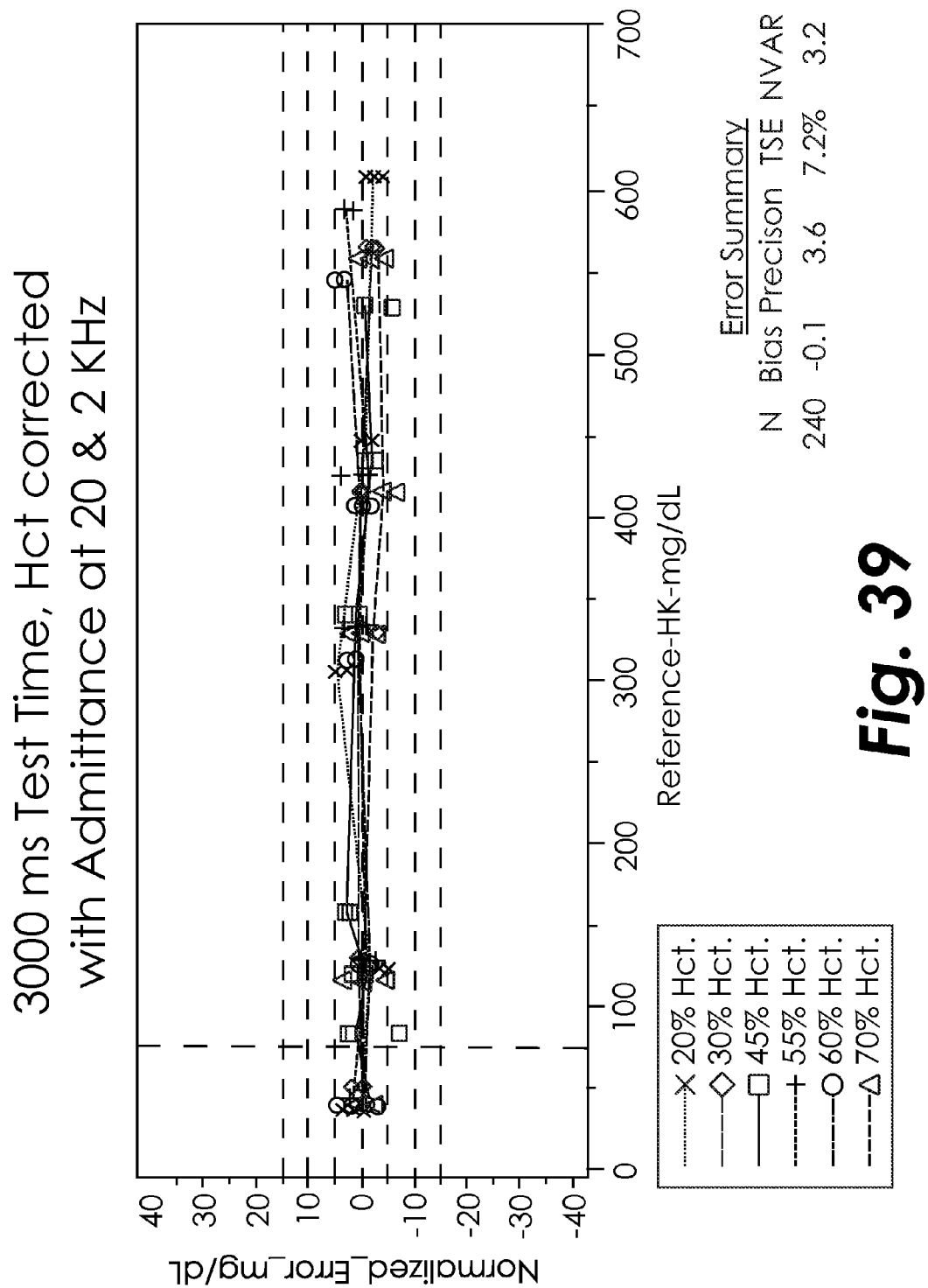
FIG. 39 is a graph of normalized error versus reference glucose for DC measurement data measured at 3000 ins and corrected according to the fifth study described herein.

FIG. 32 shows uncorrected DC response data collected for this covariate study and it is clear that at each DC test time there are variable current responses associated with the varied hematocrit levels. FIG. 33 shows a typical response of an uncorrected Normalized Error to a referenced glucose value for the covariant study using the DC response measured at 900 ms. The uncorrected response has a TSE of 41%. However, as shown in FIG. 34, when the DC response at 900 ms is corrected using the AC response data from just two frequencies, namely 20 kHz and 2 kHz, there is significant improvement of the TSE, which has decreased to 7.1%. FIGS. 35-39 show Normalized Error plots for the corrected DC response measured at 1100 ms, 1500 ms, 2000 ms, 2500 ms, and 3000 ms, respectively, again corrected using only the AC response data from the kHz and 2 kHz sequentially applied frequencies of the AC signal.

FIG. 40 shows a table of the TSE according to variable DC test time for DC response data corrected in two ways, first with the 20 kHz and 2 kHz AC response data and second with the 10 kHz and 1 kHz AC response data. The AC response data at 20 kHz and 2 kHz provided a better correction for this test configuration (in terms of TSE) than the 10 kHz and 1 kHz response data.

FIG. 40 also indicates that at a short test time of 900 ms the TSE is actually better than at longer times; that is, there is an increase in TSE as the DC measurement time increases, but this is then followed by a decrease in TSE at the much longer time of 3000 ms. It is believed that the TSE is lower at the shorter DC measurement times because at the shorter DC measurement times the time between measurement of the AC responses (for obtaining the correction factors) and the measurement of the DC response (for obtaining analyte-related data) is on the order of only 100-900 ms. That is, the AC response data is obtained approximately at times 200 ms, 400 ms, 600 ms and 800 ms, with the shorter DC response data being obtained at 900 and 1100 ms. Thus, the correction factor responses and the analyte response correlate best when film hydration and reaction properties are almost identical. At shorter DC response measurement times measurements are made closer to the electrode surface with short diffusion distances where there is less effect due to film hydration and swelling.

As measurements are made at moderately longer DC response times, the TSE increases because the AC correction factors and the DC response are further apart (less correlated)

because the film is hydrating and swelling rapidly and the DC response is being measured in this region of rapid change. However at even longer DC measurement times, e.g. 3000 ms, the TSE comes back down when the reagent hydration and swelling begins to stabilize, causing the DC value to have less variability and needing less correction by the AC correction factors. Thus, at these longer measurement times, the TSE appears to improve to values close to the TSE of the earlier DC response measurement time. Typically, AC/DC responses taught in prior art disclosures measured the DC response data when the DC response was most stable, which is typically later, and thus lost some of the correlation between correction factors and analyte response. Here we show that we can measure the DC response at earlier measurement times and still obtain an acceptable analyte response with the added benefit of reduced test time. In the case of this Example 5, the Total Test Time is less than 1 second (i.e. 900 ms).

It is also believed that the AC correction factors disclosed herein correct not just the hematocrit affects but also other sources of error or variability of the reagent film state. In the examples described herein, the electrodes used to detect the AC signal response are the same ones used for the DC signal response, and thus are coated with the reagent film. As a result, all AC response measurements are affected by the state of the reagent film with liquid sample applied (e.g. thickness, swelling).

Figure 41:
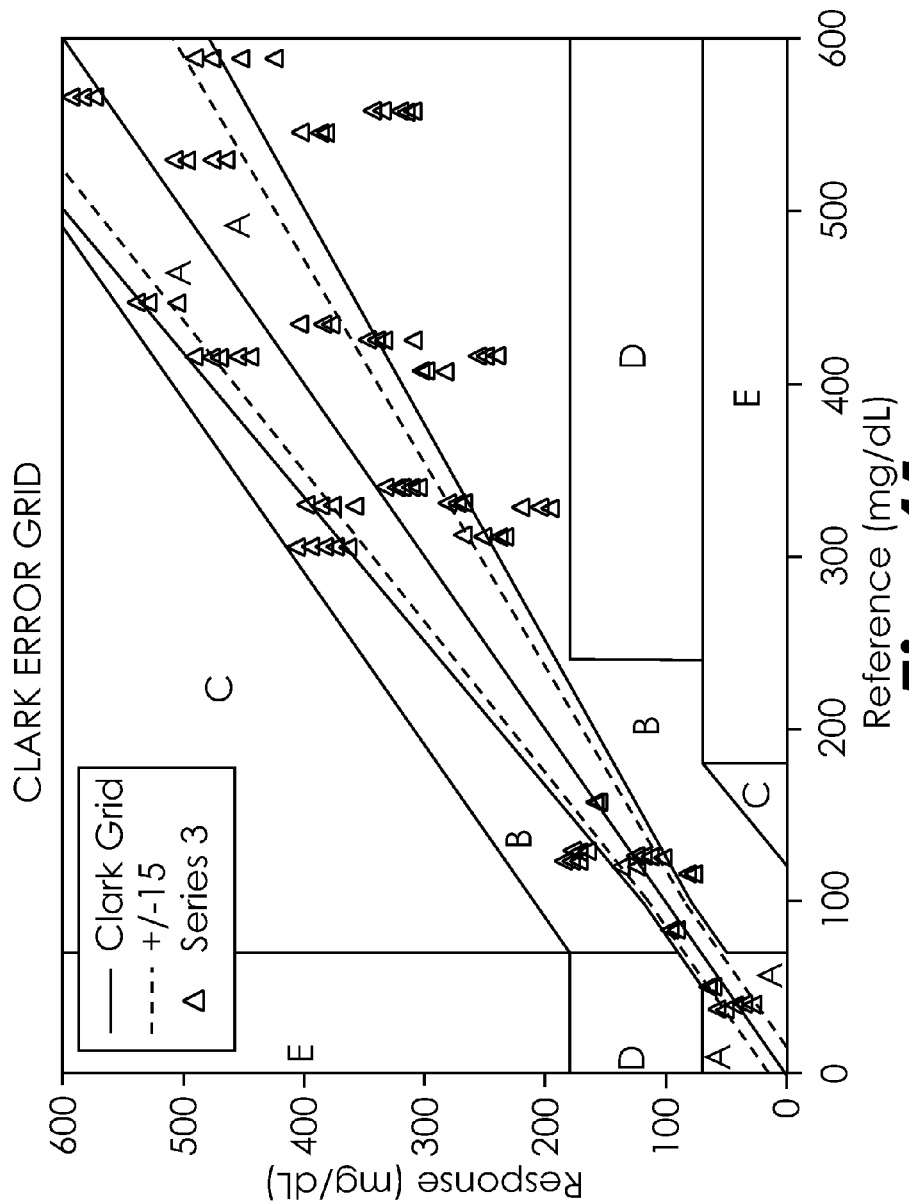
FIG. 41 is a Clark Error Grid showing predicted glucose versus reference glucose for the uncorrected DC response data at 900 ms according to the fifth study described herein.
Figure 42:
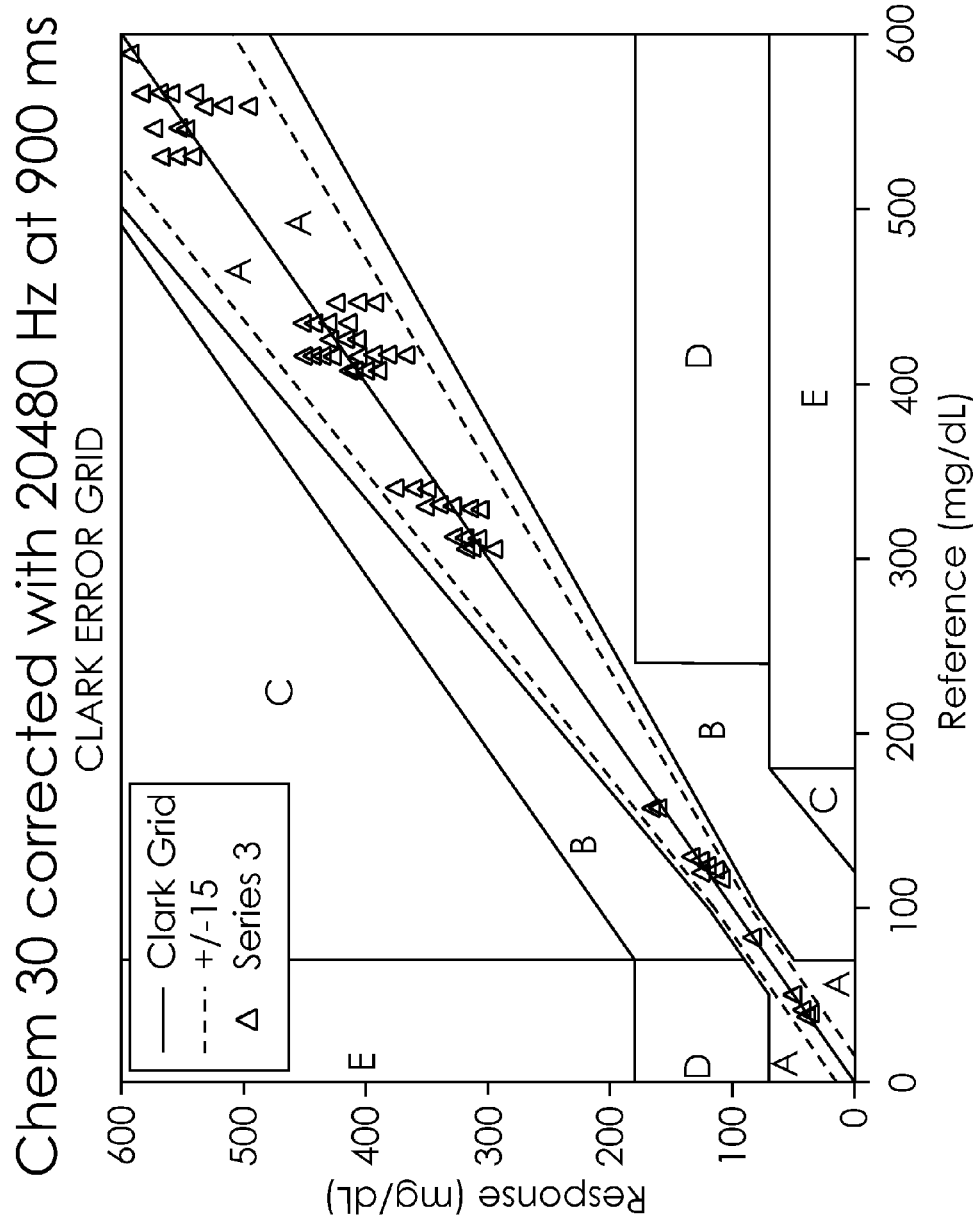
FIG. 42 is a Clark Error Grid showing predicted glucose versus reference glucose for the DC response data at 900 ms corrected by response data from one AC frequency, according to the fifth study described herein.
Figure 43:
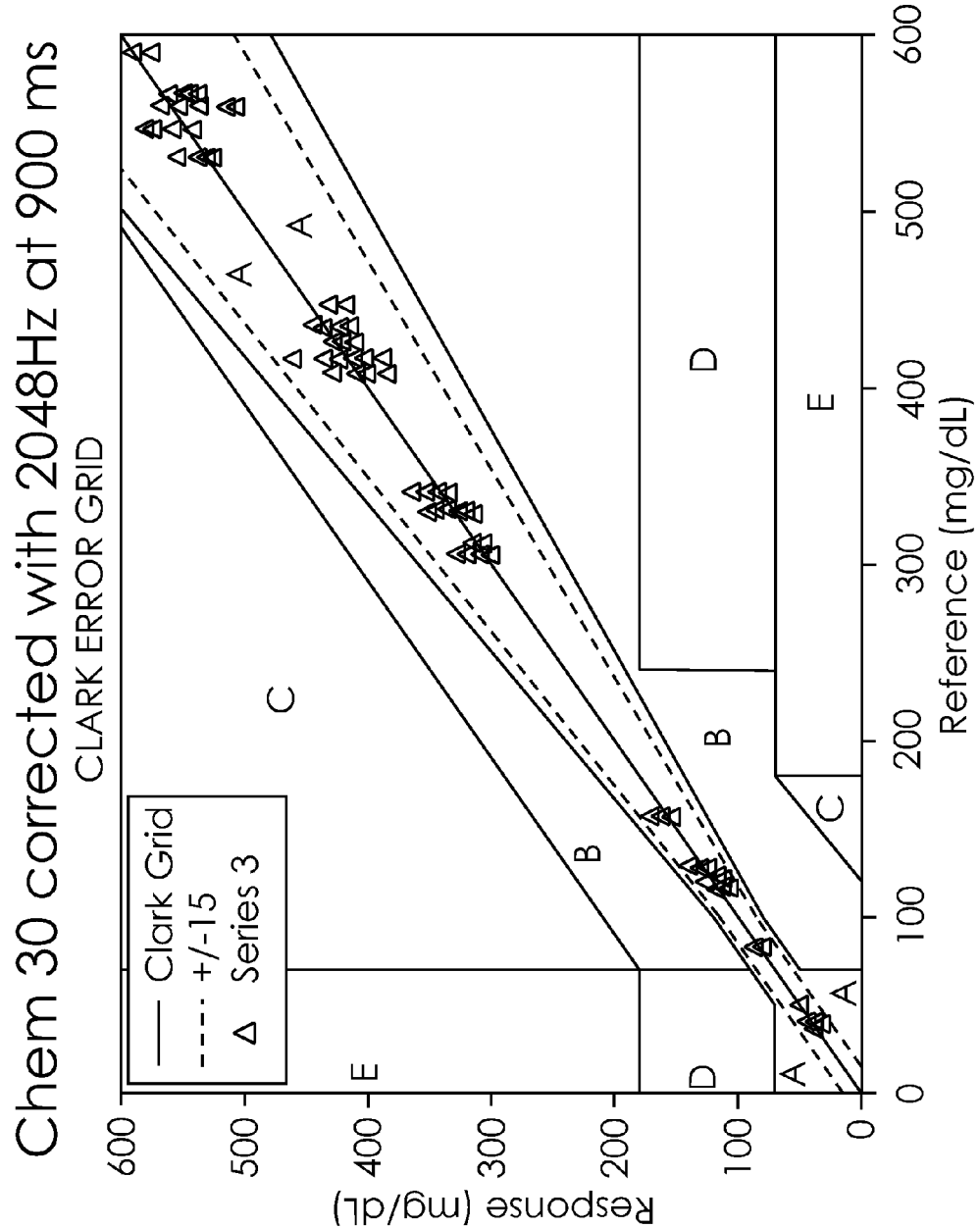
FIG. 43 is a Clark Error Grid showing predicted glucose versus reference glucose for the DC response data at 900 ms corrected by response data from another AC frequency, according to the fifth study described herein.
Figure 44:
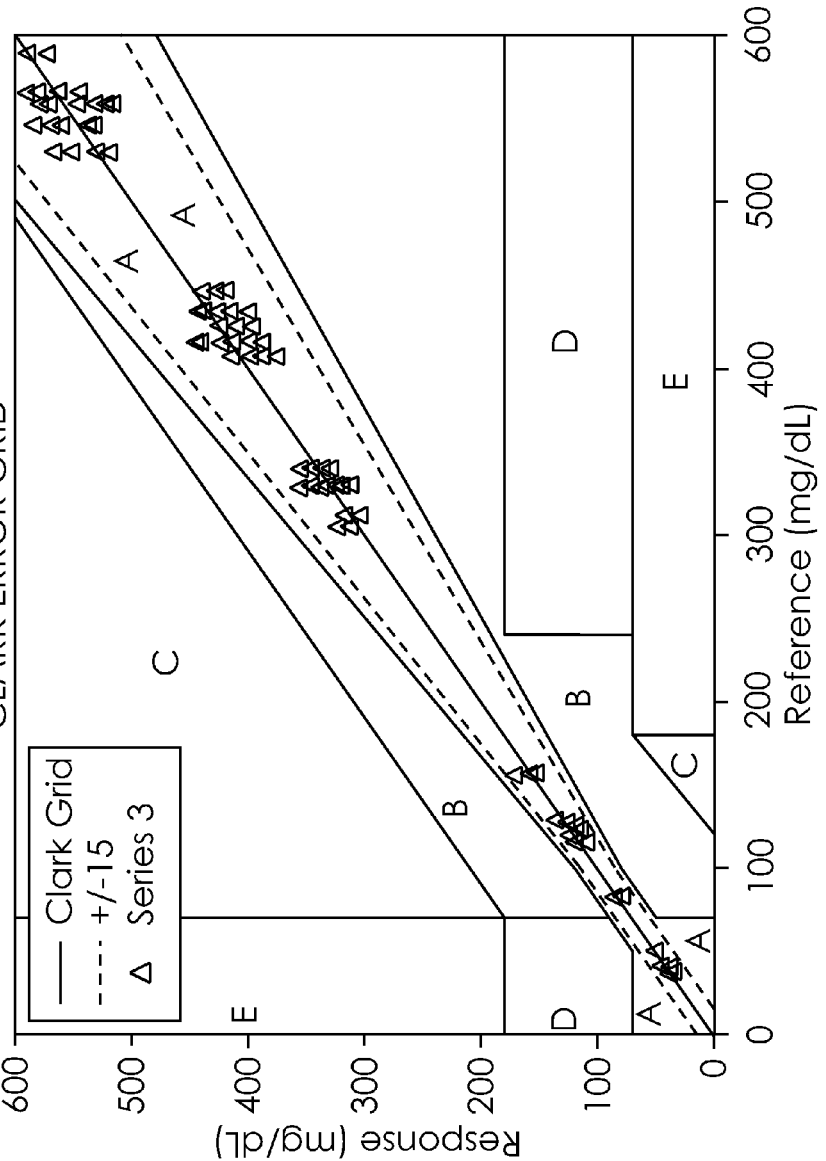
FIG. 44 is a Clark Error Grid showing predicted glucose versus reference glucose for the DC response data at 900 ms corrected by response data from two AC frequencies, according to the fifth study described herein.

Another way to look at these data is from corresponding Clark Error Grids. FIG. 41 shows the Error Grid for the uncorrected DC response data at a 900 ms DC measurement time. FIGS. 42-44 show the same 900 ms DC measurement data corrected with AC response data for only 20 kHz (FIG. 42), only 2 kHz (FIG. 43), and both 20 kHz and 2 kHz (FIG. 44).

The data from Example 5 supports a finding that an analyte measurement having good TSE can be achieved at short Total Test Times, between 900 ms and 3000 ms.

Example 5 was not co-varied with temperature as was done in Example 2 because the electrochemical test stand was less conducive to running "environmental" studies. Thus, the AC signal responses or correction factors determined from those responses in this example do not contain information on sample temperature variations and correction as was shown in Example 2. However, AC methods using the 4 AC frequencies have been shown to correct both hematocrit and temperature variations, and the measurement method of Example 5 would be sufficient to do this with a test time of less than 1000 ms.

For purposes of the examples disclosed herein, the DC excitation applied is described and shown generally as a single block of applied potential for a single duration. DC response data may be taken throughout that duration or only at one or only a few points in that duration. Not shown or described, however, is a DC excitation application which comprises two or more shorter pulses of DC excitation with response data measured for each such pulse. While none of the examples herein illustrate the use of this type of DC excitation, it is believed that the AC waveforms described herein, both sequential and multi-frequency (simultaneous) waveforms, can correct the response data obtained from the pulsed type of DC excitation.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A method for determining a concentration of a medically significant component of a biological fluid in contact with a reagent compound, comprising the steps of:
    a) applying a first signal having an AC component to the biological fluid;
    b) measuring a first response to the first signal;
    c) applying a second signal to the biological fluid, wherein the second signal is a DC signal;
    d) measuring a second response to the second signal; and
    e) combining the first response with the second response to produce an indication of the concentration of the medically significant component;
wherein said first signal comprises a multi-frequency excitation waveform formed by adding a plurality of individual waveforms of varying frequency together so that the fluid sample is excited by multiple frequencies at the same time such that the first response contains measurement data collected simultaneously for all of the multiple frequencies.

2. The method according to claim 1, wherein the first response comprises admittance data corresponding to each frequency of the multi-frequency excitation waveform, the second response comprises an uncorrected response of the medically significant component predicted with the DC signal, and wherein combining the first response with the second response comprises an algorithmic combination of the admittance data and the uncorrected response to calculate a predicted concentration of the medically significant component in the biological fluid.

3. The method according to claim 2, wherein the medically significant component comprises glucose and the biological fluid comprises blood.

4. The method according to claim 1, wherein combining the first response with the second response comprises the steps of determining an interferent correction from the first response, determining an indicated concentration from the second response, and correcting the indicated concentration using the interferent correction.

5. The method according to claim 4, wherein the medically significant component comprises glucose, the biological fluid comprises blood, and the first response comprises information pertaining substantially only to one or both of hematocrit and temperature.

6. The method according to claim 1, wherein the total time from applying the first signal to measuring the second response is within about 2.0 seconds.

7. The method according to claim 1, wherein the method has a Total System Error of less than about 15%.

8. The method according to claim 1, wherein the multi-frequency excitation waveform comprises at least two frequencies selected from the group consisting of about 1 kHz, about 2 kHz, about 10 kHz and about 20 kHz.

9. The method according to claim 8, wherein measuring the first response comprises measuring one or both of admittance and phase information corresponding to each of the frequencies comprising the multi-frequency excitation waveform generally simultaneously.

10. The method according to claim 9, wherein measuring the second response occurs within about 1000 ms or less after the measuring the first response.

11. The method of claim 6, wherein the determination has a Total Test Time of between about 0.5 seconds and about 1,525 seconds, and wherein the method has a Total System Error of less than about 11%.

* * * * *

UNITED STATES PATENT AND TRADEMARK OFFICE
CERTIFICATE OF CORRECTION

| | | |
|---|---|---|
| PATENT NO. | : 8,148,164 B2 | Page 1 of 1 |
| APPLICATION NO. | : 12/650065 | |
| DATED | : April 3, 2012 | |
| INVENTOR(S) | : Eric R. Diebold et al. | |

It is certified that error appears in the above-identified patent and that said Letters Patent is hereby corrected as shown below:

Col. 28, line 9, replace "1,525" with --1.525--

Signed and Sealed this
Twenty-ninth Day of May, 2012

David J. Kappos
*Director of the United States Patent and Trademark Office*